US006262055B1

(12) United States Patent
Young et al.

(10) Patent No.: US 6,262,055 B1
(45) Date of Patent: *Jul. 17, 2001

(54) HIV INTEGRASE INHIBITORS

(75) Inventors: Steven D. Young, Lansdale; John S. Wai, Harleysville; Mark W. Embrey, North Wales; Thorsten E. Fisher, Hatfield, all of PA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/323,457

(22) Filed: Jun. 1, 1999

Related U.S. Application Data

(60) Provisional application No. 60/087,846, filed on Jun. 3, 1998.

(51) Int. Cl.[7] ............... A61K 31/495; A61K 31/425; A61K 31/38; C07D 333/74; C07D 333/56
(52) U.S. Cl. ............... 514/252; 514/365; 514/443; 514/448; 549/43; 549/57; 549/72; 548/200
(58) Field of Search ............... 514/443, 448, 514/365, 252; 549/57, 72, 43; 548/200

(56) References Cited

U.S. PATENT DOCUMENTS

| 3,772,336 | * 11/1973 | Wright ............... 549/57 |
| 3,899,508 | 8/1975 | Wikel . |
| 4,336,397 | 6/1982 | Cragoe, Jr. et al. ............... 560/51 |
| 4,377,258 | 3/1983 | Kipp, Jr. ............... 241/27 |
| 4,386,092 | * 5/1983 | Oe et al. ............... 424/256 |
| 4,423,063 | 12/1983 | Rooney et al. ............... 424/278 |
| 5,134,142 | * 7/1992 | Matsuo et al. ............... 514/255 |
| 5,516,797 | 5/1996 | Armistead et al. . |
| 5,618,830 | 4/1997 | Selnick et al. . |

FOREIGN PATENT DOCUMENTS

| 418 845 | 3/1991 | (EP) . |
| 61-134346 | 3/1984 | (JP) . |
| WO 97/17316 | 5/1997 | (WO) . |
| WO 97/17317 | 5/1997 | (WO) . |
| WO 99/30699 | 6/1999 | (WO) . |
| WO 00/06529 | 2/2000 | (WO) . |
| WO 00/39086 | 7/2000 | (WO) . |

OTHER PUBLICATIONS

Burch et al, "Acylpyruvates as potential antifungal agents", CA77:14833, 1972.*

Zhao, et al., Hydrazide–Containing Inhibitors of HIV–1 Integrase, J. Med. Chem., (1997), vol. 40, No. 8, pp. 937–941.

Zhao, et al., Arylamide Inhibitors of HIV–1 Integrase, J. Med. Chem., (1997), vol. 40, No. 8, pp. 1186–1194.

Williams, et al., Inhibitors of Glycolic Acid Oxidase. 4–Substituted 2,4–Dioxobutanoic Acid Derivatives, J. Med. Chem., (1983), vol. 26, pp. 1196–1200.

Tomassini, et al., Inhibition of Cap (m7 GpppXm)–Dependent Endonuclease of Influenza Virus by 4–Substituted 2,4–Dioxobutanoic Acid Compounds, Antimicrobial Agents & Chemotherapy (1994), vol. 38, No. 12, pp. 2827–2837.

Ratner, et al., Complete nucleotide sequence of the AIDS virus, HTLV–III, Nature, (1985) vol. 313, pp. 277–284.

Toh, et al., Close structural resemblance between putative polymerase of a Drosophila transposable genetic element 17.6 and pol gene product of Moloney murine leukaemia virus. The EMBO Journal, (1985), vol. 4, No. 5, pp. 1267–1272.

Power, et al., Nucleotide Sequence of SRV–1, a Type D Simian Acquired Immune Deficiency Syndrome Retrovirus, Science, (1986), vol. 231, pp. 1567–1572.

Pearl, et al., A structural model for the retroviral proteases, Nature, (1987), vol. 329, pp. 351–354.

LaFemina, et al., Inhibition of Human Immunodeficiency Virus Integrase by Bis–Catechols, Antimocrobial Agents & Chemotherapy, (1995), vol. 39, No. 2, pp. 320–324.

Giordani, et al., 4–Phenyl–4–oxo–butanoic Acid Derivatives Inhibitors of Kynurenine 3–Hydroxylase, Bioorganic & Medicinal Chemistry Letters, (1998), vol. 8, pp. 2907–2912.

Hastings, et al., Anti–Influenza Virus Activities of 4–Substituted 2,4–Dioxobutanoic Acid Inhibitors, Antimicrobial Agents and Chemotherapy, (May 1996) vol. 40, No. 5, pp. 1304–1307.

Howarth et al., J.C.S. Perkins Trans, 1, Pyrolles and related compounds . . . , (1974), vol. 4, pp. 490–501.

Tanaka et al., Bull. Chem. Soc. JPN., Studies on Aromatic Sesquiterpenes . . . (1989), vol. 62, No. 6, pp. 2102–2104.

Freri, Variations in the Claisen condensation reaction, 1938, Chemical Abstracts No. 33:2488.

Lin et al., Substituted pyrazolyl compounds and methods employing these compounds, 1996, Chemical Abstracts No. 124: 202242 (HCAPLUS).

(List continued on next page.)

Primary Examiner—Deborah C. Lambkin
(74) Attorney, Agent, or Firm—Kenneth R. Walton; Melvin Winokur

(57) ABSTRACT

Sulfur-containing heteroaryl dioxo-butyric acid derivatives are described as inhibitors of HIV integrase and inhibitors of HIV replication. These compounds are useful in the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

34 Claims, No Drawings

OTHER PUBLICATIONS

R.M. Saleh, Use of ethyl 2–thenoylpyruvate in the synthesis of heterocycles and their derivatives, 1991, Chemical Abstracts No. 114: No. 228839 (HCAPLUS).

Yanborisov, et al., Synthesis and pharmacological activity of heteroylpyruvic acids and their derivatives, 1998, Chemical Abstracts No. 130: 153601 (HCAPLUS).

Murray, et al., J. Heterocyclic Chem., A Simple Regioselective Synthesis of Ethyl 1,5 Diarylpyrazole–3–carboxylates, (1989), vol. 26, pp. 1389–1392.

Witiak, et al., Journal of Med. Chem., Synthesis of Ethyl 6–substituted–Chroman–and–Chromone–2–carboxylates, (1975), vol. 18, No. 9, pp. 934–942.

Andreichekov, et al., Synthesis of 4–Aroyltetrahydro–1, 5–diphenyl–2,3–pyrrolediones . . . 1986, Chemical Abstracts No. 107:39766.

Oka, et al., Chem. Pharm. Bull., Studies on the Sytheses of N–Heterocyclic Compounds XXVI . . . (1975), 23 (10), pp. 2306–2317.

Oka, et al., Chem. Pharm. Bull., Studies on the Sytheses of N–Heterocyclic Compounds XXV . . . 23 (10), pp. 2239–2250, 1975.

Cooke et al., Aust. J. Chem., Colouring Matters of Australian Plants, XXIII . . . (1980), 33, pp. 2317–2324.

Seki, et al., J. Heterocyclic Chem., 3–Phenacylidene–3, 4–dihydro–1H–pyrido[2,3–b]pyrazin–2–ones . . . (1995), 32, pp. 347–348.

Sweeny, et al., Tetrahedron, Synthesis of Anthocycandins–III . . . , (1981) 37, pp. 1481–1483.

Schummer, et al., Tetrahedron, Polyfunctional (R)–2–Hydroxycarboxylic . . . , (1991), 47 (43), pp. 9019–9034.

Munakata, et al., "Pyrazole derivatives", 1980, Chemical Abstracts No. 93: 550250 (HCAPLUS).

Derwent Abstract No. 1999–580735/49, "New indole derivatives are integrase inhibitors useful as antiviral and anit–HIV agents", abstract of WO 99/50245 (Shionogi & Co., Ltd.), 1999.

Derwent Abstract No. 2000–465713, "New and known di–heterocyclyl hydroxypropenone derivatives are integrase inhibitors for treating retroviral infections, including HIV and AIDS", abstract of WO 00/39086 (Shionogi & Co., Ltd.), 2000.

Y. Goldgur et al., "Structure of the HIV–1 integrase catalytic domain complexed with an inhibitor: A platform for antiviral drug design", Proc. Nat'l Acad. Science USA, vol. 96, No. 23, pp. 13040–13043 (Nov. 9, 1999).

* cited by examiner

HIV INTEGRASE INHIBITORS

CROSS-REFERENCE TO RELATED APPLICATIONS

The present application claims priority of U.S. provisional application Serial No. 60/087,846, filed Jun. 3, 1998.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, e.g., azidothymidine or AZT. Applicants demonstrate that the compounds of this invention are inhibitors of HIV integrase and inhibitors of HIV replication. The applicants additionally demonstrate that inhibition of integrase in vitro and HIV replication in cells is a direct result of inhibiting the strand transfer reaction catalyzed by the recombinant integrase in vitro and integrase as a component of the preintegration complex in HIV infected cells. The particular advantage of the present invention is highly specific inhibition of HIV integrase and HIV replication. The compounds of the present invention inhibit integrases of closely related lentiviruses such as HIV 2 and SIV, but not integrases from more distantly related retroviruses, for example RSV. These compounds do not inhibit binding or catalysis of other nucleic acid binding proteins, including enzymatic reactions such as those catalyzed by HIV reverse transcriptase, HIV Rnase H, Influenza transcriptase, Hepatitis C polymerase, Yeast DNA polymerase, DNase I, Eco RI endonuclease, or mammalian polymerase II.

Zhao et al., (J. Med Chem. vol. 40, pp. 937–941 and 1186–1194 (1997)) describe hydrazide and arylamide HIV integrase inhibitors. Bis-catechols useful for inhibiting HIV integrase are described in LaFemina et al. (Antimicrobial Agents & Chemotherapy, vol. 39, no. 2, pp. 320–324, February 1995).

U.S. Pat. Nos. 4,377,258; 4,336,397; and 4,423,063 as well as Williams and Rooney (J. Med. Chem. vol 26, pp. 1196–1200, 1983) disclose 2,4-dioxo-4-substituted-1-butanoic acid derivatives useful intreating urinary tract calcium oxalate lithiasis. 4-substituted 2,4-dioxobutanoic acid compounds useful for inhibiting an influenza virus endonuclease are described in Tomassini et al. (Antimicrobial Agents & Chemotherapy, vol. 38, no. 12, pp. 2827–2837, December, 1994).

Applicants have discovered that certain 5-membered sulfur containing heteroaromatic diketo acid derivatives are potent inhibitors of HIV integrase. These compounds are useful in the treatment of AIDS or HIV infection.

SUMMARY OF THE INVENTION

Compounds of formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION

This invention is concerned with compounds of formula I, combinations thereof, or pharmaceutically acceptable salts thereof, in the inhibition of HIV integrase, the prevention or treatment of infection by HIV and in the treatment of the resulting acquired immune deficiency syndrome (AIDS). Compounds of formula I are defined as follows:

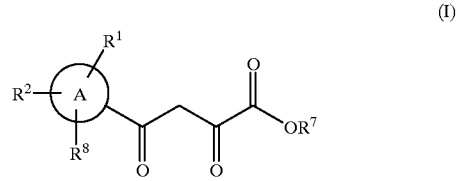

(I)

and tautomers or pharmaceutically acceptable salts thereof, wherein:

A is a five-membered heteroaromatic ring containing 1 sulfur atom and 0 or 1 nitrogen atoms and substituted on carbon by $R^1$, $R^2$ and $R^8$; the heteroaromatic ring may optionally be fused with a phenyl ring or a $C_{4-6}$ cycloalkyl ring, or with two six membered rings to form:

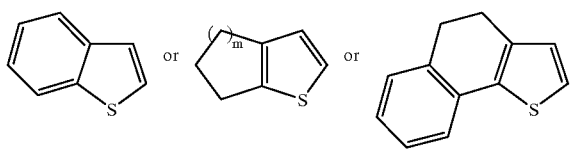

$R^1$ is selected from:
 (1) —H,
 (2) —$C_{1-5}$ alkyl,
 (3) —$CF_3$,
 (4) —halo,
 (5) —$NO_2$,
 (6) —$N(R^4)(R^5)$,
 (7) —$R^6$, (8) —C$_{2-5}$ alkenyl-R$^3$,
(9) —C$_{2-5}$ alkynyl-R$^3$,
(10) —O—R$^6$,
(11) —O—C$_{1-6}$ alkyl, and
(12) —C(O)CH$_2$C(O)C(O)OR$^7$;

R$^2$ is selected from:
(1) —H,
(2) —R$^3$,
(3) —C$_{1-6}$ alkyl,
(4) —C$_{1-6}$ alkyl substituted with R$^3$,
(5) —O—R$^6$,
(6) —O—C$_{1-6}$ alkyl-OR$^6$,
(7) —S(O)n—R$^6$,
(8) —C$_{1-6}$ alkyl (OR$^6$)(R$^4$),
(9) —C$_{1-6}$ alkyl (OR$^4$)(R$^6$),
(10) —C$_{0-6}$ alkyl-N(R$^4$)(R$^6$),
(11) —C$_{1-6}$ alkyl S(O)n—R$^6$,
(12) —C$_{0-6}$ alkyl C(O)—R$^6$,
(13) —C$_{0-6}$ alkyl C(S)—R$^6$,
(14) —C$_{0-6}$ alkyl NR$^4$C(O)—R$^6$, and
(15) —C$_{0-6}$ alkyl-C(O)N(R$^4$)(R$^5$);

each R$^3$ is independently selected from:
(1) a 5 or 6 membered aromatic or heteroaromatic ring, containing 0, 1, 2, 3, or 4 heteroatoms selected from oxygen, nitrogen and sulfur, unsubstituted or substituted on a nitrogen or carbon atom by 1 to 5 substituents selected from:
  (a) halogen,
  (b) C$_{1-6}$ alkyl,
  (c) C$_{1-6}$ alkyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen,
    (ii) C$_{1-6}$ alkyl,
    (iii) —CF$_3$, and
    (iv) hydroxy;
(2) a 3 to 6 membered saturated ring containing 0 or 1 heteroatoms selected from oxygen, nitrogen or sulfur, unsubstituted or substituted with 0 to 5 substituents selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O,
  (h) hydroxy;
(3) unsubstituted or substituted hexahydrothieno[3,4-d]imidazolyl with one or two substituents selected from:
  (a) oxo,
  (b) halogen,
  (c) C$_{1-6}$ alkyl,
  (d) C$_{1-6}$ alkyloxy-,
  (e) —CF$_3$,
  (f) —OCF$_3$,
  (g) —CN, and
  (h) hydroxy;
(4) a 5 or 6 membered aromatic or heteroaromatic ring, containing 0, 1, or 2 heteroatoms selected from oxygen, nitrogen and sulfur, fused with a phenyl ring; wherein the ring system is unsubstituted or substituted on a nitrogen or carbon atom by 1 to 3 substituents selected from:
  (a) -halogen,
  (b) —C$_{1-6}$ alkyl,
  (c) —C$_{1-6}$ alkyloxy-,
  (d) —CF$_3$,
  (e) —OCF$_3$,
  (f) —CN, and
  (g) -hydroxy;
(5) a 3 to 6 membered saturated ring containing 0 or 1 heteroatoms selected from oxygen, nitrogen or sulfur, fused with a phenyl ring, unsubstituted or substituted with 1 or 2 substituents selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O,
  (h) hydroxy;
(6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O,
  (h) hydroxy;

each R$^4$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$,
(7) —C$_{2-3}$ alkenyl-R$^3$,
(8) —S(O)n—R$^3$, and
(9) —C(O)—R$^3$;

each R$^5$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$,
(7) —C$_{2-3}$ alkenyl-R$^3$,
(8) —S(O)$_n$—R$^3$, and
(9) —C(O)—R$^3$;

each R$^6$ is independently selected from:
(1) —C$_{1-3}$ alkyl-R$^3$, and
(2) —R$^3$;

R$^7$ is selected from:
(1) —H, and
(2) C$_{1-6}$ alkyl;

R$^8$ is selected from:
(1) —H, and
(2) C$_{1-6}$ alkyl-oxy-;
(3) C$_{1-6}$ alkyl-;

each n is independently selected from 0, 1 and 2, and
each m is independently selected from 0, 1, and 2.
Particular compounds of structural formula I include:
(1)
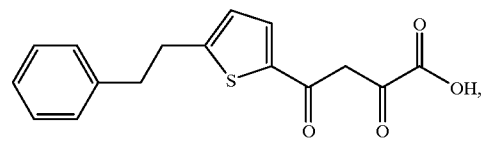
(2)
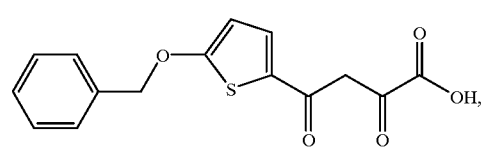
(3)
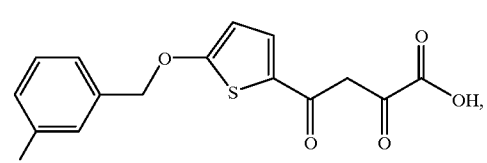
(4)
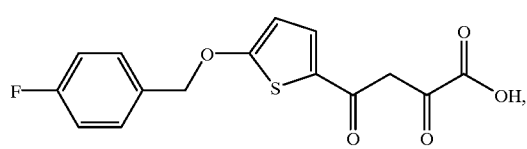
(5)
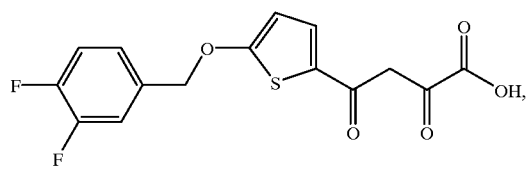
(6)
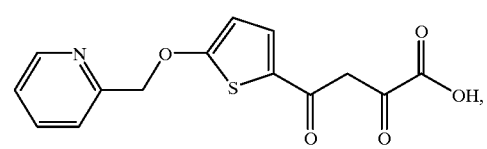
(7)
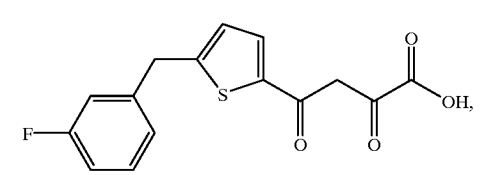
(8)
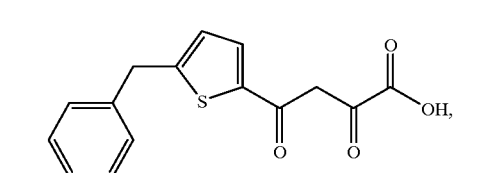
-continued
(9)
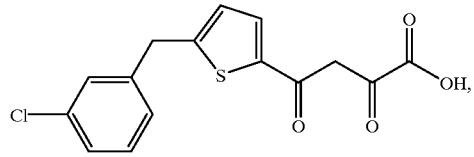
(10)
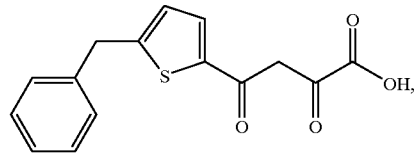
(11)
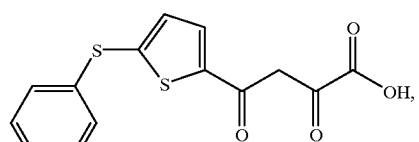
(12)
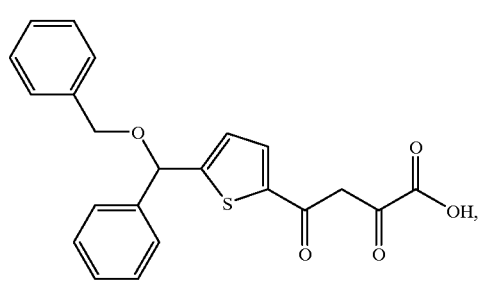
(13)
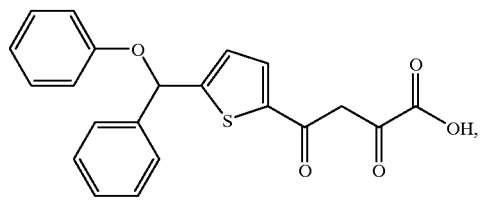
(14)
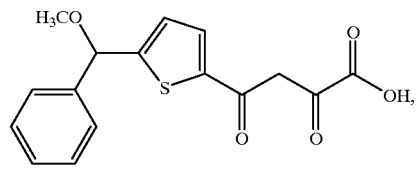
(15)
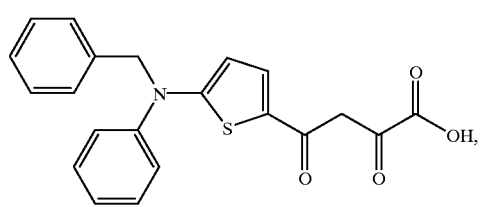

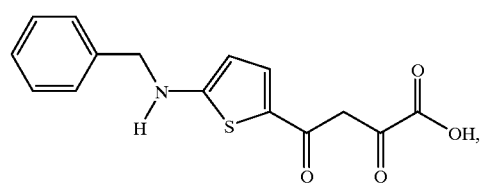
(16)
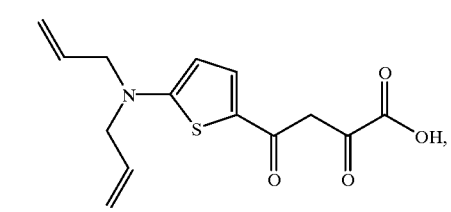
(17)
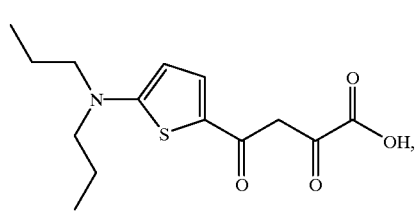
(18)
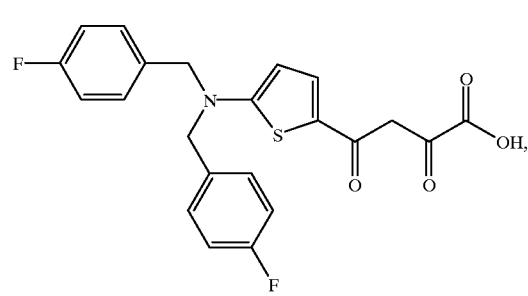
(19)
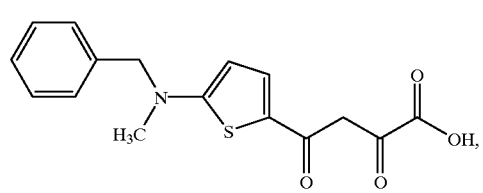
(20)
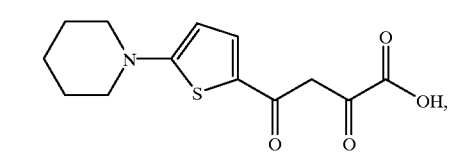
(21)
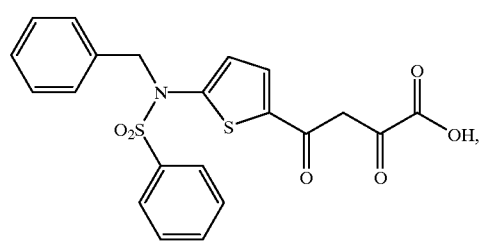
(22)
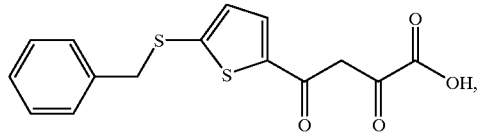
(23)
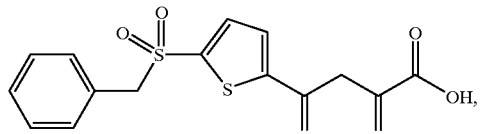
(24)
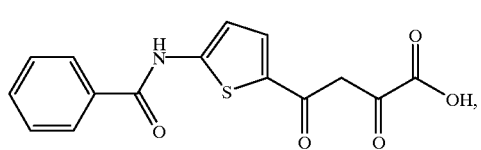
(25)
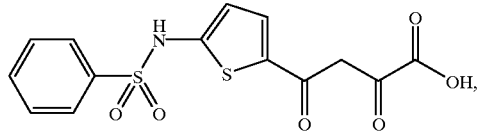
(26)
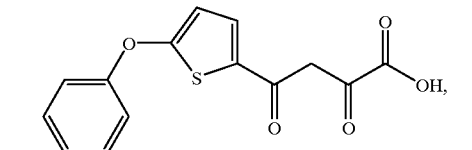
(27)
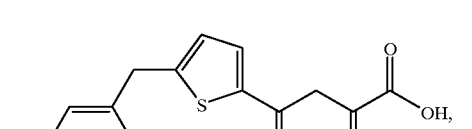
(28)
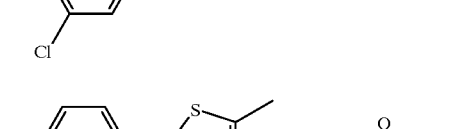
(29)
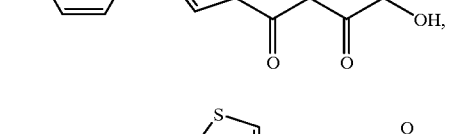
(30)
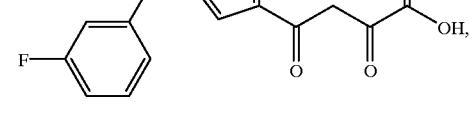
(31)

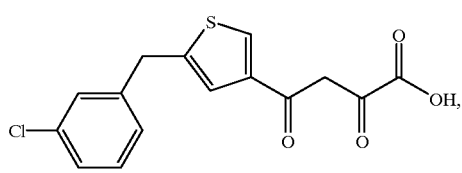
(32)
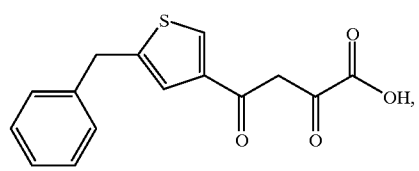
(33)
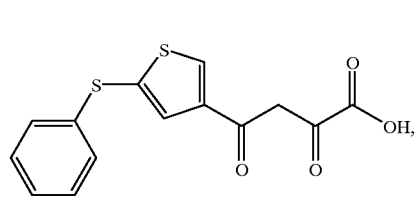
(34)
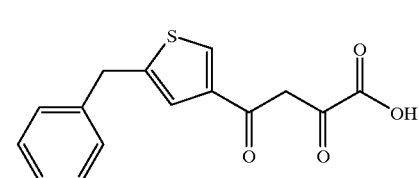
(35)
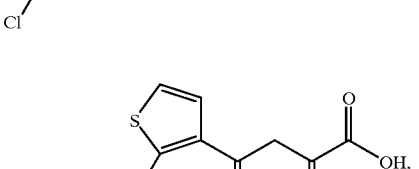
(36)
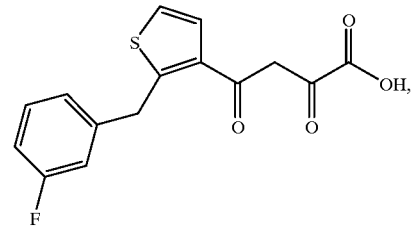
(37)
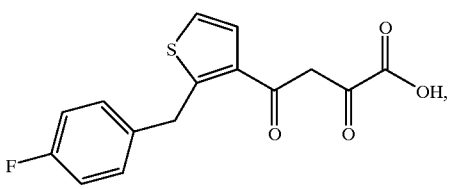
(38)
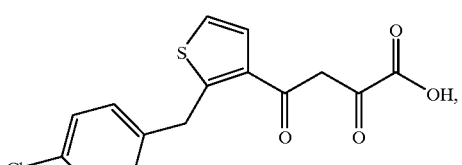
(39)
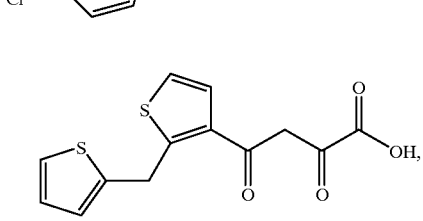
(40)
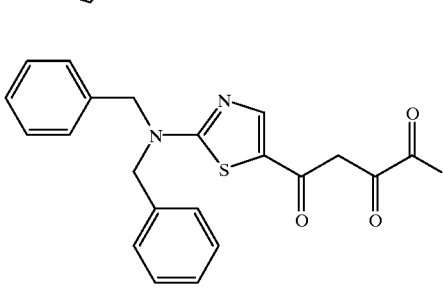
(41)
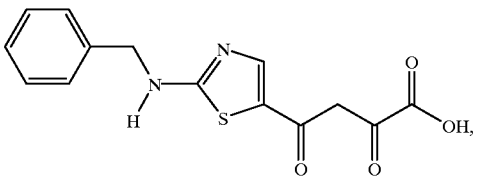
(42)
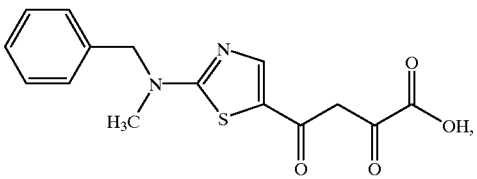
(43)
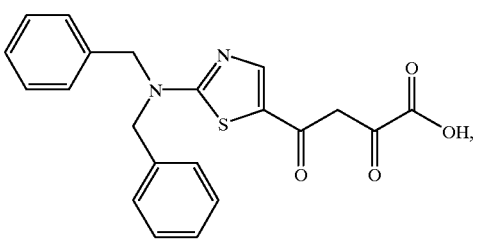
(44)
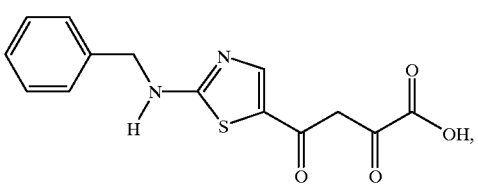
(45)

-continued (46), (47), (48), (49), (50), (51), (52), (53), (54), (55)

and tautomers and pharmaceutically acceptable salts thereof.

In one embodiment of the present invention, structural formula (I) is:

In another embodiment of the present invention, structural formula (I) is:

In still another embodiment of the present invention, structural formula (I) is:

In yet another embodiment of the present invention, structural formula (I) is;

In one class of compounds of the present invention, A is selected from:

(1) thienyl, (2) thiazolyl,

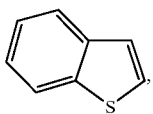
(3)

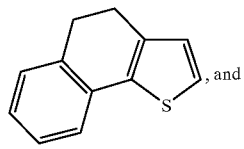
(4)
, and

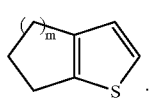
(5)

In another class of compounds of the present invention, A is selected from:
(1) thienyl,
(2) thiazolyl,

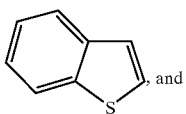
(3)
, and

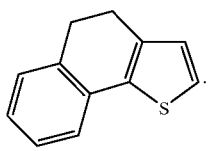
(4)

In one class of compounds of the present invention, $R^1$ is selected from:
(1) —H,
(2) —CH$_3$,
(3) —CF$_3$,
(4) -halo,
(5) —NO$_2$,
(6) —N(R$^4$)(R$^5$),
(7) -phenyl,
(8) substituted phenyl substituted with 1 or 2 substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(9) phenyl C$_{1-3}$ alkyl-,
(10) substituted phenyl C$_{1-3}$ alkyl-substituted with 1 or 2 substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(11) —C$_{2-5}$ alkenyl-R$^3$,
(12) —C$_{2-5}$ alkynyl-R$^3$, and
(13) —C(O)CH$_2$C(O)C(O)OR$^7$.

In another class of compounds of the present invention, $R^1$ is selected from:
(1) —H,
(2) —CH$_3$,
(3) —CF$_3$,
(4) -halo,
(5) —NO$_2$,
(6) —N(R$^4$)(R$^5$),
(7) -phenyl,
(8) substituted phenyl substituted with 1 or 2 substituents independently selected from:
(a) halo,
(b) methyl, and
(c) methoxy,
(9) phenyl C$_{1-3}$ alkyl-,
(10) substituted phenyl C$_{1-3}$ alkyl-substituted with 1 or 2 substituents independently selected from:
(a) halo,
(b) methyl, and
(c) methoxy, and
(11) —C$_{2-5}$ alkenyl-R$^3$.

In still another class of compounds of the present invention, $R^1$ is hydrogen.

In one class of compounds of the present invention, $R^2$ is selected from:
(1) —H,
(2) —R$^3$,
(3) —C$_{1-6}$ alkyl,
(4) —C$_{1-6}$ alkyl substituted with R$^3$,
(5) —O—R$^6$,
(6) —O—C$_{1-6}$ alkyl-OR$^6$,
(7) —S(O)n—R$^6$,
(8) —C$_{1-6}$ alkyl (OR$^6$)(R$^4$),
(9) —C$_{1-6}$ alkyl (OR$^4$)(R$^6$),
(10) —C$_{0-6}$ alkyl-N(R$^4$)(R$^6$,
(11) —C$_{1-6}$ alkyl S(O)n—R$^6$,
(12) —C$_{0-6}$ alkyl C(O)—R$^6$,
(13) —C$_{0-6}$ alkyl C(S)—R$^6$,
(14) —C$_{0-6}$ alkyl NR$^4$C(O)—R$^6$, and
(15) —C$_{0-6}$ alkyl-C(O)N(R$^4$)(R$^5$).

In another class of compounds of the present invention, $R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —S(O)n—$R^6$,
(7) —$C_{1-6}$ alkyl (O$R^6$)($R^4$),
(8) —$C_{1-6}$ alkyl (O$R^4$)($R^6$),
(9) —$C_{0-6}$ alkyl-N($R^4$)($R^6$),
(10) —$C_{1-6}$ alkyl S(O)n—$R^6$,
(11) —$C_{0-6}$ alkyl C(O)—$R^6$,
(12) —$C_{0-6}$ alkyl N$R^4$C(O)—$R^6$, and
(13) —$C_{0-6}$ alkyl-C(O)N($R^4$)($R^5$).

In one class of compounds of the present invention, $R^3$ is selected from:
(1) phenyl;
(2) substituted phenyl with 1, 2, or 3 substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(3) thienyl;
(4) substituted thienyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(5) pyridyl;
(6) substituted pyridyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(7) imidazolyl;
(8) substituted imidazolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(9) pyrrolyl;
(10) substituted pyrrolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(11) pyrazolyl;
(12) substituted pyrazolyl substituted on a carbon atom with one or two substituents independently selected from:
  (a) halogen,
  (b) $C_{1-6}$ alkyl,
  (c) $C_{1-6}$ alkyloxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen,
    (ii) $C_{1-6}$ alkyl,
    (iii) —$CF_3$, and
    (iv) hydroxy;
(13) $C_{3-6}$ cycloalkyl;
(14) substituted $C_{3-6}$ cycloalkyl with 1 or 2 substituents independently selected from:

(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;

(15) piperidinyl;
(16) substituted piperidinyl substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;

(17) morpholinyl;
(18) substituted morpholinyl substituted at a carbon or nitrogen atom with 1 or 2 independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;

(19) naphthyl,
(20) substituted naphthyl with 1, 2, or 3 substituents independently selected from:
(a) -halogen,
(b) —$C_{1-6}$ alkyl,
(c) —$C_{1-6}$ alkyloxy-,
(d) —$CF_3$,
(e) —$OCF_3$,
(f) —CN, and
(g) -hydroxy;

(21) indolyl;
(22) substituted indolyl substituted on a carbon atom with one or two substituents independently selected from:
(a) -halogen,
(b) —$C_{1-6}$ alkyl,
(c) —$C_{1-6}$ alkyloxy-,
(d) —$CF_3$,
(e) —$OCF_3$,
(f) —CN, and
(g) -hydroxy;

(23) $C_{3-6}$ cycloalkyl fused with a phenyl ring
(24) substituted $C_{3-6}$ cycloalkyl fused with a phenyl ring substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy.

In another class of compounds of the present invention, $R^3$ is selected from:

(1) phenyl;
(2) substituted phenyl with 1, 2, or 3 substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;

(3) thienyl;
(4) substituted thienyl substituted on a carbon atom with one or two substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;

(5) pyridyl;
(6) substituted pyridyl substituted on a carbon atom with one or two substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;

(7) imidazolyl;
(8) pyrrolyl;
(9) pyrazolyl;
(10) $C_{3-6}$ cycloalkyl,
(11) substituted $C_{3-6}$ cycloalkyl with 1 or 2 substituents independently selected from:
(a) halogen,
(b) $C_{1-6}$ alkyl,
(c) $C_{1-6}$ alkyloxy-,
(d) —$CF_3$,
(e) —$OCF_3$, (f) —CN,
(g) =O, and
(h) hydroxy;
(12) piperidinyl;
(13) substituted piperidinyl substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(14) morpholinyl;
(15) naphthyl;
(16) indolyl, and
(17) $C_{3-6}$ cycloalkyl fused with a phenyl ring.

In still another class of compounds of the present invention, $R^3$ is selected from:
(1) phenyl,
(2) substituted phenyl with 1, 2, or 3 substituents independently selected from:
(a) halogen selected from —F, —Cl, —Br,
(b) $CH_3$,
(c) methoxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen selected from —F, —Cl, —Br,
(ii) —$CH_3$,
(iii) —$CF_3$, and
(iv) hydroxy;
(3) thienyl,
(5) pyridyl,
(7) imidazolyl,
(8) pyrrolyl,
(9) pyrazolyl,
(10) $C_{1-6}$ cycloalkyl,
(12) piperidinyl,
(14) morpholinyl,
(15) naphthyl,
(16) indolyl, and
(17) $C_{1-6}$ cycloalkyl fused with a phenyl ring.

In one class of compounds of the present invention, $R^4$ is selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —C(O)—$R^3$.

In another class of compounds of the present invention, $R^4$ is selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$, and
(7) —$S(O)_n$—$R^3$.

In one class of compounds of the present invention, $R^5$ is selected from:
(1) —H,
(2) —$C_{1-3}$ alkyl,
(3) —$CF_3$,
(4) —$R^3$
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —C(O)—$R^3$, In another class of compounds of the present invention, $R^5$ is selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$, and
(8) —$S(O)_n$—$R^3$.

In one class of compounds of the present invention, $R^7$ is hydrogen.

In one class of compounds of the present invention, $R^8$ is selected from: hydrogen, methyl and methoxy.

Also included within the present invention are pharmaceutical compositions useful for inhibiting HIV integrase, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. Additionally, the present invention is directed to a pharmaceutical composition comprising a therapeutically effective amount of a compound of the present invention in combination with a therapeutically effective amount of an AIDS treatment agent selected from:
(1) an AIDS antiviral agent,
(2) an anti-infective agent, and
(3) an immunomodulator.

The compounds of the present invention may have asymmetric centers and may occur, except when specifically noted, as mixtures of stereoisomers or as individual diastereomers, or enantiomers, with all isomeric forms being included in the present invention.

As is recognized by one of ordinary skill in the art, the diketo-acid/ester compounds of the present invention exist as tautomers, and thus by using the phrase "and tautomers thereof" in describing compounds of structural formula (I), Applicants also intend the following tautomeric forms of the same compound (Ia) and (Ib):

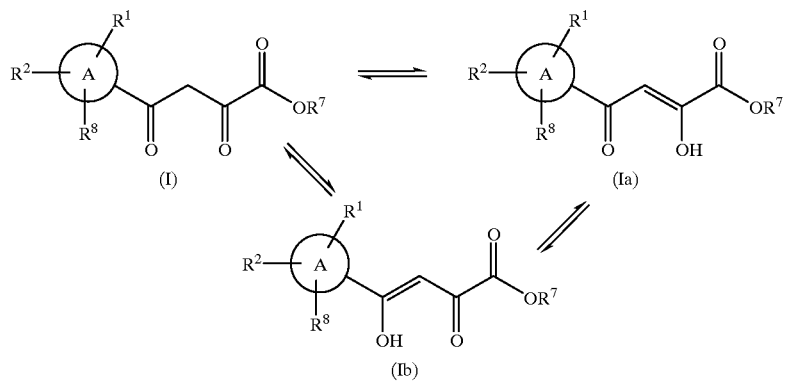

By naming or referring to compound (I) and tautomers thereof, it is understood for the purposes of the present application that the tautomers (Ia) and (Ib) are also intended. Similarly, by referring to compound (Ia), it is understood for the purposes of the present application that the tautomers (I) and (Ib) are also intended. The same holds true for references to tautomer (Ib).

When any variable (e.g., $R^3$, $R^4$, etc.) occurs more than one time in any constituent or in formula I, its definition on each occurrence is independent of its definition at every other occurrence. Also, combinations of substituents and/or variables are permissible only if such combinations result in stable compounds.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The present invention also provides for the use of a compound of structural formula (I) to make a pharmaceutical composition useful for inhibiting HIV integrase and in the treatment of AIDS or ARC.

Compounds of structural formula (I) wherein A is thienyl may be made according to the procedures in Schemes AI, AII, BI, CI, CII, DI, EI, FI, FII, and FIII. Compounds of structural formula (I) wherein A is thiazolyl may be prepared according to the procedures in Scheme GI.

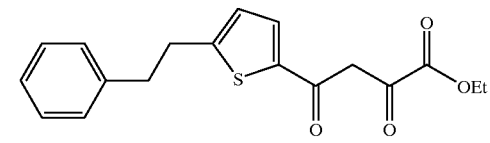

AI(3)

i. NaOH, MeOH—H$_2$O-THF
ii. HCl

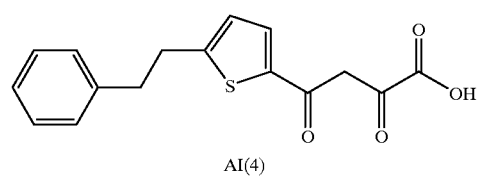

AI(4)

Scheme AII

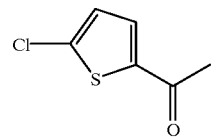

AII(1)

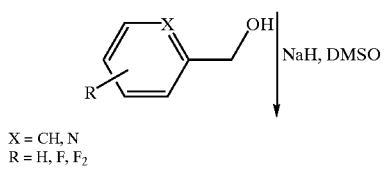

X = CH, N
R = H, F, F$_2$

AII(2a-e)

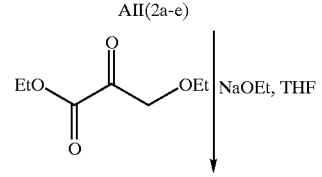

NaOEt, THF

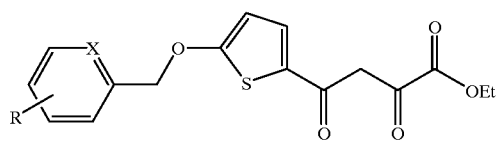
AII(3a-e)
i. NaOH, MeOH—H$_2$O-THF
ii. HCl
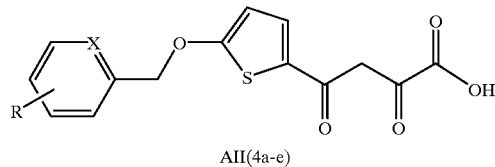
AII(4a-e)
Scheme BI
BI (1)
n-BuLi, Et$_2$O,
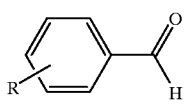
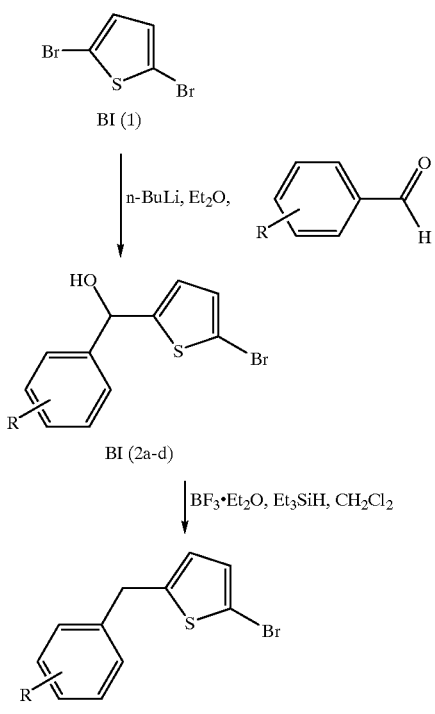
BI (2a-d)
BF$_3$·Et$_2$O, Et$_3$SiH, CH$_2$Cl$_2$
BI(3a-d)
n-BuLi, Et$_2$O, CH$_3$CONCH$_3$(OCH$_3$)
BI(4a-d)
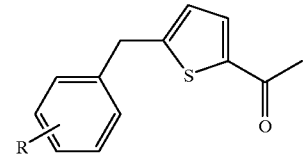 LDA, THF
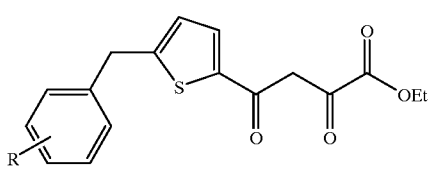
BI(5a-d)
i. NaOH, MeOH—H$_2$O-THF
ii. HCl
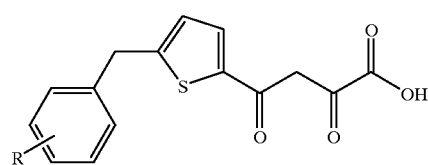
BI(6a-d)
Scheme BII
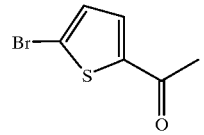
BII(1)
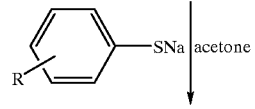 acetone
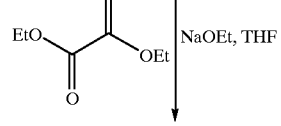
BII(2)
EtO–C(O)–C(O)–OEt   NaOEt, THF
BII(3)
i. NaOH, MeOH—H$_2$O-THF
ii. HCl

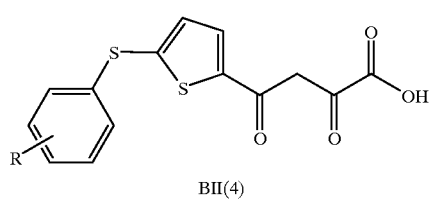
BII(4)
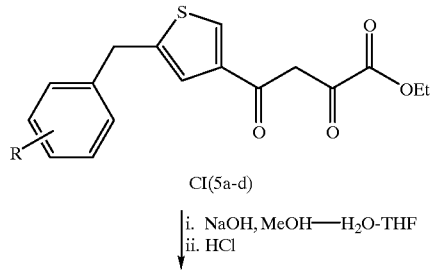
CI(5a-d)
i. NaOH, MeOH—H₂O-THF
ii. HCl
Scheme CI
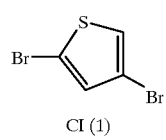
CI (1)
| n-BuLi, Et₂O,
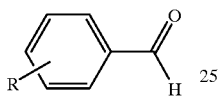
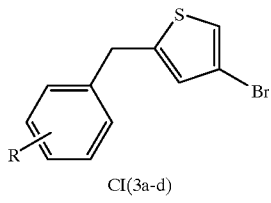
CI(6a-d)
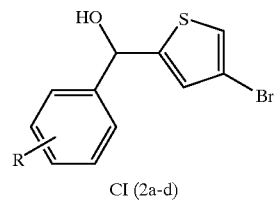
CI (2a-d)
| BF₃·Et₂O, Et₃SiH(xs), CH₂Cl₂
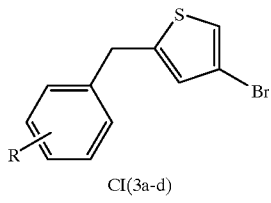
CI(3a-d)
| n-BuLi, Et₂O, CH₃CONCH₃(OCH₃)
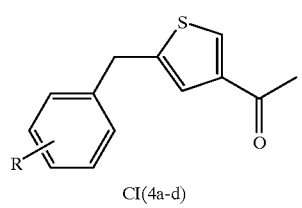
CI(4a-d)
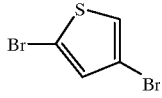
| LDA, THF
Scheme CII
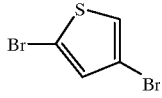
CI (1)
| n-BuLi, Et₂O,
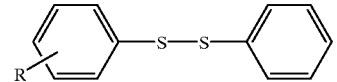
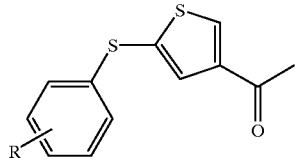
CII (1)
| n-BuLi, Et₂O, CH₃CONCH₃(OCH₃)
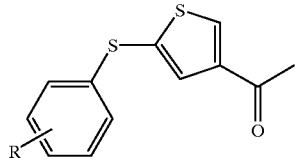
CII (2)
| LDA, THF

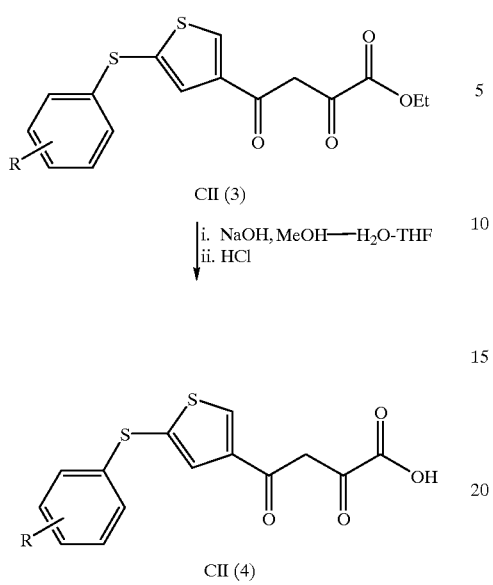
CII (3)
i. NaOH, MeOH—H₂O-THF
ii. HCl
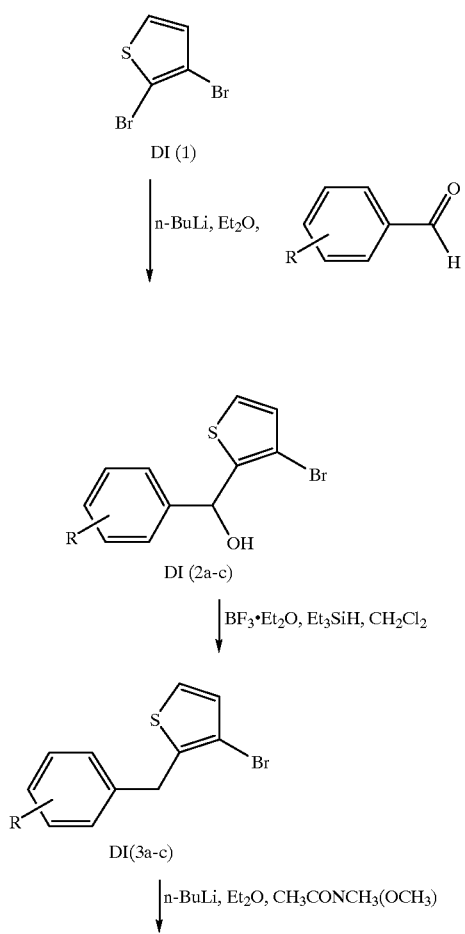
CII (4)
Scheme DI
DI (1)
n-BuLi, Et₂O,
DI (2a-c)
BF₃·Et₂O, Et₃SiH, CH₂Cl₂
DI(3a-c)
n-BuLi, Et₂O, CH₃CONCH₃(OCH₃)
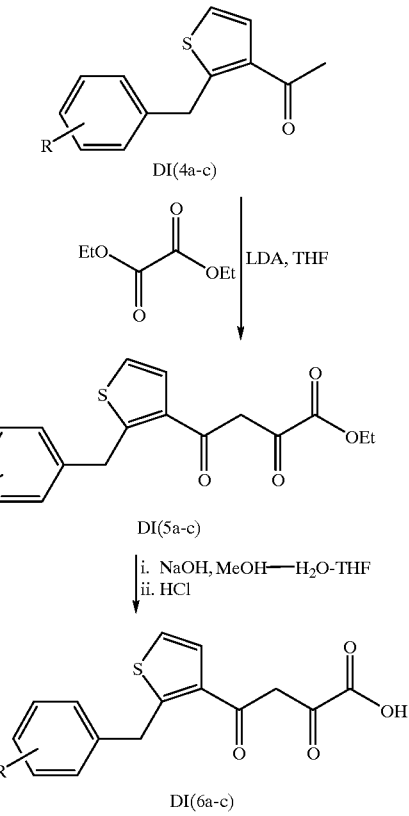
DI(4a-c)
LDA, THF
DI(5a-c)
i. NaOH, MeOH—H₂O-THF
ii. HCl
DI(6a-c)
Scheme EI
BI (1)
n-BuLi, Et₂O,
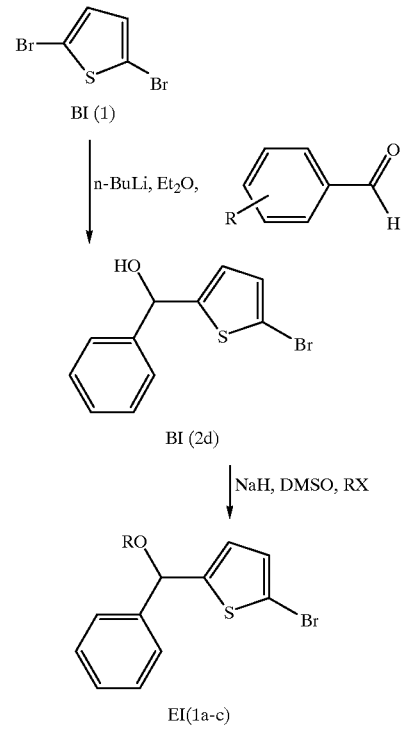
BI (2d)
NaH, DMSO, RX
EI(1a-c)
R = Bn, Ph, Me

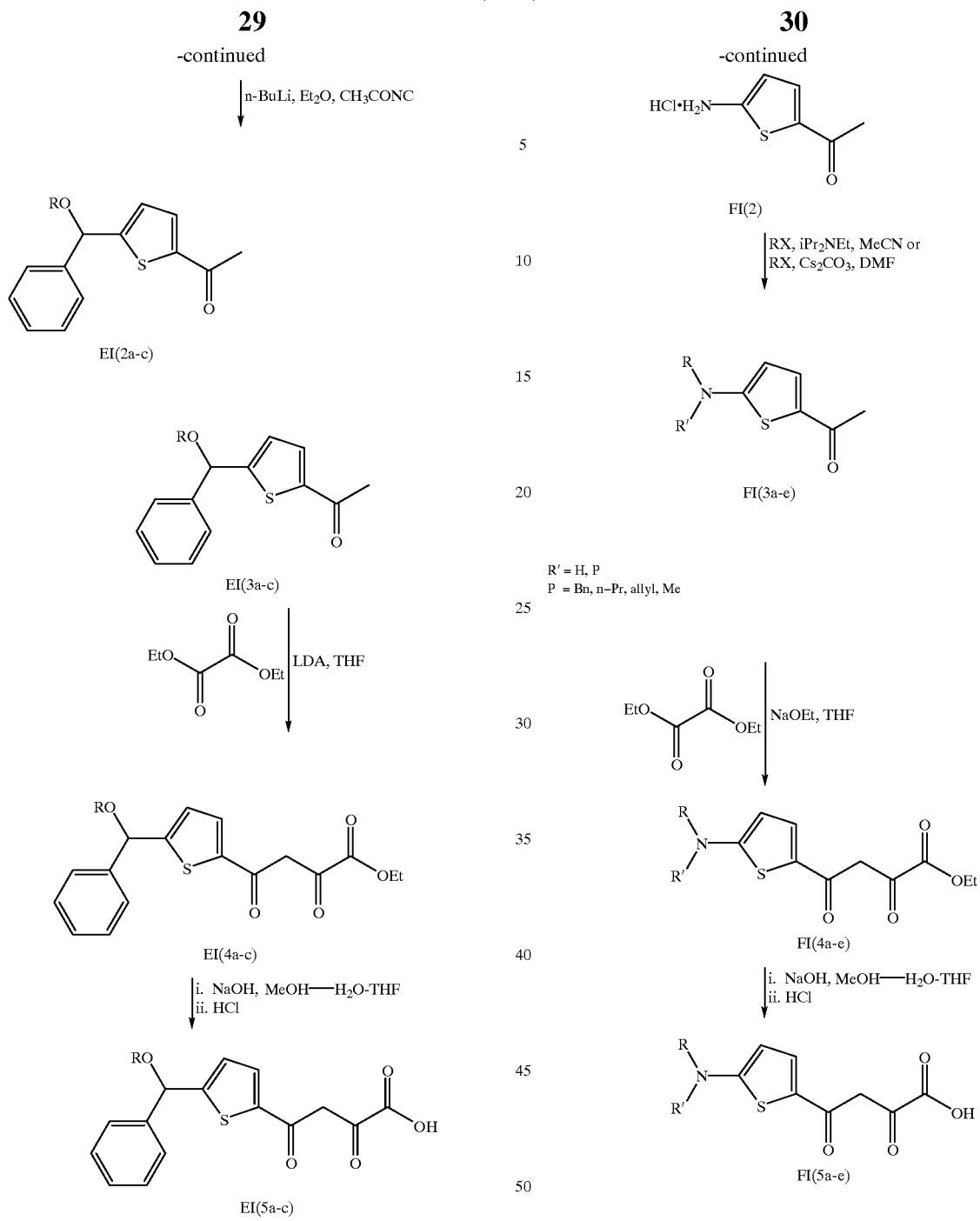
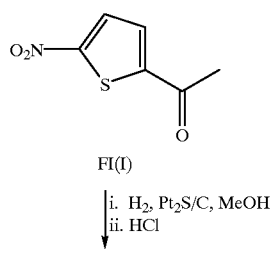
Scheme FI
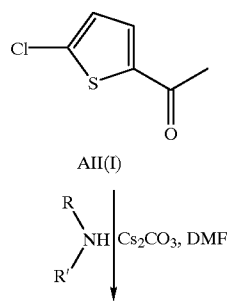
Scheme FII

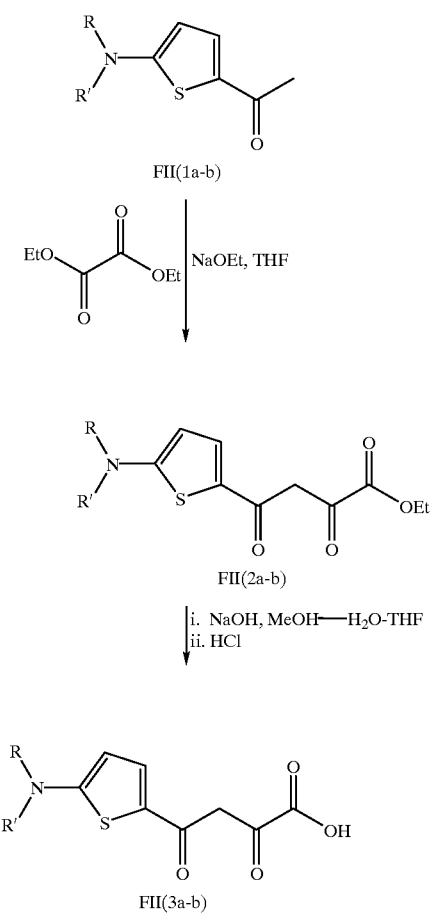
FII(1a-b)
FII(2a-b)
i. NaOH, MeOH—H₂O-THF
ii. HCl
FII(3a-b)
Scheme FIII
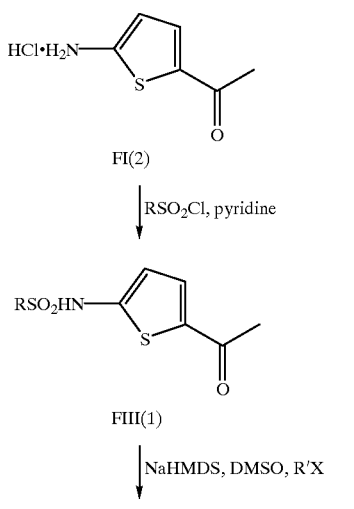
FI(2)
RSO₂Cl, pyridine
FIII(1)
NaHMDS, DMSO, R'X
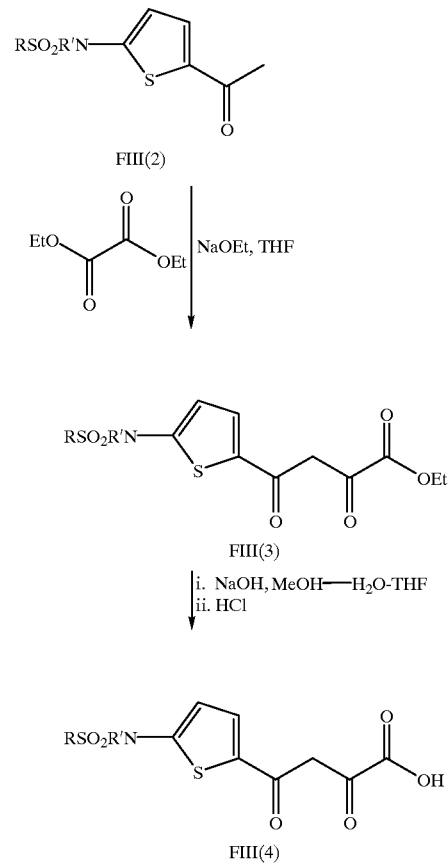
FIII(2)
FIII(3)
i. NaOH, MeOH—H₂O-THF
ii. HCl
FIII(4)
Scheme GI
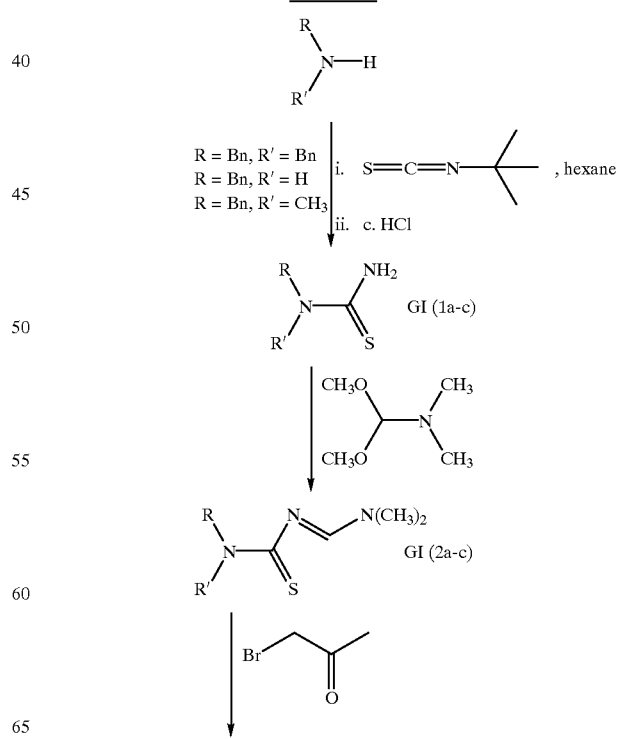
R = Bn, R' = Bn
R = Bn, R' = H
R = Bn, R' = CH₃
i. S=C=N—tBu, hexane
ii. c. HCl
GI (1a-c)
GI (2a-c)

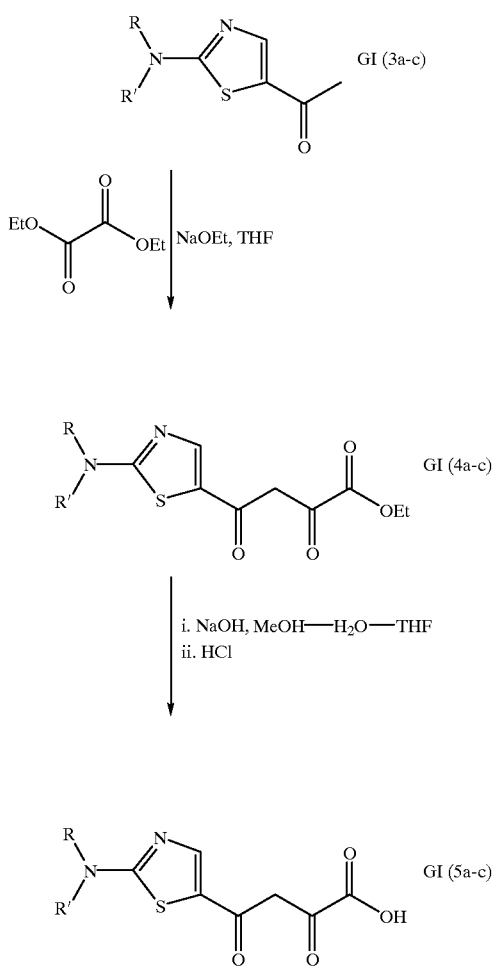

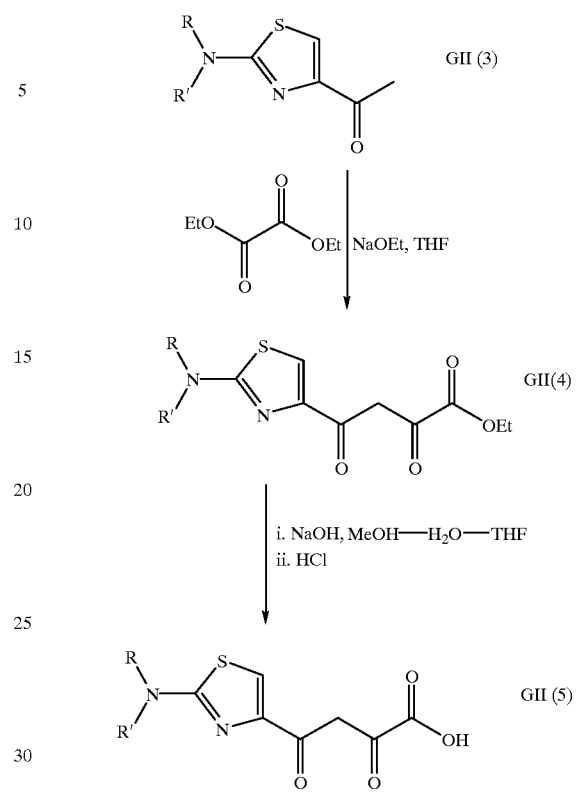

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine,

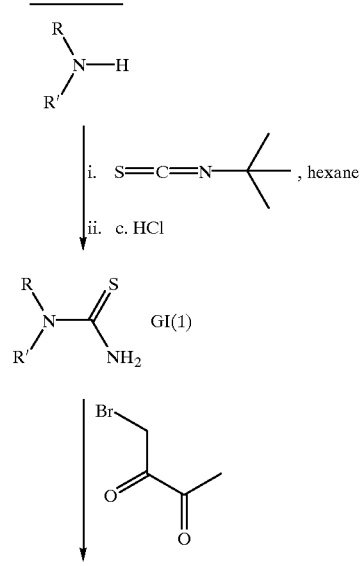

chloroprocaine, diethanolamine, procaine, N-benzylphenethyl-amine, diethylamine, piperazine, tris(hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The terms "administration of" and or "administering a" compound should be understood to mean providing a compound of the invention or a prodrug of a compound of the invention to the individual in need of treatment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results, directly or indirectly, from combination of the specified ingredients in the specified amounts.

By "pharmaceutically acceptable" it is meant the carrier, diluent or excipient must be compatible with the other ingredients of the formulation and not deleterious to the recipient thereof.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

| ANTIVIRALS | | |
|---|---|---|
| Drug Name | Manufacturer | Indication |
| 097 | Hoechst/Bayer | HIV infection, AIDS, ARC (non-nucleoside reverse transcriptase (RT) inhibitor) |
| Amprenivir 141 W94 GW141 | Glaxo Wellcome | HIV infection, AIDS, ARC (protease inhibitor) |
| Abacavir (1592U89) | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |

-continued

ANTIVIRALS

| Drug Name | Manufacturer | Indication |
|---|---|---|
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Sqiubb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) ((-) 6-Chloro-4(S)-cyclopropylethynyl-4(S)-trifluoro-methyl-1,4-dihydro-2H-3,1-benzoxazin-2-one) STOCRIN, | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS, |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

| IMMUNO-MODULATORS | | |
|---|---|---|
| Drug Name | Manufacturer | Indication |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

| ANTI-INFECTIVES | | |
|---|---|---|
| Drug Name | Manufacturer | Indication |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

| OTHER | | |
|---|---|---|
| Drug Name | Manufacturer | Indication |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2 (S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Indinavir is an inhibitor of HIV protease and is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day.

The following examples are provided to further illustrate details for the perparation and use of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variatioons of the conditions and processes of the following preparative procedures can be used to prepare these compounds. All temperatures are in degrees Celsius unless noted otherwise.

Abbreviations: aq is aqueous; Ac represents acetyl; ACN is acetonitrile; Bn represents benzyl; DMF is dimethyl formamide; DMSO is dimethyl sulfoxide; Et represents ethyl; IPA is isopropyl alcohol; Me represents methyl; NaHMDS represents sodium hexamethyl disilamide; rt, RT both represent room temperature; sat represents saturated; THF is tetrahydrofuran; TLC is thin layer ($SiO_2$) chromatography.

EXAMPLE 1

2,4-dioxo-4-(5-phenethylthiophen-2-yl)butanoic acid

Step A:
Preparation of ethyl 2,4-dioxo-4-(5-phenethynylthiophen-2-yl)butanoate AI(2)

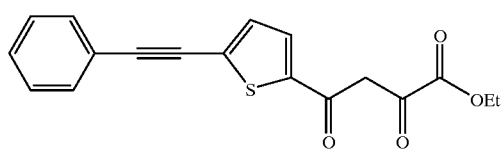

A mixture of 2-acetyl-5-(phenylethynyl)thiophene (1.81 g, 8.02 mmol), diethyl oxalate (2.17 mL, 16 mmol), and sodium ethoxide (1.09 g, 16 mmol) in anhydrous THF (25 mL) was stirred at rt under an atmosphere of argon for 5 hr. The resultant mixture was diluted with dichloromethane, and washed successively with dilute HCl, and brine. The organic extract was dried over anhydrous magnesium sulfate, filtered, and concentrated under vacuum to provide yellow solid. Recrystallization of the solid from a mixture dichloromethane and hexane provided the title compound.

Step B:
Preparation of ethyl 2,4-dioxo-4-(5-phenethylthiophen-2-yl)butanoate AI(3)

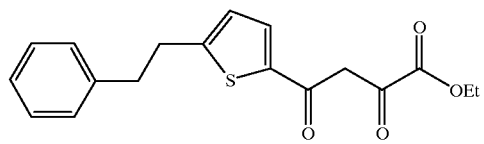

A mixture of ethyl 2,4-dioxo-4-(5-phenethynylthiophen-2-yl)butanoate (195 mg, 0.597 mmol), 10% Pd/C (95 mg), and THF (5 mL) in absolute ethanol (40 mL) was stirred under a balloon of hydrogen for 2 h. The resulting mixture was filtered through a pad of Celite™, diatomaceous earth. The filtrate was concentrated under vacuum to provide the title compound.

Step C:
Preparation of 2,4-dioxo-4-(5-phenethylthiophen-2-yl)butanoic acid AI(4)

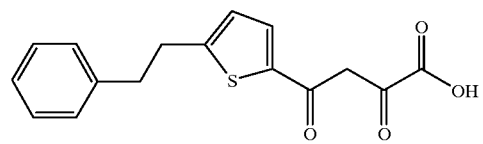

A solution of ethyl 2,4-dioxo-4-(5-phenethylthiophen-2-yl)butanoate (125 mg, 0.378 mmol), aqueous sodium hydroxide (1.2 mL, 1M, 1.2 mmol), and THF (5 mL) in methanol (5 mL) was stirred at rt overnight. The resultant mixture was treated with aq HCl (1.3 mL. 1M), and concentrated under vacuum. The residue was partitioned between brine and dichloromethane. The organic extract was dried over anhydrous magnesium sulfate, filtered, and concentrated under vacuum to provide off-white solid. Recrystallization of the solid from a mixture dichloromethane and hexane provided the title compound. $^1$H NMR ($CDCl_3$) δ 7.72 (d, J=3.1 Hz, 1H), 7.35–7.15 (m, 5H), 6.94 (s, 1H), 6.86 (d, J=3.1 Hz, 1H), 3.22 (d, J=8.1 Hz, 2H), 3.03 (d, J=8.1 Hz, 2H).

EXAMPLE 2

2,4-dioxo-4-(5-benzyloxythiophen-2-yl)butanoic acid

Step A:
Preparation of 2-acetyl-5-(benzyloxy)thiophene AII(2a)

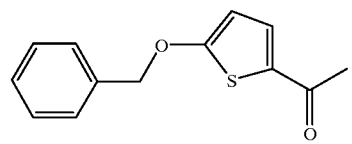

A suspension of sodium hydride (538 mg, 22.4 mmol) in anhydrous DMSO (30 mL) was stirred at 60° C. under an atmosphere of argon for 1 hr. The resultant mixture was cooled to rt, benzyl alcohol (2.32 mL, 22.40 mmol) and 2-acetyl-5-chlorothiophene (3.01 g, 18.74 mmol) was added. The mixture was heated under an atmosphere of argon at 85° C. overnight. The product mixture was concentrated under vacuum, and the residue partitioned between ethyl acetate and dilute aqueous HCl. The organic extract was washed with brine, dried over anhydrous magnesium sulfate, filtered and concentrated under vacuum. The residue was subjected to column chromatography on silica gel eluting with 3% methanol in chloroform. Collection and concentration of appropriate fractions provided the title ketone.

Step B:

Preparation of 2,4-dioxo-4-(5-benzyloxythiophen-2-yl) butanoic acid AII(4a)

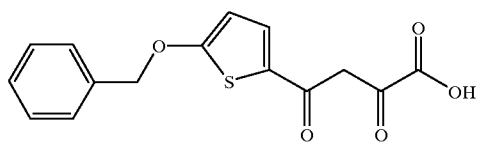

The title compound was prepared using the protocol described in Example AI(4), Step A and C substituting 2-acetyl-5-(phenylethynyl)-thiophene with 2-acetyl-5-(benzyloxy)thiophene in Step A. $^1$H NMR (CDCl$_3$) δ 7.75 (d, J=4.6 Hz, 1H), 7.5–7.3 (m, 5H), 6.85 (s, 1H), 6.42 (d, J=4.6 Hz, 1H), 5.21 (s, 2H).

EXAMPLE 3

2,4-dioxo-4-[5-(3-fluorobenzyloxy)thiophen-2-yl] butanoic acid

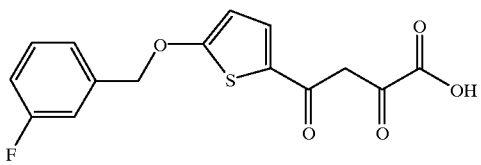

The title compound was prepared using the protocol described in Example AII(4a), Step A–B substituting benzyl alcohol with 3-fluorobenzyl alcohol in Step A. $^1$H NMR (DMSO-d$_6$) δ 8.0 (br s 1H), 7.5–7.15 (m, 4H), 6.85 (brs, 1H), 6.6 (br s, 1H), 5.3 (br s, 2H).

EXAMPLE 4

2,4-dioxo-4-[5-(4-fluorobenzyloxy)thiophen-2-yl] butanoic acid

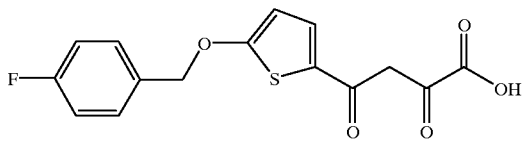

The title compound was prepared using the protocol described in Example AII(4a), Step A–B substituting benzyl alcohol with 4-fluorobenzyl alcohol in Step A. $^1$H NMR (DMSO-d$_6$) δ 8.0 (br s 1H), 7.54 (m, 2H), 7.25 (m, 2H), 6.85 (brs, 1H), 6.6 (br s, 1H), 5.3 (br s, 2H).

EXAMPLE 5

2,4-dioxo-4-[5-(3,4-difluorobenzyloxy)thiophen-2-yl]butanoic acid

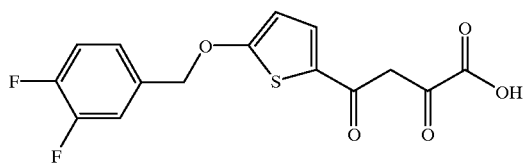

The title compound was prepared using the protocol described in Example AII(4a), Step A–B substituting benzyl alcohol with 3,4-difluorobenzyl alcohol in Step A. $^1$H NMR (CD$_3$OD) δ 7.79 (d, J=4.4 Hz, 1H), 7.45–7.25 (m, 3H), 6.92 (s, 1H), 6.53 (d, J=4.4 Hz, 1H), 5.24 (s, 2H).

EXAMPLE 6

2,4-dioxo-4-[5-(pyridin-2-ylmethyloxy)thiophen-2-yl]butanoic acid

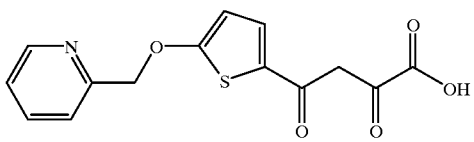

The title compound was prepared using the protocol described in Example AII(4a), Step A–B substituting benzyl alcohol with 2-pyridylcarbinol in Step A. $^1$H NMR (DMSO-d$_6$) δ 8.60 (d, J=4.6 Hz, 1H), 8.07 (d, J=4.6 Hz, 1H), 7.87 (ddd, J=7.7, 7.7, 1.7 Hz, 1H), 7.56 (d, J=7.7 Hz, 1H), 7.40 (dd, J=7.7, 4.7 Hz, 1H), 6.95 (s, 1H), 6.67 (d, J=4.6 Hz, 1H), 5.39 (s, 2H).

EXAMPLE 7

2,4-dioxo-4-[5-(3-fluorobenzyl)thiophen-2-yl] butanoic acid

Step A:

Preparation of (5-bromothiophen-2-yl)-(3-fluorophenyl) methanol BI(2a)

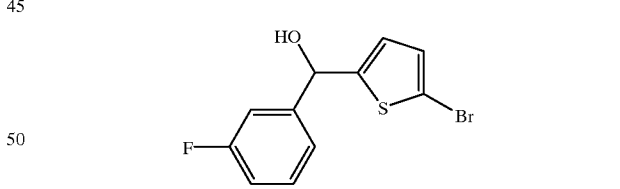

To a cold (−78° C.) solution of n-butyl lithium (20.8 mL, 2.5 M in hexane, 52 mmol) in anhydrous diethyl ether (100 mL) under an atmosphere of argon, 2,5-dibromothiophene (5.63 mL, 50 mmol) was added dropwise over a period of 30 min. After the reaction mixture was stirred at −78° C. for an additional 90 min, 3-fluorobenzaldehyde (5.5 mL, 52 mmol) was added over a period of 15 min. The resultant mixture was allowed to warm to rt over a period of 2.5 h. The resultant solution was diluted with dichloromethane, and neutralized with dilute HCl. The organic extract was washed with brine, dried over anhydrous magnesium sulfate, filtered, and concentrated under vacuum to provide the title compound as brown oil. The oil was used in the following step without further purification.

Step B:
Preparation of 2-bromo-5-(3-fluorobenzyl)thiophene BI(3a)

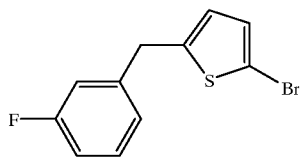

To a cold (0° C.) solution of (5-bromothiophen-2-yl)-(3-fluorophenyl)-methanol (4.35 g, 15.2 mmol) and triethylsilane (3.60 mL, 22.7 mmol) in dichloromethane (30 mL), boron trifluoride etherate (2.90 mL, 22.9 mmol) was added. The resultant mixture was stirred at rt for 3 h, and treated with sat. aq. sodium bicarbonate. The organic extract was washed with brine, dried over anhydrous magnesium sulfate, filtered, and concentrated under vacuum. The residue was subjected to column chromatography on silica gel eluting with hexane. Collection and concentration of appropriate fractions provide the title compound as clear colorless oil. The product was stored under argon in a freezer.

Step C:
Preparation of 2-acetyl-5-(3-fluorobenzyl)thiophene BI(4a)

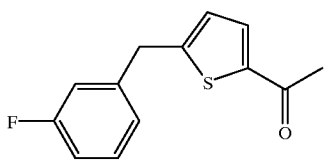

To a cold (−78° C.) solution of 2-bromo-5-(3-fluorobenzyl)thiophene (2.0 g, 7.38 mmol) in anhydrous diethyl ether (20 mL) under an atmosphere of argon, n-butyl lithium (4.8 mL, 1.6 M in hexane, 7.68 mmol) was added dropwise over a period of 15 min. After the reaction mixture was stirred at −78° C. for an additional 1 h, N-methoxy-N-methylacetamide (0.91 mL, 8.86 mmol) was added over a period of 10 min. The resultant mixture was allowed to warm to rt and stirred overnight. The resultant solution was diluted with ether, and neutralized with dilute HCl. The organic extract was washed with brine, dried over anhydrous magnesium sulfate, filtered, and concentrated under vacuum. The residue was subjected to column chromatography on silica gel eluting with 20% ethyl acetate in hexane. Collection and concentration of appropriate fractions provide the title compound as clear pale yellow oil.

Step D:
Preparation of ethyl 2,4-dioxo-4-[5-(3-fluorobenzyl)thiophen-2-yl]butanoate BI(5a)

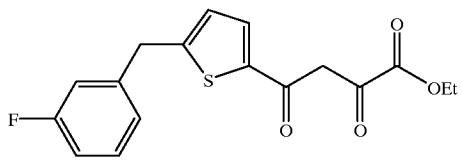

To a cold (−78° C.) solution of 2-acetyl-5-(3-fluorobenzyl)thiophene (315 mg, 1.34 mmol) in anhydrous THF (5 mL) under an atmosphere of argon, LDA (0.7 mL, 2 M in a mixture of heptane, THF and ethylbenzene, 1.40 mmol) was added dropwise over a period of 10 min. After the reaction mixture was stirred at −78° C. for an additional 40 min, diethyl oxalate (0.26 mL, 1.91 mmol) was added over a period of 5 min. The resultant mixture was allowed to warm to rt and stirred overnight. The resultant solution was diluted with ethyl acetate, and neutralized with dilute HCl. The organic extract was washed with brine, dried over anhydrous magnesium sulfate, filtered, and concentrated under vacuum. The residue was triturated with hexane. The precipitate was filtered to provide the title compound as yellow solid.

Step E:
Preparation of 2,4-dioxo-4-[5-(3-fluorobenzyl)thiophen-2-yl]butanoic acid BI(6a)

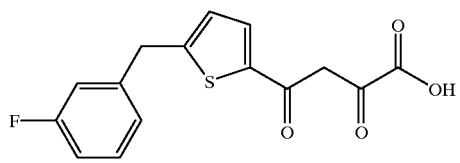

The title compound was prepared using the protocol described in Example AI(4), Step C substituting ethyl 2,4-dioxo-4-(5-phenethylthiophen-2-yl)butanoate with ethyl 2,4-dioxo-4-[5-(3-fluorobenzyl)thiophen-2-yl]butanoate. The product was recrystallized from a mixture of ether and hexane. $^1$H NMR (CDCl$_3$) δ 7.75 (d, J=4.1 Hz, 1H), 7.35–7.25 (m, 2H), 7.05–6.90 (m, 4H), 4.20 (s, 2H).

EXAMPLE 8

2,4-dioxo-4-[5-(4-fluorobenzyl)thiophen-2-yl] butanoic acid

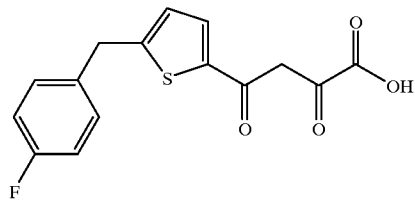

The title compound was prepared using the protocol described in Example BI(6a), Step A–E substituting 3-fluorobenzaldehyde with 4-fluoro-benzaldehyde in Step A. $^1$H NMR (CDCl$_3$) δ 7.74 (d, J=3.8 Hz, 1H), 7.21 (m, 2H), 7.03 (m, 2H), 6.91 (m, 2H), 4.18 (s, 2H).

EXAMPLE 9

2,4-dioxo-4-[5-(3-chlorobenzyl)thiophen-2-yl] butanoic acid

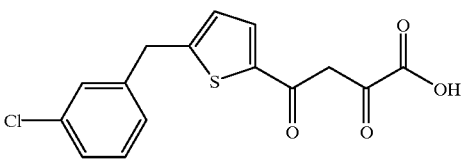

The title compound was prepared using the protocol described in Example BI(6a), Step A–E substituting 3-fluorobenzaldehyde with 3-chloro-benzaldehyde in Step A. $^1$H NMR (CDCl$_3$) δ 7.74 (d, J=4.0 Hz, 1H), 7.3–7.2 (m, 3H), 7.14 (m, 1H), 6.92 (m, 2H), 4.18 (s, 2H).

EXAMPLE 10

2,4-dioxo-4-(5-benzylthiophen-2-yl)butanoic acid

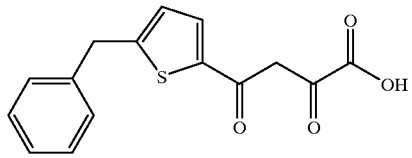

The title compound was prepared using the protocol described in Example BI(6a), Step A–E substituting 3-fluorobenzaldehyde with benzaldehyde in Step A. $^1$H NMR (CDCl$_3$) δ 7.74 (d, J=3.9 Hz, 1H), 7.38–7.22 (m, 5H), 6.91 (m, 2H), 4.21 (s, 2H).

EXAMPLE 11

2,4-dioxo-4-(5-phenylsulfanylthiophen-2-yl)butanoic acid

Step A:

Preparation of 2-acetyl-5-phenylsufanylthiophene BII(2)

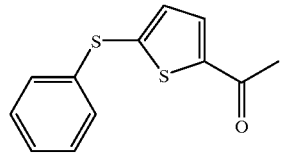

A mixture of thiophenol, sodium salt (718 mg, 5,43 mmol) and 2-acetyl-5-bromothiophene (1.0 g, 4.88 mmol) in acetone (10 mL) was stirred at rt under an atmosphere of argon overnight. The resultant mixture was concentrated under vacuum. The residue was subjected to column chromatography on silica gel eluting with chloroform. Collection and concentration of appropriate fractions provided the title ketone.

Step B:

Preparation of 2,4-dioxo-4-(5-phenylsulfanylthiophen-2-yl)butanoic acid BII(4)

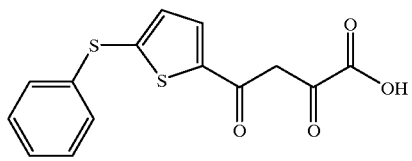

The title compound was prepared using the protocol described in Example AI(4), Step A and C substituting 2-acetyl-5-(phenylethynyl)-thiophene with 2-acetyl-5-phenylsufanylthiophene in Step A. The product was recrystallized from a mixture of ether and hexane. $^1$H NMR (CDCl$_3$) δ 7.73 (d, J=4.0 Hz, 1H), 7.48 (m, 2H), 7.38 (m, 3H), 7.08 (d, J=4.0 Hz, 1H), 6.88 (s, 1H).

EXAMPLE 12

2,4-dioxo-4-[5-(3-fluorobenzyl)thiophen-3-yl]butanoic acid

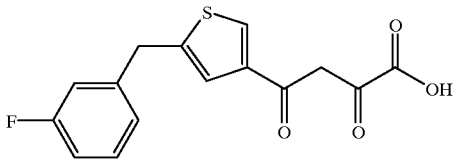

Step A:

Preparation of (4-bromothiophen-2-yl)-(3-fluorophenyl)methanol CI(2a)

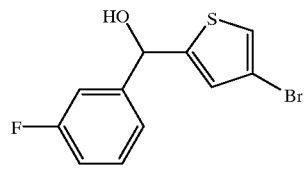

The title compound was prepared using the protocol described in Example BI(6a), Step A substituting 2,5-dibromothiophene with 2,4-dibromothiophene.

Step B:

Preparation of 4-bromo-2-(3-fluorobenzyl)thiophene CI(3a)

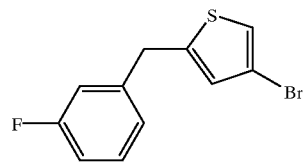

To a cold (0° C.) solution of (5-bromothiophen-2-yl)-(3-fluorophenyl)-methanol (3.78 g, 13.2 mmol) and triethylsilane (8.4 mL, 52.7 mmol) in dichloromethane (60 mL), boron trifluoride etherate (2.49 mL, 19.8 mmol) was added. The resultant mixture was stirred at rt for 2 h, and treated with sat. aq. sodium bicarbonate. The organic extract was washed with brine, dried over anhydrous magnesium sulfate, filtered, and concentrated under vacuum. The residue was subjected to column chromatography on silica gel eluting with hexane. Collection and concentration of appropriate fractions provide the title compound as clear colorless oil. The product was stored under argon in a freezer.

Step C:

Preparation of 2,4-dioxo-4-[5-(3-fluorobenzyl)thiophen-3-yl]butanoic acid CI(6a)

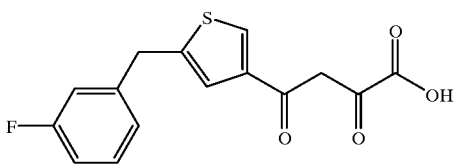

The title compound was prepared using the protocol described in Example BI(6a), Step C–E substituting 2-bromo-5-(3-fluorobenzyl)-thiophene with 4-bromo-2-(3-fluorobenzyl)thiophene in Step C. $^1$H NMR (CDCl$_3$) δ 8.08

(d, J=1.5 Hz, 1H), 7.35–7.25 (m, 3H), 7.05–6.92 (m, 2H), 6.90 (s, 1H), 4.15 (s, 2H).

EXAMPLE 13

2,4-dioxo-4-[5-(4-fluorobenzyl)thiophen-3-yl]butanoic acid

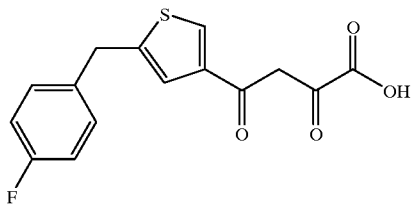

The title compound was prepared using the protocol described in Example CI(6a), Step A–C substituting 3-fluorobenzaldehyde with 4-fluoro-benzaldehyde in Step A. $^1$H NMR (CDCl$_3$) δ 8.07 (d, J=1.5 Hz, 1H), 7.26–7.18 (m, 3H), 7.05–6.92 (m, 2H), 6.89 (s, 1H), 4.13 (s, 2H).

EXAMPLE 14

2,4-dioxo-4-[5-(3-chlorobenzyl)thiophen-3-yl]butanoic acid

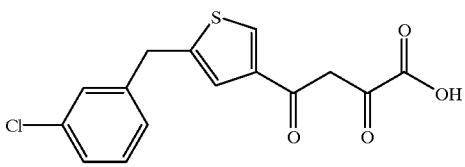

The title compound was prepared using the protocol described in Example CI(6a), Step A–C substituting 3-fluorobenzaldehyde with 3-chloro-benzaldehyde in Step A. $^1$H NMR (CDCl$_3$) δ 8.09 (br s, 1H), 7.28–7.22 (m, 4H), 7.14 (m, 1H), 6.90 (s, 1H), 4.13 (s, 2H).

EXAMPLE 15

2,4-dioxo-4-(5-benzylthiophen-3-yl)butanoic acid

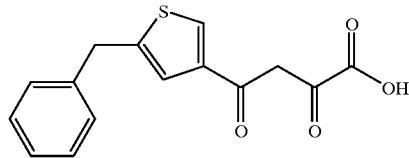

The title compound was prepared using the protocol described in Example CI(6a), Step A–C substituting 3-fluorobenzaldehyde with benzaldehyde in Step A. $^1$H NMR (CDCl$_3$) δ 8.07 (d, J=1.3 Hz, 1H), 7.36–7.22 (m, 6H), 6.89 (s, 1H), 4.16 (s, 2H).

EXAMPLE 16

2,4-dioxo-4-(2-phenylsulfanylthiophen-4-yl)butanoic acid

Step A:

Preparation of 2-phenylsulfanyl-4-bromothiophene CII (1)

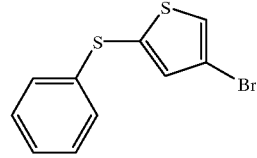

To a cold (−78° C.) solution of n-butyl lithium (10.4 mL, 2.5 M in hexane, 26 mmol) in anhydrous diethyl ether (100 mL) under an atmosphere of argon, 2,4-dibromothiophene (2.81 mL, 25 mmol) was added dropwise over a period of 15 min. After the reaction mixture was stirred at −78° C. for an additional 15 min, a solution of diphenyl disulfide (5.68 g, 52 mmol) in ether (50 mL) was added over a period of 15 min. The resultant mixture was allowed to warm to rt and stirred at rt overnight. The resultant solution was diluted with ether, and washed successively with aq. NaOH, and brine. The organic extract was dried over anhydrous magnesium sulfate, filtered, and concentrated under vacuum. The residue was subjected to column chromatography on silica gel eluting with hexane. Collection and concentration of appropriate fractions provided the title compound.

Step B:

Preparation of 4-acetyl-2-phenylsulfanylthiophene CII(2)

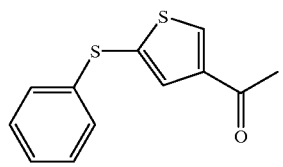

To a cold (−78° C.) solution of 2-phenylsulfanyl-4-bromothiophene (2.28 g, 8.4 mmol) in anhydrous diethyl ether (20 mL) under an atmosphere of argon, n-butyl lithium (5.78 mL, 1.6 M in hexane, 9.25 mmol) was added dropwise over a period of 5 min. After the reaction mixture was stirred at −78° C. for an additional 1 h, N-methoxy-N-methylacetamide (1.03 mL, 10 mmol) was added over a period of 5 min. The resultant mixture was allowed to warm to rt and stirred overnight. The resultant solution was diluted with ether, and neutralized with dilute HCl. The organic extract was washed with brine, dried over anhydrous magnesium sulfate, filtered, and concentrated under vacuum. The residue was subjected to column chromatography on silica gel eluting with 20% ethyl acetate in hexane. Collection and concentration of appropriate fractions provide the title compound as clear pale yellow oil.

Step C:

2,4-dioxo-4-(2-phenylsulfanylthiophen-4-yl)butanoic acid CII(4)

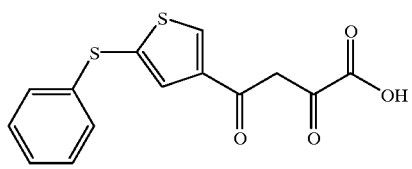

The title compound was prepared using the protocol described in Example AI(4), Step A and C substituting 2-acetyl-5-(phenylethynyl)-thiophene with 4-acetyl-2-phenylsulfanylthiophene in Step A. The product was recrystallized from a mixture of ether and hexane. $^1$H NMR (CDCl$_3$) δ 8.27 (d, J=1.5 Hz, 1H), 7.68 (d, J=1.5 Hz, 1H), 7.34–7.24 (m, 5H), 6.93 (s, 1H).

EXAMPLE 17

2,4-dioxo-4-[2-(3-fluorobenzyl)thiophen-3-yl] butanoic acid

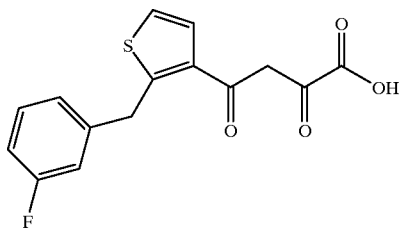

The title compound was prepared using the protocol described in Example BI(6a), Step A–E substituting 2,5-dibromothiophene with 1,2-dibromothiophene in Step A. $^1$H NMR (CDCl$_3$) δ 7.42 (d, J=5.5 Hz, 1H), 7.32–7.24 (m, 1H), 7.20 (dd, J=5.5, 1.1 Hz, 1H), 7.05 (br d, J=7.5 Hz, 1H), 6.98–6.92 (m, 3H), 4.57 (s, 2H).

EXAMPLE 18

2,4-dioxo-4-[2-(4-fluorobenzyl)thiophen-3-yl] butanoic acid

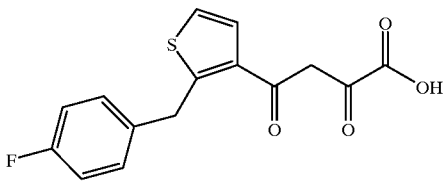

The title compound was prepared using the protocol described in Example BI(6a), Step A–E substituting 2,5-dibromothiophene with 1,2-dibromothiophene, and 3-fluorobenzaldehyde with 4-fluorobenzaldehyde in Step A. $^1$H NMR (DMSO-d$_6$) δ 7.62 (br d, 1H), 7.47 (br d, 1H), 7.35 (m, 2H), 7.15 (m, 2H), 6.83 (br s, 1H), 4.55 (s, 2H).

EXAMPLE 19

2,4-dioxo-4-[2-(3-chlorobenzyl)thiophen-3-yl] butanoic acid

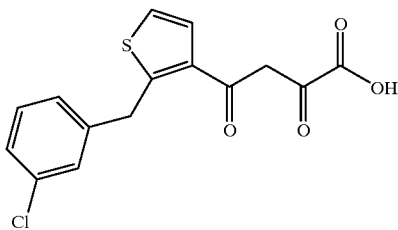

The title compound was prepared using the protocol described in Example BI(6a), Step A–E substituting 2,5-dibromothiophene with 1,2-dibromothiophene and 3-fluorobenzaldehyde with 3-chlorobenzaldehyde in Step A. $^1$H NMR (DMSO-d$_6$) δ 7.42 (br d, 1H), 7.3–7.1 (m, 5H), 6.92 (br s, 1H), 4.55 (s, 2H).

EXAMPLE 20

2,4-dioxo-4-[5-(benzyloxy-phenylmethyl)thiophen-2-yl]butanoic acid

Step A:
Preparation of (5-bromothiophen-2-yl)-(phenyl)methanol CI(2d)

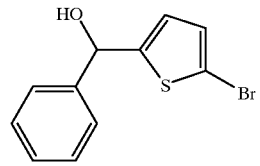

The title compound was prepared using the protocol described in Example BI(6a), Step A substituting 3-fluorobenzaldehyde with benzaldehyde. Without further purification, the alcohol was used in the following step.

Step B:
Preparation of 5-(benzyloxy-phenylmethyl)-2-bromothiophene EI(1a)

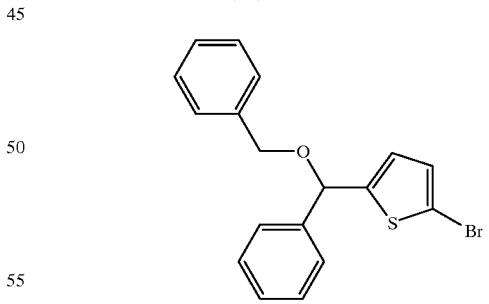

A suspension of sodium hydride (147 mg, 6 mmol) in anhydrous DMSO (20 mL) was stirred at 60° C. under an atmosphere of argon for 1 hr. The resultant mixture was cooled to rt, (5-bromothiophen-2-yl)-(phenyl)-methanol (1.5 g, 5.57 mmol) was added. After stirring for 10 min., benzyl bromide (0.8 mL, 6.68 mmol) was added. The mixture was stirred at rt under an atmosphere of argon overnight. The product mixture was concentrated under vacuum, and the residue partitioned between ethyl ether and dilute aqueous HCl. The organic extract was washed with brine, dried over anhydrous magnesium sulfate, filtered and concentrated under vacuum. The residue was subjected to column chromatography on silica gel eluting with 5% ethyl acetate in hexane. Collection and concentration of appropriate fractions provided the title compound.

Step C:
Preparation of 2,4-dioxo-4-[5-(benzyloxy-phenylmethyl) thiophen-2-yl]butanoic acid EI(5a)

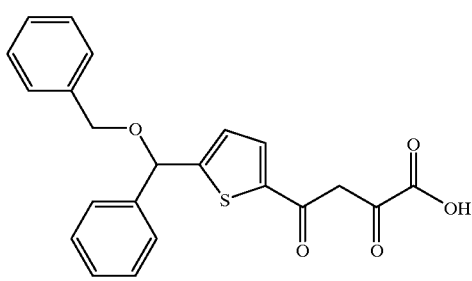

The title compound was prepared using the protocol described in Example BI(6a), Step C–E substituting 2-bromo-5-(3-fluorobenzyl)-thiophene with 5-(benzyloxy-phenylmethyl)-2-bromothiophene in Step C.
$^1$H NMR (CDCl$_3$) δ 7.71 (d, J=4.0 Hz, 1H), 7.5–7.3 (m, 9H), 6.94 (s, 1H), 6.86 (d, J=4.0 Hz, 1H), 5.62 (s, 2H), 4.63 (d, J=12.1 Hz, 1H), 4.53 (d, J=12.1 Hz, 1H).

EXAMPLE 21

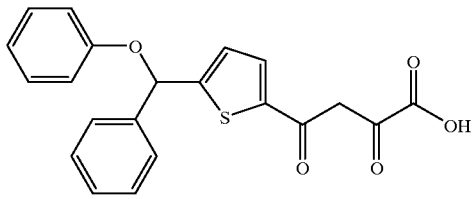

2,4-dioxo-4-[5-(phenoxy-phenylmethyl)thiophen-2-yl]butanoic acid

The title compound was prepared using the protocol described in Example EI(5a), Step A–C substituting benzyl bromide with diphenyl iodonium chloride in Step B. $^1$H NMR (CDCl$_3$) δ 7.73 (d, J=4.0 Hz, 1H), 7.5–7.2 (m, 7H), 7.01 (d, J=4.0 Hz, 1H), 6.94 (s, 1H), 7.00–6.95 (m, 3H), 6.41 (s, 1H).

EXAMPLE 22

2,4-dioxo-4-[5-(methoxy-phenylmethyl)thiophen-2-yl]butanoic acid

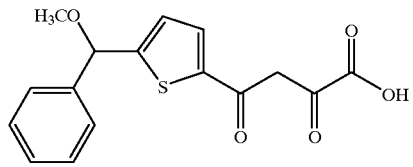

The title compound was prepared using the protocol described in Example EI(5a), Step A–C substituting benzyl bromide with methyl iodide in Step B. $^1$H NMR (CDCl$_3$) δ 7.71 (d, J=4.0 Hz, 1H), 7.42 (m, 7H), 6.94 (s, 1H), 6.92 (d, J=4.0 Hz, 1H), 3.42 (s, 3H).

EXAMPLE 23

2,4-dioxo-4-(5-dibenzylaminothiophen-2-yl) butanoic acid

Step A:
Preparation of 2-acetyl-5-aminothiophene hydrochloride FI(2)

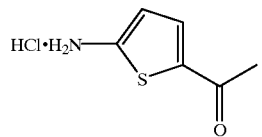

A mixture of 2-acetyl-5-nitrothiophene (5.00 g, 29.2 mmol), and 5% Pt$_2$S/C (3 g) in methanol (120 mL) was stirred under a balloon of hydrogen overnight at rt. To the resulting mixture, an ethanolic solution of hydrogen chloride gas was added (final pH~2), and the solution was filtered through a pad of Celite. The filtrate was concentrated under vacuum to provide the title compound.

Step B:
Preparation of 2-acetyl-5-dibenzylaminothiophene FI(3a)

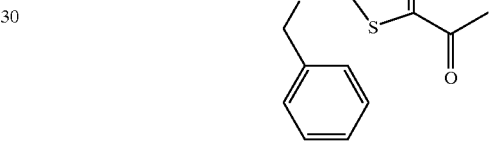

A mixture of 2-acetyl-5-aminothiophene hydrochloride (700 mg, 3.94 mmol), benzyl bromide (0.94 mL, 7.88 mmol), and diisopropylethylamine (2.4 mL, 13.8 mmol) in acetonitrile (15 mL) was stirred at 60° C. for 7 days. The resulting mixture was concentrated under vacuum. The residue was subjected to column chromatography on silica gel eluting with chloroform—chloroform saturated with ammonia gradient. Collection and concentration of appropriate fractions provided the title compound as red oil.

Step C:
Preparation of 2,4-dioxo-4-(5-dibenzylaminothiophen-2-yl)butanoic acid FI(5a)

The title compound was prepared using the protocol described in Example AI(4), Step A and C substituting 2-acetyl-5-(phenylethynyl)-thiophene with 2-acetyl-5-dibenzylaminothiophene in Step A. The product was purified by HPLC on C-18 stationary phase. $^1$H NMR (DMSO-d$_6$) δ 7.93 (d, J=4.8 Hz, 1H), 7.40–7.25 (m, 10H), 6.79 (s, 1H), 6.27 (d, J=4.8 Hz, 1H), 4.81 (s, 4H).

EXAMPLE 24

2,4-dioxo-4-(5-benzylaminothiophen-2-yl)butanoic acid

Step A:
Preparation of 2-acetyl-5-benzylaminothiophene FI(3b)

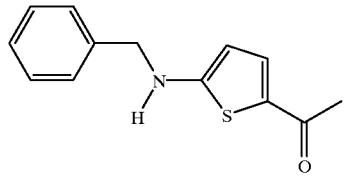

A mixture of 2-acetyl-5-aminothiophene hydrochloride (700 mg, 3.94 mmol), benzyl bromide (0.47 mL, 3.94 mmol), and diisopropylethylamine (1.72 mL, 9.85 mmol) in acetonitrile (15 mL) was stirred at 60° C. for 4 days. The resulting mixture was concentrated under vacuum. The residue was subjected to column chromatography on silica gel eluting with chloroform—chloroform saturated with ammonia gradient. Collection and concentration of appropriate fractions provided the title compound.

Step B:
Preparation of 2,4-dioxo-4-(5-benzylaminothiophen-2-yl) butanoic acid FI(5b)

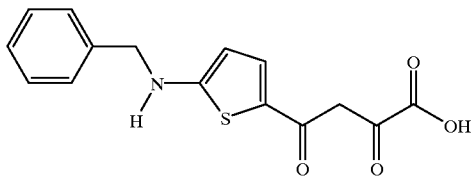

The title compound was prepared using the protocol described in Example AI(4), Step A and C substituting 2-acetyl-5-(phenylethynyl)-thiophene with 2-acetyl-5-benzylaminothiophene in Step A. The product was purified by HPLC on C-18 stationary phase. $^1$H NMR (CD$_3$OD) δ 7.70 (d, J=4.6 Hz, 1H), 7.40–7.25 (m, 5H), 6.79 (s, 1H), 6.14 (d, J=4.6 Hz, 1H), 4.86 (s, 2H).

EXAMPLE 25

2,4-dioxo-4-(5-diallylaminothiophen-2-yl)butanoic acid

Step A:
Preparation of 2-acetyl-5-diallylaminothiophene FI(3c)

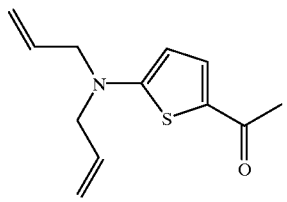

A mixture of 2-acetyl-5-aminothiophene hydrochloride (1.5 g, 8.44 mmol), allyl bromide (7.30 mL, 84.4 mmol), and diisopropylethylamine (6.5 mL, 37.3 mmol) in acetonitrile (10 mL) was stirred at 60° C. for 3 days. The resulting mixture was concentrated under vacuum. The residue was subjected to column chromatography on silica gel eluting with 40% ethyl acetate in hexane. Collection and concentration of appropriate fractions provided the title compound as orange oil.

Step B:
Preparation of 2,4-dioxo-4-(5-diallylaminothiophen-2-yl) butanoic acid FI(5c)

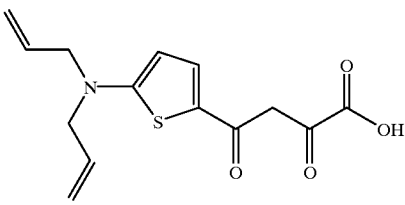

The title compound was prepared using the protocol described in Example AI(4), Step A and C substituting 2-acetyl-5-(phenylethynyl)-thiophene with 2-acetyl-5-diallylaminothiophene in Step A. The product was purified by HPLC on C-18 stationary phase. $^1$H NMR (CDCl$_3$) δ 7.67 (d, J=4.6 Hz, 1H), 6.76 (s, 1H), 6.06 (d, J=4.6 Hz, 1H), 5.85 (m, 2H), 5.3 (m, 4H), 4.05 (m, 4H).

EXAMPLE 26

2,4-dioxo-4-(5-di-n-propylaminothiophen-2-yl) butanoic acid

Step A:
Preparation of 2-acetyl-5-di-n-propylaminothiophene FI(3d)

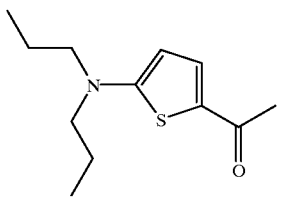

A mixture of 2-acetyl-5-diallylaminothiophene (200 mg, 0.904 mmol) and 5% Pd/C (200 mg) in methanol (10 mL) was stirred under a balloon of hydrogen for 3 h. The resulting mixture was filtered through a pad of of Celite™, diatomaceous earth. The filtrate was concentrated under vacuum to provide the title compound.

Step B:
Preparation of 2,4-dioxo-4-(5-di-n-propylaminothiophen-2-yl)butanoic acid FI(5d)

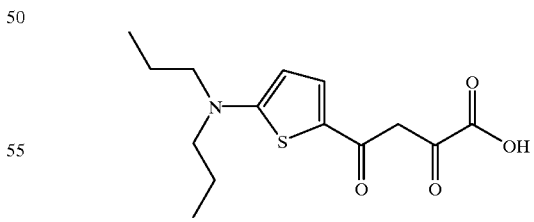

The title compound was prepared using the protocol described in Example AI(4), Step A and C substituting 2-acetyl-5-(phenylethynyl)-thiophene with 2-acetyl-5-di-n-propylaminothiophene in Step A. The product was purified by HPLC on C-18 stationary phase. $^1$H NMR (DMSO-d$_6$) δ 7.95 (d, J=4.8 Hz, 1H), 6.81 (s, 1H), 6.19 (d, J=4.8 Hz, 1H), 3.38 (t, J=7.5 Hz, 4H), 1.62 (h, J=7.5 Hz, 4H), 0.89 (d, J=7.5 Hz, 6H),

EXAMPLE 27

2,4-dioxo-4-[5-(di-4-fluorobenzylamino)thiophen-2-yl]butanoic acid

Step A:

Preparation of 2-acetyl-5-(di-4-fluorobenzylamino)thiophene FI(3e)

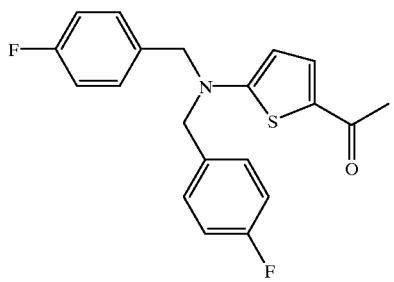

A mixture of 2-acetyl-5-aminothiophene hydrochloride (600 mg, 3.38 mmol), 4-fluorobenzyl bromide (0.92 mL, 7.43 mmol), and $Cs_2CO_3$ (2.42 g, 7.43 mmol) in DMF (10 mL) was stirred at rt for 2 days. The resulting mixture was concentrated under vacuum. The residue was treated with a mixture of chloroform and aq HCl. After stirring at rt for 1 h, the pH of the mixture was adjusted to ~8. The organic extract was washed with brine, dried over sodium sulfate, filtered and concentrated under vacuum. The residue was subjected to column chromatography on silica gel eluting with 40% ethyl acetate in hexane. Collection and concentration of appropriate fractions provided the title compound.

Step B:

Preparation of 2,4-dioxo-4-[5-(di-4-fluorobenzylamino)thiophen-2-yl]butanoic acid FI(5e)

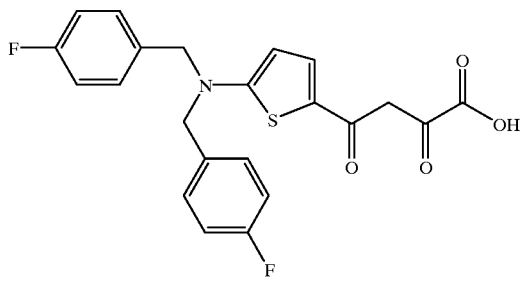

The title compound was prepared using the protocol described in Example AI(4), Step A and C substituting 2-acetyl-5-(phenylethynyl)-thiophene with 2-acetyl-5-(di-4-fluorobenzylamino)thiophene in Step A. $^1$H NMR (CDCl$_3$) δ 7.66 (d, J=4.6 Hz, 1H), 7.2–7.0 (m, 8H), 6.78 (s, 1H), 6.14 (d, J=4.6 Hz, 1H), 4.59 (s, 4H).

EXAMPLE 28

2,4-dioxo-4-[5-(N-benzyl-N-methylamino)thiophen-2-yl]butanoic acid

Step A:

Preparation of 2-acetyl-5-(N-benzyl-N-methylamino)thiophene FII(1a)

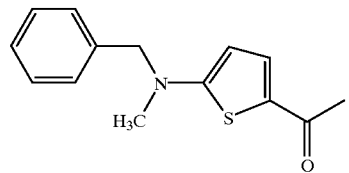

A solution of cesium carbonate (3.25 g, 10 mmol), N-methyl-N-benzylamine (2.58 mL, 20 mmol) and 2-acetyl-5-chlorothiophene (1.61 g, 10 mmol) in DMF (20 mL) was stirred at 60° C. under an atmosphere of argon for 9 days. The product mixture was concentrated under vacuum, and the residue was treated with a mixture of ethyl ether and dilute aqueous HCl. After stirring at rt for 1 h, pH of the solution was adjusted to ~8 with sat. aq. NaHCO$_3$, and organic extract was washed with brine, dried over anhydrous sodium sulfate, filtered and concentrated under vacuum. The residue was subjected to column chromatography on silica gel eluting with 30% ethyl acetate in hexane. Collection and concentration of appropriate fractions provided the title ketone.

Step B:

Preparation of 2,4-dioxo-4-[5-(N-benzyl-N-methylamino)thiophen-2-yl]butanoic acid FII(3a)

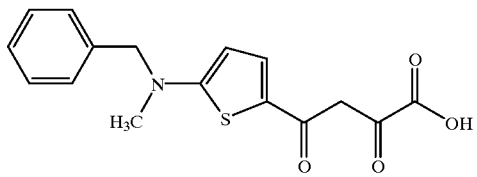

The title compound was prepared using the protocol described in Example AI(4), Step A and C substituting 2-acetyl-5-(phenylethynyl)-thiophene with 2-acetyl-5-(benzylmethylamino)thiophene in Step A. $^1$H NMR (CDCl$_3$) δ 7.70 (d, J=4.6 Hz, 1H), 7.4–7.2 (m, 5H), 6.77 (br s, 1H), 6.10 (d, J=4.6 Hz, 1H), 4.62 (s, 2H), 3.15 (s, 3H).

EXAMPLE 29

2,4-dioxo-4-(5-piperidin-1-yl-thiophen-2-yl)butanoic acid

Step A:

Preparation of 2-acetyl-5-piperidin-1-yl-thiophene FII(2b)

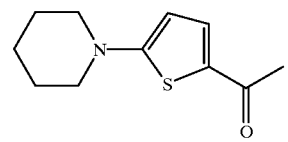

The title compound was prepared using the protocol described in Example FII(3a), Step A and C substituting N-methyl-N-benzylamine with piperidine in Step A, and using DMSO as solvent.

Step B:

Preparation of 2,4-dioxo-4-(5-piperidin-1-yl-thiophen-2-yl)butanoic acid FII(3b)

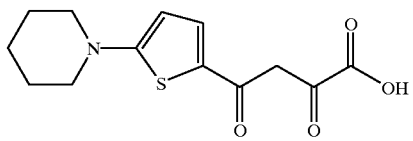

The title compound was prepared using the protocol described in Example AI(4), Step A and C substituting 2-acetyl-5-(phenylethynyl)-thiophene with 2-acetyl-5-piperidin-1-yl-thiophene in Step A. $^1$H NMR (CDCl$_3$) δ 7.70 (d, J=4.8 Hz, 1H), 6.77 (br s, 1H), 6.13 (d, J=4.6 Hz, 1H), 3.41 (t, J=5.7 Hz, 4H), 1.7 (m, 6H).

EXAMPLE 30

2,4-dioxo-4-[5-(benzylbenzenesulfonylamino) thiophen-2-yl]butanoic acid

Step A:

Preparation of 2-acetyl-5-(benzenesulfonylamino) thiophene FIII(1)

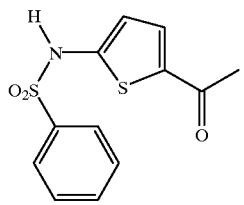

A solution of 2-amino-5-acetylthiophene hydrochloride (0.75 g, 4.22 mmol), benzenesulfonyl chloride (0.7 mL, 5.49 mmol) in pyridine (15 mL) was stirred at 70° C. under an atmosphere of argon for 1.5 h. The product mixture was concentrated under vacuum, and the residue was partitioned between ethyl acetate and aq. HCl. The organic extract was washed with brine, dried over anhydrous sodium sulfate, filtered and concentrated under vacuum. The residue was subjected to column chromatography on silica gel eluting with 50% ethyl acetate in hexane. Collection and concentration of appropriate fractions provided the title sulfonamide.

Step B:

Preparation of 2-acetyl-5-(benzylbenzenesulfonylamino) thiophene FIII(2)

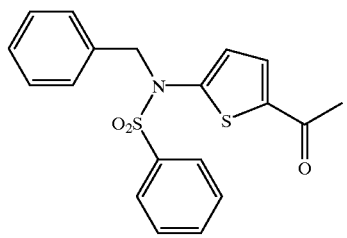

To a solution of 2-acetyl-5-(benzenesulfonylamino) thiophene (0.192 g, 0.682 mmol) in DMSO (11.5 mL), a solution of NaHMDS (0.72 mL, 1M) in THF was added. The resultant deep red solution was stirred at rt for 2.5 h, and treated with benzyl bromide (89.2 µL, 0.75 mmol), and stirred at rt overnight. The product mixture was concentrated under vacuum, and the residue was partitioned between dichloromethane and aq. HCl. The organic extract was washed with brine, dried over anhydrous MgSO$_4$, filtered and concentrated under vacuum. The residue was subjected to column chromatography on silica gel eluting with 40% ethyl acetate in hexane. Collection and concentration of appropriate fractions provided the title ketone.

Step C:

Preparation of 2,4-dioxo-4-[5-(benzylbenzenesulfonylamino)thiophen-2-yl]butanoic acid FIII(4)

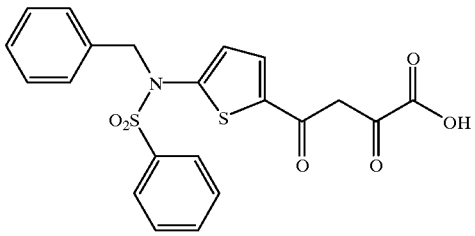

The title compound was prepared using the protocol described in Example AI(4), Step A and C substituting 2-acetyl-5-(phenylethynyl)-thiophene with 2-acetyl-5-(benzylbenzenesulfonylamino)thiophene in Step A. $^1$H NMR (CDCl$_3$) δ 7.76 (d, J=4.5 Hz, 1H), 7.7–7.5 (m, 5H), 7.3 (m, 5H), 6.83 (br s, 1H), 6.82 (d, J=4.5 Hz, 1H), 4.83 (s, 4H).

EXAMPLE 31

2,4-dioxo-4-(2-dibenzylaminothiazol-5-yl)butanoic acid

Step A:

Preparation of 1,1-dibenzylthiourea GI(1a)

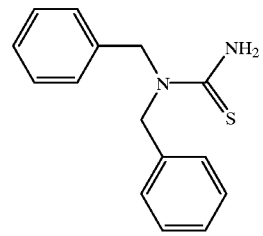

A mixture of dibenzylamine (9.6 mL, 50 mmol) and tert-butyl isothiocyanate (6.34 mL, 50 mmol) in hexane (50 mL) was stirred at rt overnight. The white precipitate was isolated by filtration, and was treated with concentrated hydrochloric acid (25 mL) at 100° C. for 1.5 h. The product mixture was concentrated under vacuum. The residue was treated with 10% aq. NaHCO$_3$. The white solid precipitated was obtained by filtration, and recrystallized from a mixture of chloroform and hexane. Filtration provided the title compound as white powder.

Step B:

Preparation of 1,1-dibenzyl-3-dimethylaminomethylenethiourea GI(2a)

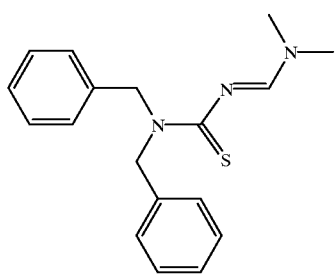

A mixture of 1,1-dibenzylthiourea (4.0 g, 15.6 mmol) and N,N-dimethylformamide dimethyl acetal (20 mL) was heated at 100° C. for 1 h. The reaction mixture was concentrated, and the residue was recrystallized from a mixture of chloroform and hexane. Filtration of the white solid provide the title compound.

Step C:

Preparation of 2-dibenzylamino-5-acetylthiazole GI(3a)

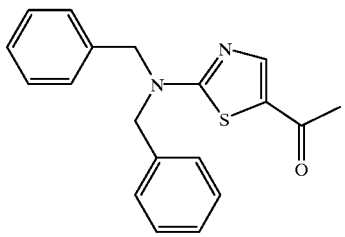

A solution of 1,1-dibenzyl-3-dimethylaminomethylenethiourea (1.8 g, 5.78 mmol) and bromoacetone (0.93 g, 5.78 mmol) in acetone (25 mL) was stirred in the dark for 3 days. The resultant mixture was concentrated under vacuum, and the residue partitioned between toluene and aq. sodium bicarbonate. The organic extract was washed with brine, dried over $Na_2SO_4$, filtered and concentrated under vacuum. The residue was recrystallized from a mixture ethyl acetate and hexane to provide the title compound as light yellow solid.

Step D:

Preparation of 2,4-dioxo-4-(2-dibenzylaminothiazol-5-yl) butanoic acid GI(5a)

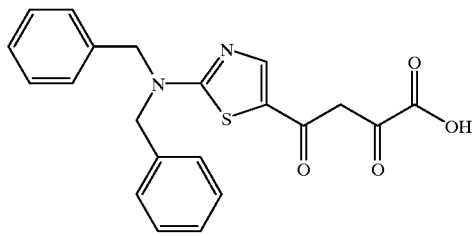

The title compound was prepared using the protocol described in Example AI(4), Step A and C substituting 2-acetyl-5-(phenylethynyl)-thiophene with 2-dibenzylamino-5-acetylthiazole in Step A. The product was purified by recrystallization from toluene. $^1$H NMR ($CDCl_3$) δ 8.19 (s, 1H), 7.40–7.20 (m, 10H), 6.81 (s, 1H), 4.76 (s, 4H).

EXAMPLE 32

2,4-dioxo-4-(2-benzylaminothiazol-5-yl)butanoic acid

Step A:

Preparation of 1-benzyl-3-dimethylaminomethylenethiourea GI(2b)

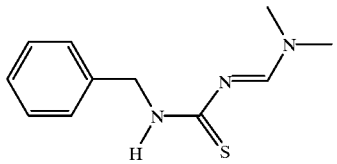

A mixture of 1-benzylthiourea (8.3 g, 50 mmol) and N,N-dimethyl-formamide dimethyl acetal (25 mL) was heated at 100° C. for 1 h. The reaction mixture was concentrated, and the residue was recrystallized from a mixture of chloroform and hexane. Filtration of the white solid provide the title compound.

Step B:

Preparation of 2-benzylamino-5-acetylthiazole GI(3b)

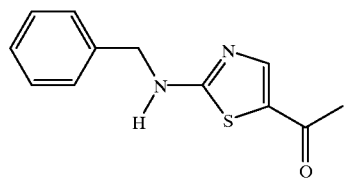

A solution of 1-benzyl-3-dimethylaminomethylenethiourea (4.0 g, 18 mmol) and bromoacetone (2.5 g, 18.3 mmol) in acetone (75 mL) was stirred in the dark for 3 days. The white precipitated was isolated by filtration and dissolved in chloroform. The organic solution was washed successively with aq. $NaHCO_3$, brine, dried over $Na_2SO_4$, filtered and concentrated under vacuum. The residue was recrystallized from a mixture dichloromethane and hexane to provide the title compound.

Step C:

Preparation of 2,4-dioxo-4-(2-benzylaminothiazol-5-yl) butanoic acid GI(5b)

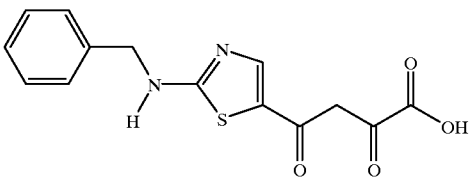

The title compound was prepared using the protocol described in Example AI(4), Step A and C substituting 2-acetyl-5-(phenylethynyl)-thiophene with 2-benzylamino-5-acetylthiazole in Step A. The product was purified by recrystallization from a mixture of THF and hexane. $^1$H NMR (DMSO-$d_6$) δ 9.50 (br s, 1H), 8.39 (s, 1H), 7.40–7.20 (m, 5H), 6.88 (s, 1H), 4.57 (d, J=5.4 Hz, 2H).

EXAMPLE 33

2,4-dioxo-4-(2-N-benzyl-N-methylaminothiazol-5-yl)butanoic acid

Step A:
Preparation of 2-N-benzyl-N-methylamino-5-acetylthiazole GI(3c)

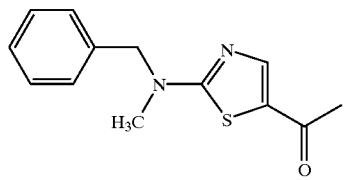

The title compound was prepared using the protocol described in Example GI(5a), Step A–C substituting N,N-dibenzylamine with N-benzyl-N-methylamine in Step A.

Step B:
Preparation of 2,4-dioxo-4-(2-N-benzyl-N-methylaminothiazol-5-yl)butanoic acid GI(5c)

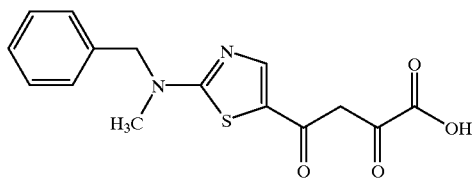

The title compound was prepared using the protocol described in Example AI(4), Step A and C substituting 2-acetyl-5-(phenylethynyl)-thiophene with 2-N-benzyl-N-methylamino-5-acetylthiazole in Step A. The product was purified by recrystallization from toluene. $^1$H NMR (CDCl$_3$) δ 8.01 (s, 1H), 7.40–7.20 (m, 5H), 6.78 (s, 1H), 4.82 (s, 2H), 3.15 (s, 3H).

EXAMPLE 34

2,4-dioxo-4-(2-dibenzylaminothiazol-4-yl)butanoic acid

Step A:
Preparation of 2-dibenzylamino-4-acetylthiazole GII(3)

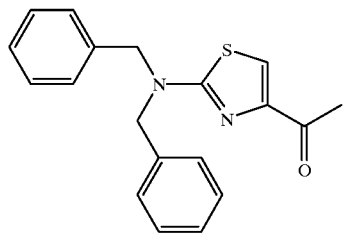

A suspension of 1,1-dibenzylthiourea (3.05 g, 11.9 mmol) in absolute ethanol (40 mL) was treated with 1-bromo-2,3-butanedione (2.06 g, 12.5 mmol). The mixture was heated under reflux for 2 h. The resultant mixture was cooled to 0° C., and white solid precipitated. The white solid was dissolved in ethyl acetate, and washed with sat. aq. NaHCO$_3$. The organic extract was washed with brine, dried over Na$_2$SO$_4$, filtered and concentrated under vacuum. The residue solidified upon standing to provide the title compound.

Step D:
Preparation of 2,4-dioxo-4-(2-dibenzylaminothiazol-4-yl)butanoic acid GII(5)

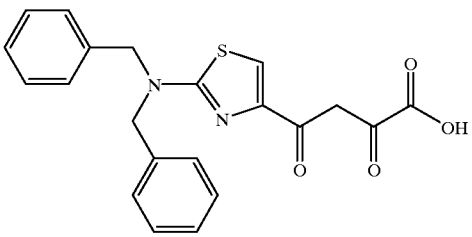

The title compound was prepared using the protocol described in Example AI(4), Step A and C substituting 2-acetyl-5-(phenylethynyl)-thiophene with 2-dibenzylamino-4-acetylthiazole in Step A. The product was purified by recrystallization from a mixture of ether and hexane as orange needles. $^1$H NMR (CDCl$_3$) δ 7.56 (s, 1H), 7.40–7.20 (m, 11H), 4.70 (s, 4H).

EXAMPLE 35

HIV Integrase Assay: Strand Transfer Catalyzed by Recombinant Integrase and Preintegration Complexes Assays for the strand transfer activity of integrase were conducted according to Wolfe, A. L. et al., J. Virol. 70, 1424 (1996), and Farnet, C. M. and Bushman F. D. (1997) Cell; 88, 483 for recombinant integrase and preintegration complexes, respectively, hereby incorporated by reference for these purposes.

Representative compounds tested in the integrase assay demonstrated IC50's less than 1 micromolar. Further, representative compounds tested in the preintegration complex assay also demonstrated IC50's of less than 1 micromolar.

EXAMPLE 36

Assay for Inhibition of HIV Replication

Assays for the inhibition of acute HIV infection of T-lymphoid cells was conducted according to Vacca, J. P. et al., (1994), Proc. Natl. Acad. Sci. USA 91, 4906, herein incorporated by reference for these purposes.

Representative compounds tested in the present assay demonstrated IC$_{95}$s of less than 10 micromolar.

EXAMPLE 37

Oral Composition

As a specific embodiment of an oral composition of a compound of this invention, 50 mg of a compound of the present invention is formatted with sufficient finely divided lactose to provide a total amount of 580 to 590 mg to fill a size 0 hard gelatin capsule.

While the foregoing specification teaches the principles of the present invention, with examples provided for the purpose of illustration, it will be understood that the practice of the invention encompasses all of the usual variations, adoptions, or modifications, as come within the scope of the following claims and their equivalents.

What is claimed:
1. The compound of structural formula (I):

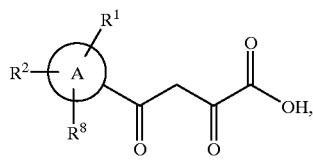

and tautomers and pharmaceutically acceptable salts thereof, wherein:

A is selected from:
  (1) thienyl,
  (2) thiazolyl,

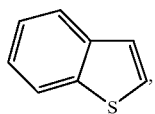
(3)

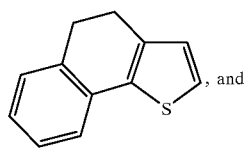
(4)

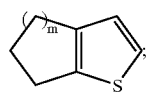
(5)

$R^1$ is selected from:
  (1) —H,
  (2) —$CH_3$,
  (3) —$CF_3$,
  (4) -halo,
  (5) —$NO_2$,
  (6) —$N(R^4)(R^5)$,
  (7) -phenyl,
  (8) substituted phenyl substituted with 1 or 2 substituents independently selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen,
      (ii) $C_{1-6}$ alkyl,
      (iii) —$CF_3$, and
      (iv) hydroxy;
  (9) phenyl $C_{1-3}$ alkyl-,
  (10) substituted phenyl $C_{1-3}$ alkyl-substituted with 1 or 2 substituents independently selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen,
      (ii) $C_{1-6}$ alkyl,
      (iii) —$CF_3$, and
      (iv) hydroxy;
  (11) —$C_{2-5}$ alkenyl-$R^3$,
  (12) —$C_{2-5}$ alkynyl-$R^3$, and
  (13) —$C(O)CH_2C(O)C(O)OR^7$;

$R^2$ is selected from:
  (1) —H,
  (2) —$R^3$,
  (3) —$C_{1-6}$ alkyl,
  (4) —$C_{1-6}$ alkyl substituted with $R^3$,
  (5) —O—$R^6$,
  (6) —O—$C_{1-6}$ alkyl-$OR^6$,
  (7) —$S(O)n$—$R^6$,
  (8) —$C_{1-6}$ alkyl $(OR^6)(R^4)$,
  (9) —$C_{1-6}$ alkyl $(OR^4)(R^6)$,
  (10) —$C_{0-6}$ alkyl-$N(R^4)(R^6)$,
  (11) —$C_{1-6}$ alkyl $S(O)n$—$R^6$,
  (12) —$C_{0-6}$ alkyl $C(O)$—$R^6$,
  (13) —$C_{0-6}$ alkyl $C(S)$—$R^6$,
  (14) —$C_{0-6}$ alkyl $NR^4C(O)$—$R^6$, and
  (15) —$C_{0-6}$ alkyl-$C(O)N(R^4)(R^5)$;

each $R^3$ is independently selected from:
  (1) phenyl;
  (2) substituted phenyl with 1, 2, or 3 substituents independently selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen,
      (ii) $C_{1-6}$ alkyl,
      (iii) —$CF_3$, and
      (iv) hydroxy;
  (3) thienyl;
  (4) substituted thienyl substituted on a carbon atom with one or two substituents independently selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen,
      (ii) $C_{1-6}$ alkyl, (iii) —CF$_3$, and
(iv) hydroxy;
(5) pyridyl;
(6) substituted pyridyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(7) imidazolyl;
(8) substituted imidazolyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(9) pyrrolyl;
(10) substituted pyrrolyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(11) pyrazolyl;
(12) substituted pyrazolyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(13) C$_{3-6}$ cycloalkyl;
(14) substituted C$_{3-6}$ cycloalkyl with 1 or 2 substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy;
(15) piperidinyl;
(16) substituted piperidinyl substituted on a carbon atom with one or two substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy;
(17) morpholinyl;
(18) substituted morpholinyl substituted at a carbon or nitrogen atom with 1 or 2 substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy;
(19) naphthyl,
(20) substituted naphthyl with 1, 2, or 3 substituents independently selected from:
(a) -halogen,
(b) —C$_{1-6}$ alkyl,
(c) C$_{1-6}$ alkyloxy-,
(d) —CF$_3$,
(e) —OCF$_3$,
(f) —CN, and
(g) -hydroxy;
(21) indolyl;
(22) substituted indolyl substituted on a carbon atom with one or two substituents independently selected from:
(a) -halogen,
(b) —C$_{1-6}$ alkyl,
(c) C$_{1-6}$ alkyloxy-,
(d) —CF$_3$,
(e) —OCF$_3$,
(f) —CN, and
(g) -hydroxy;

(23) $C_{3-6}$ cycloalkyl fused with a phenyl ring
(24) substituted $C_{3-6}$ cycloalkyl fused with a phenyl ring substituted on a carbon atom with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
each $R^4$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$,
  (8) —$S(O)_n$—$R^3$, and
  (9) —C(O)—$R^3$;
each $R^5$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{1-3}$ alkenyl-$R^3$,
  (8) —$S(O)_n$—$R^3$, and
  (9) —C(O)—$R^3$;
each $R^6$ is independently selected from:
  (1) —$C_{1-3}$ alkyl-$R^3$, and
  (2) —$R^3$;
$R^7$ is H;
$R^8$ is selected from hydrogen, methyl and methoxy;
each n is independently selected from 0, 1 and 2, and
each m is independently selected from 0, 1, and 2;
and provided that
  (A) when A is thienyl or thiazolyl and $R^2$ is —H or —$C_{1-6}$ alkyl, then $R^1$ is not
    (1) —H,
    (2) —$CH_3$, or
    (7) -phenyl;
  (B) when A is thienyl or thiazolyl and $R^2$ is —$R^3$ wherein $R^3$ is unsubstituted phenyl, then $R^1$ is not
    (1) —H or
    (2) —$CH_3$;
  (C) when A is thienyl and $R^2$ is —H or —$C_{1-6}$ alkyl, then $R^1$ is not
    (4) -halo,
    (5) —$NO_2$, or
    (6) —$N(R^4)(R^5)$ when $R^4$ and $R^5$ are both —H; and
  (D) when A is thienyl and $R^2$ is —$R^3$ wherein $R^3$ is (7) imidiazolyl or (17) morpholinyl, then $R^1$ is not
    (1) —H,
    (2) —$CH_3$,
    (4) -halo,
    (5) —$NO_2$, or
    (6) —$N(R^4)(R^5)$ when $R^4$ and $R^5$ are both —H.

2. The compound according to claim 1, and tautomers and pharmaceutically acceptable salts thereof, wherein:

A is selected from:
  (1) thienyl,
  (2) thiazolyl,

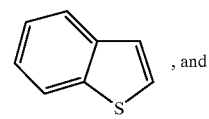
, and

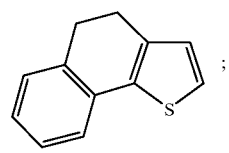
;

$R^1$ is selected from:
  (1) —H,
  (2) —$CH_3$,
  (3) —$CF_3$,
  (4) -halo,
  (5) —$NO_2$,
  (6) —$N(R^4)(R^5)$,
  (7) -phenyl,
  (8) substituted phenyl substituted with 1 or 2 substituents independently selected from:
    (a) halo,
    (b) methyl, and
    (c) methoxy,
  (9) phenyl $C_{1-3}$ alkyl-,
  (10) substituted phenyl $C_{1-3}$ alkyl-substituted with 1 or 2 substituents independently selected from:
    (a) halo,
    (b) methyl, and
    (c) methoxy, and
  (11) —$C_{2-5}$ alkenyl-$R^3$;
$R^2$ is selected from:
  (1) —H,
  (2) —R,
  (3) —$C_{1-6}$ alkyl,
  (4) —$C_{1-6}$ alkyl substituted with $R^3$,
  (5) —O—$R^6$,
  (6) —$S(O)n$—$R^6$,
  (7) —$C_{1-6}$ alkyl $(OR^6)(R^4)$,
  (8) —$C_{1-6}$ alkyl $(OR^4)(R^6)$,
  (9) —$C_{0-6}$ alkyl-$N(R^4)(R^6)$,
  (10) —$C_{1-6}$ alkyl $S(O)n$—$R^6$,
  (11) —$C_{0-6}$ alkyl C(O)—$R^6$,
  (12) —$C_{0-6}$ alkyl $NR^4C(O)$—$R^6$, and
  (13) —$C_{0-6}$ alkyl-$C(O)N(R^4)(R^5)$;
each $R^3$ is independently selected from:
  (1) phenyl,
  (2) substituted phenyl with 1, 2, or 3 substituents independently selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen,
      (ii) $C_{1-6}$ alkyl, (iii) —CF$_3$, and
(iv) hydroxy;
(3) thienyl;
(4) substituted thienyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(5) pyridyl;
(6) substituted pyridyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen,
(ii) C$_{1-6}$ alkyl,
(iii) —CF$_3$, and
(iv) hydroxy;
(7) imidazolyl;
(8) pyrrolyl;
(9) pyrazolyl;
(10) C$_{3-6}$ cycloalkyl,
(11) substituted C$_{3-6}$ cycloalkyl with 1 or 2 substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy;
(12) piperidinyl;
(13) substituted piperidinyl substituted on a carbon atom with one or two substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy;
(14) morpholinyl;
(15) naphthyl;
(16) indolyl; and
(17) C$_{3-6}$ cycloalkyl fused with a phenyl ring;

each R$^4$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$, and
(7) —S(O)$_n$—R$^3$; and each R$^5$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$,
(7) —C$_{2-3}$ alkenyl-R$^3$, and
(8) —S(O)$_n$—R$^3$;

each R$^6$ is independently selected from:
(1) —C$_{1-3}$ alkyl-R$^3$, and
(2) —R$^3$;

R$^8$ is H; and each n is independently selected from 0, 1 and 2;

and provided that
(A) when A is thienyl or thiazolyl and R$^2$ is —H or —C$_{1-6}$ alkyl, then R$^1$ is not
(1) —H,
(2) —CH$_3$, or
(7) -phenyl;
(B) when A is thienyl or thiazolyl and R$^2$ is —R$^3$ wherein R$^3$ is unsubstituted phenyl, then R$^1$ is not
(1) —H or
(2) —CH$_3$; and
(C) when A is thienyl and R$^2$ is —H or —C$_{1-6}$ alkyl, then R$^1$ is not
(4) -halo,
(5) —NO$_2$, or
(6) —N(R$^4$)(R$^5$) when R$^4$ and R$^5$ are both —H; and
(D) when A is thienyl and R$^2$ is —R$^3$ wherein R$^3$ is (7) imidiazolyl or (17) morpholinyl, then R$^1$ is not
(1) —H,
(2) —CH$_3$,
(4) -halo,
(5) —NO$_2$, or
(6) —N(R$^4$)(R$^5$) when R$^4$ and R$^5$ are both —H.

3. The compound according to claim 1 of structural formula:

and tautomers and pharmaceutically acceptable salts thereof, wherein:
R$^2$ is selected from:
(1) —R$^3$,
(2) —C$_{1-6}$ alkyl substituted with R$^3$,
(3) —O—R$^6$,
(4) —S(O)n—R$^6$,
(5) —C$_{1-6}$ alkyl (OR$^6$)(R$^4$),
(6) —C$_{1-6}$ alkyl (OR$^4$)(R$^6$), (7) —C₀₋₆ alkyl-N(R⁴)(R⁶),
(8) —C₁₋₆ alkyl S(O)n—R⁶,
(9) —C₀₋₆ alkyl C(O)—R⁶,
(10) —C₀₋₆ alkyl NR⁴C(O)—R⁶, and
(11) —C₀₋₆ alkyl-C(O)N(R⁴)(R⁵);

each R³ is independently selected from:
(1) phenyl,
(2) substituted phenyl with 1, 2, or 3 substituents independently selected from:
  (a) halogen selected from —F, —Cl, and —Br,
  (b) CH₃,
  (c) methoxy-,
  (d) phenyl,
  (e) —CF₃,
  (f) —OCF₃,
  (g) —CN,
  (h) hydroxy,
  (i) phenyloxy, and
  (j) substituted phenyloxy with 1, 2, or 3 substituents selected from:
    (i) halogen selected from —F, —Cl, and —Br,
    (ii) —CH₃,
    (iii) —CF₃, and
    (iv) hydroxy;
(3) thienyl,
(4) pyridyl,
(5) imidazolyl,
(6) pyrrolyl,
(7) pyrazolyl,
(8) C₃₋₆ cycloalkyl,
(9) piperidinyl,
(10) morpholinyl,
(11) naphthyl,
(12) indolyl, and
(13) C₃₋₆ cycloalkyl fused with a phenyl ring;

each R⁴ is independently selected from:
(1) —H,
(2) —C₁₋₃ alkyl,
(3) —CF₃,
(4) —R³,
(5) —C₂₋₃ alkenyl,
(6) —C₁₋₃ alkyl-R³, and
(7) —S(O)ₙ—R³, each R⁵ is independently selected from:
(1) —H,
(2) —C₁₋₃ alkyl,
(3) —CF₃,
(4) —R³,
(5) —C₂₋₃ alkenyl,
(6) —C₁₋₃ alkyl-R³,
(7) —C₂₋₃ alkenyl-R³, and
(8) —S(O)ₙ—R³, each R⁶ is independently selected from:
(1) —C₁₋₃ alkyl-R³, and
(2) —R³; and each n is independently selected from 0, 1 and 2, and provided that when R² is —R³, then R³ is not unsubstituted phenyl, unsubstituted imidazolyl, or unsubstituted morpholinyl.

4. The compound according to claim 3 selected from:

(1)
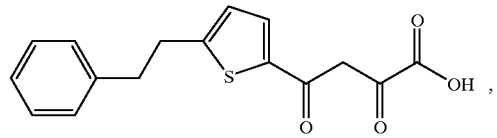

(2)
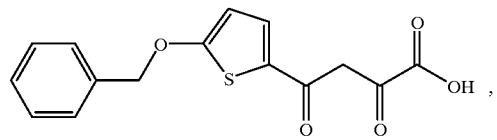

(3)
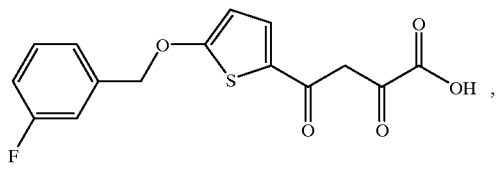

(4)
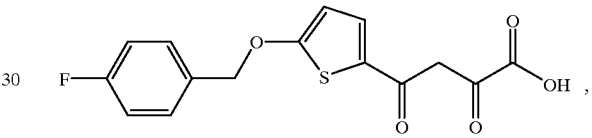

(5)
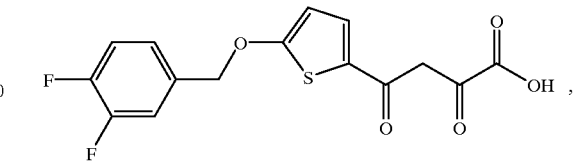

(6)
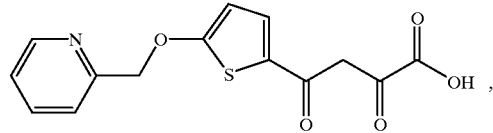

(7)
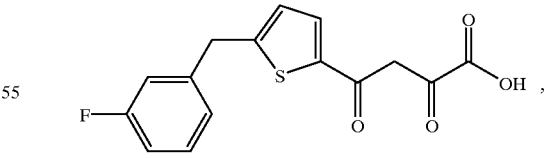

(8)
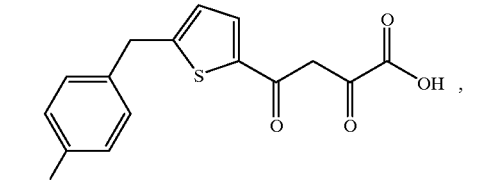

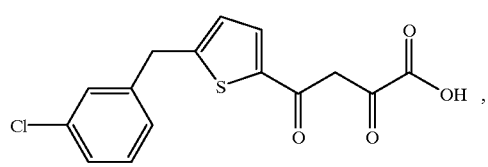
(9)
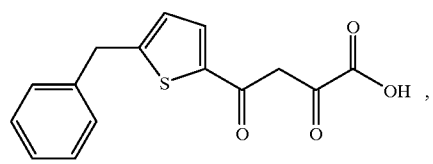
(10)
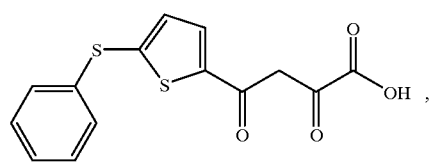
(11)
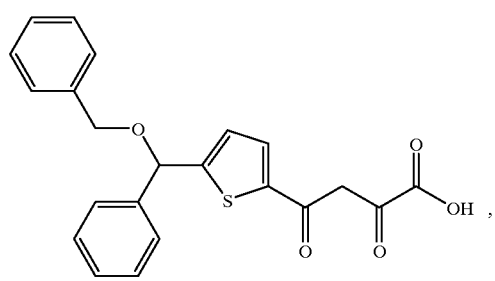
(12)
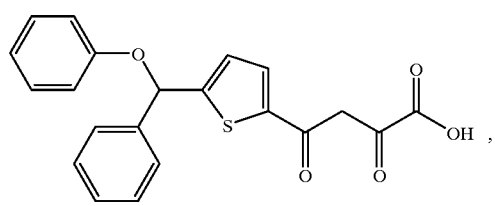
(13)
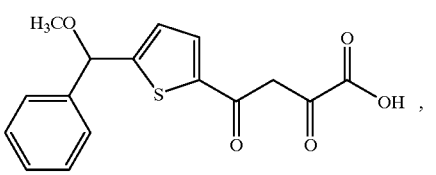
(14)
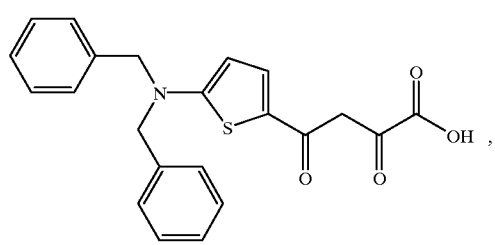
(15)
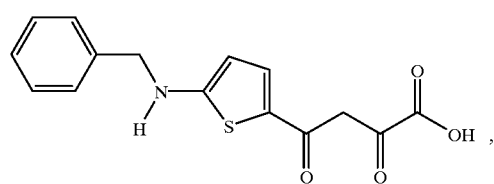
(16)
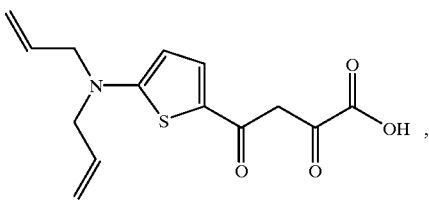
(17)
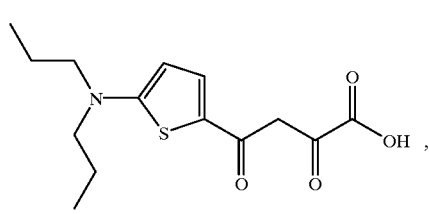
(18)
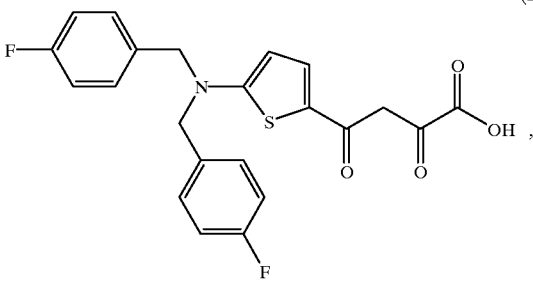
(19)
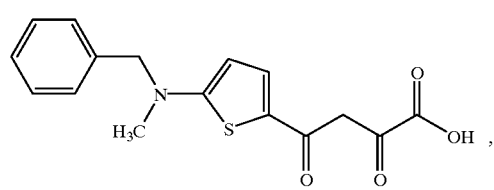
(20)
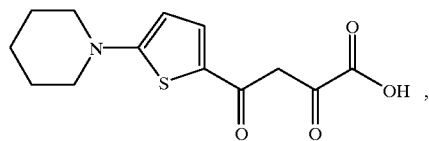
(21)
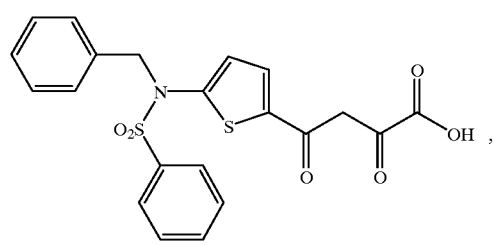
(22)

-continued

(23) [structure: benzyl-S-thiophene-C(O)-CH2-C(O)-C(O)OH]

(24) [structure: benzyl-S(O)2-thiophene-C(O)-CH2-C(O)-C(O)OH]

(25) [structure: phenyl-C(O)NH-thiophene-C(O)-CH2-C(O)-C(O)OH]

(26) [structure: phenyl-S(O)2-NH-thiophene-C(O)-CH2-C(O)-C(O)OH]

(27) [structure: phenyl-O-thiophene-C(O)-CH2-C(O)-C(O)OH], and

(28) [structure: 4-chlorobenzyl-thiophene-C(O)-CH2-C(O)-C(O)OH]

and tautomers and pharmaceutically acceptable salts thereof.

5. The compound according to claim 1 of structural formula:

[structure showing thiophene with $R^8$ at 2-position, $R^2$ at 5-position, and -C(O)-CH2-C(O)-C(O)OH at 3-position]

and tautomers and pharmaceutically acceptable salts thereof, wherein:

$R^2$ is selected from:
(1) —$R^3$,
(2) —$C_{1-6}$ alkyl substituted with $R^3$,
(3) —O—$R^6$,
(4) —S(O)n—$R^6$,
(5) —$C_{1-6}$ alkyl (O$R^6$)($R^4$),
(6) —$C_{1-6}$ alkyl (O$R^4$)($R^6$),
(7) —$C_{0-6}$ alkyl-N($R^4$)($R^6$),
(8) —$C_{1-6}$ alkyl S(O)n—$R^6$,
(9) —$C_{0-6}$ alkyl C(O)—$R^6$,
(10) —$C_{0-6}$ alkyl N$R^4$C(O)—$R^6$, and
(11) —$C_{0-6}$ alkyl-C(O)N($R^4$)($R^5$);

each $R^3$ is independently selected from:
(1) phenyl,
(2) substituted phenyl with 1, 2, or 3 substituents independently selected from:
 (a) halogen selected from —F, —Cl, and —Br,
 (b) $CH_3$,
 (c) methoxy-,
 (d) phenyl,
 (e) —$CF_3$,
 (f) —$OCF_3$,
 (g) —CN,
 (h) hydroxy,
 (i) phenyloxy, and
 (j) substituted phenyloxy with 1, 2, or 3 substituents selected from:
  (i) halogen selected from —F, —Cl, and —Br,
  (ii) —$CH_3$,
  (iii) —$CF_3$, and
  (iv) hydroxy;
(3) thienyl,
(4) pyridyl,
(5) imidazolyl,
(6) pyrrolyl,
(7) pyrazolyl,
(8) $C_{3-6}$ cycloalkyl,
(9) piperidinyl,
(10) morpholinyl,
(11) naphthyl,
(12) indolyl, and
(13) $C_{3-6}$ cycloalkyl fused with a phenyl ring;

each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$, and
(7) —S(O)$_n$—$R^3$, each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$, and
(8) —S(O)$_n$—$R^3$, each $R^6$ is independently selected from:
(1) —$C_{1-3}$ alkyl-$R^3$, and
(2) —$R^3$;

$R^8$ is selected from methyl and hydrogen; and each n is independently selected from 0, 1 and 2;

and provided that when $R^2$ is —$R^3$, then $R^3$ is not unsubstituted phenyl, unsubstituted imidazolyl, or unsubstituted morpholinyl.

6. The compound according to claim 5 selected from:

(1)
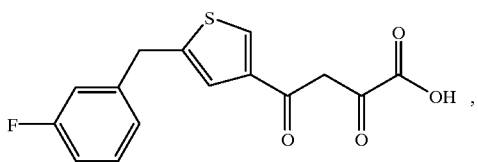

(2)
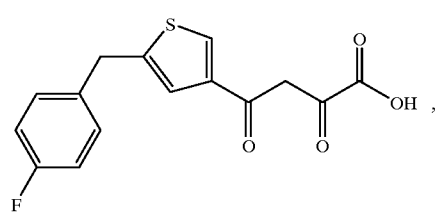

(3)
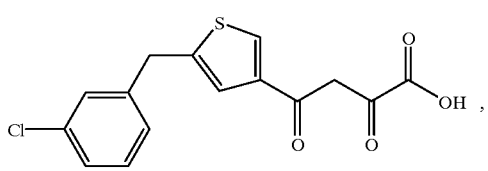

(4)
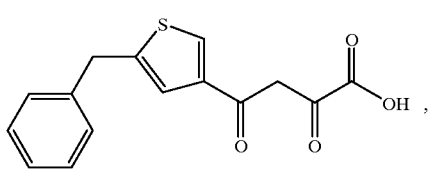

(5)
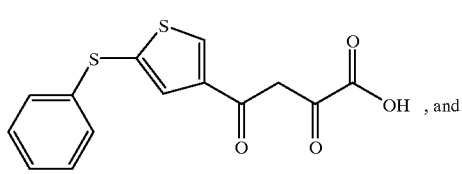, and (6)
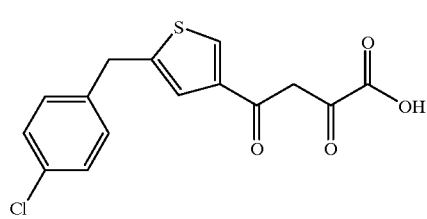

and tautomers and pharmaceutically acceptable salts thereof.

7. The compound according to claim 1 of structural formula:

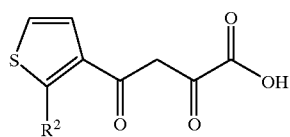

and tautomers and pharmaceutically acceptable salts thereof, wherein:

$R^2$ is selected from:
(1) —$R^3$,
(2) —$C_{1-6}$ alkyl substituted with $R^3$,
(3) —O—$R^6$,
(4) —S(O)n—$R^6$,
(5) —$C_{1-6}$ alkyl $(OR^6)(R^4)$,
(6) —$C_{1-6}$ alkyl $(OR^4)(R^6)$,
(7) —$C_{0-6}$ alkyl-$N(R^4)(R^6)$,
(8) —$C_{1-6}$ alkyl $S(O)n$—$R^6$,
(9) —$C_{0-6}$ alkyl $C(O)$—$R^6$,
(10) —$C_{0-6}$ alkyl $NR^4C(O)$—$R^6$, and
(11) —$C_{0-6}$ alkyl-$C(O)N(R^4)(R^5)$;

each $R^3$ is independently selected from:
(1) phenyl,
(2) substituted phenyl with 1, 2, or 3 substituents independently selected from:
  (a) halogen selected from —F, —Cl, and —Br,
  (b) $CH_3$,
  (c) methoxy-,
  (d) phenyl,
  (e) —$CF_3$,
  (f) —$OCF_3$,
  (g) —CN,
  (h) hydroxy,
  (i) phenyloxy, and
  (j) substituted phenyloxy with 1, 2, or 3 substituents selected from:
    (i) halogen selected from —F, —Cl, and —Br,
    (ii) —$CH_3$,
    (iii) —$CF_3$, and
    (iv) hydroxy;
(3) thienyl,
(4) pyridyl,
(5) imidazolyl,
(6) pyrrolyl,
(7) pyrazolyl,
(8) $C_{3-6}$ cycloalkyl,
(9) piperidinyl,
(10) morpholinyl,
(11) naphthyl,
(12) indolyl, and
(13) $C_{3-6}$ cycloalkyl fused with a phenyl ring;

each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$, and
(7) —$S(O)_n$—$R^3$, each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$, and
(8) —$S(O)_n$—$R^3$, each $R^6$ is independently selected from:
(1) —$C_{1-3}$ alkyl-$R^3$, and
(2) —$R^3$; and each n is independently selected from 0, 1 and 2;

and provided that when $R^2$ is —$R^3$, then $R^3$ is not unsubstituted phenyl, unsubstituted imidazolyl, or unsubstituted morpholinyl.

8. The compound according to claim 7 selected from:

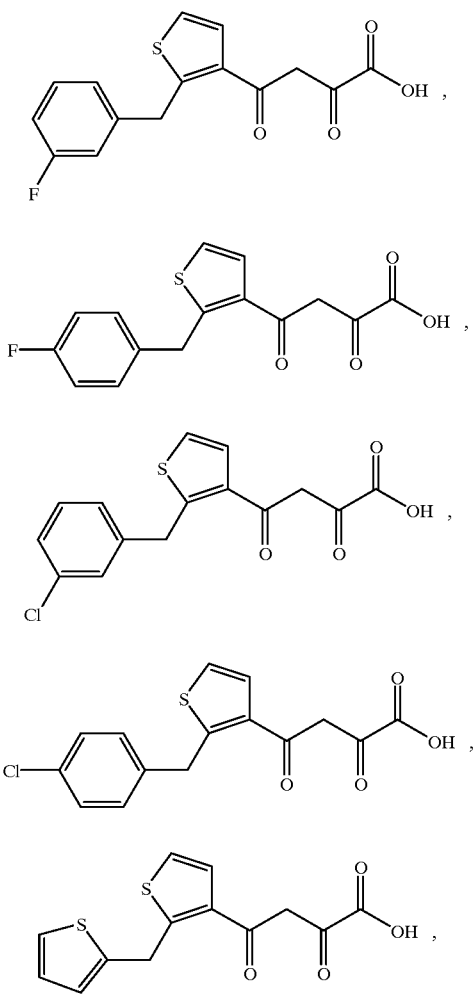

and tautomers and pharmaceutically acceptable salts thereof.

9. The compound according to claim 1 of structural formula:

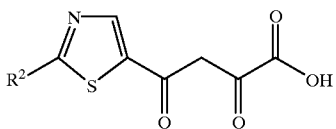

and tautomers and pharmaceutically acceptable salts thereof, wherein:

$R^2$ is selected from:
(1) —$R^3$,
(2) —$C_{1-6}$ alkyl substituted with $R^3$,
(3) —O—$R^6$,
(4) —S(O)n—$R^6$,
(5) —$C_{1-6}$ alkyl (O$R^6$)($R^4$),
(6) —$C_{1-6}$ alkyl (O$R^4$)($R^6$),
(7) —$C_{0-6}$ alkyl-N($R^4$)($R^6$),
(8) —$C_{1-6}$ alkyl S(O)n—$R^6$,
(9) —$C_{0-6}$ alkyl C(O)—$R^6$,
(10) —$C_{0-6}$ alkyl N$R^4$C(O)—$R^6$, and
(11) —$C_{0-6}$ alkyl-C(O)N($R^4$)($R^5$);

each $R^3$ is independently selected from:
(1) phenyl,
(2) substituted phenyl with 1, 2, or 3 substituents independently selected from:
(a) halogen selected from —F, —Cl, and —Br,
(b) $CH_3$,
(c) methoxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen selected from —F, —Cl, and —Br,
(ii) —$CH_3$,
(iii) —$CF_3$, and
(iv) hydroxy;
(3) thienyl,
(4) pyridyl,
(5) imidazolyl,
(6) pyrrolyl,
(7) pyrazolyl,
(8) $C_{3-6}$ cycloalkyl,
(9) piperidinyl,
(10) morpholinyl,
(11) naphthyl,
(12) indolyl, and
(13) $C_{3-6}$ cycloalkyl fused with a phenyl ring;

each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$, and
(7) —S(O)$_n$—$R^3$, each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$, and
(8) —S(O)$_n$—$R^3$, each $R^6$ is independently selected from:
(1) —$C_{1-3}$ alkyl-$R^3$, and
(2) —$R^3$; and each n is independently selected from 0, 1 and 2;
and provided that when $R^2$ is —$R^3$, then $R^3$ is not unsubstituted phenyl.

10. The compound according to claim 9 selected from:

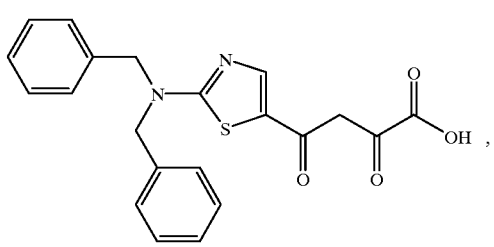

-continued
(2)
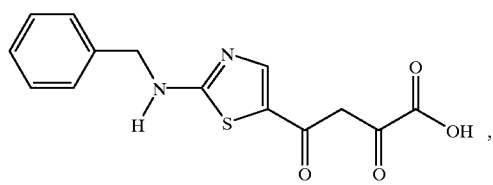
(3)
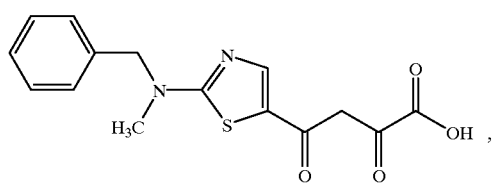
(4)
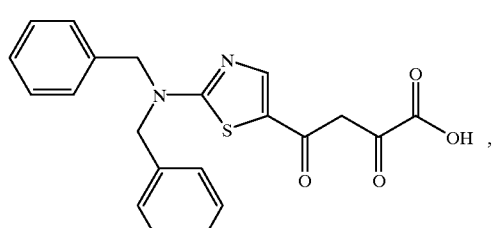
(5)
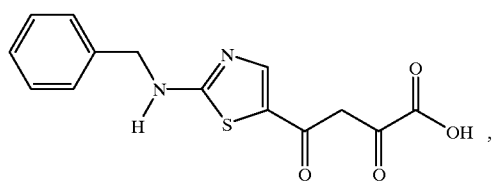
(6)
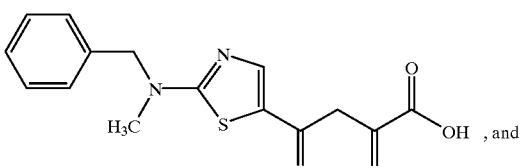 , and
(7)
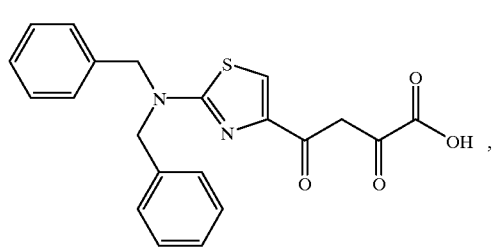
and tautomers and pharmaceutically acceptable salts thereof.
11. The compound according to claim 1 selected from:
(1)
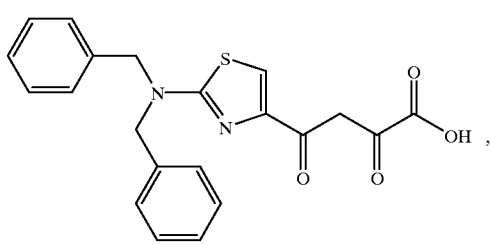
(2)
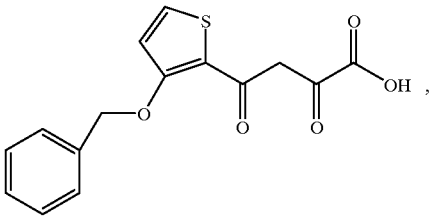
(3)
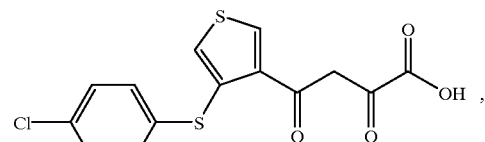
(4)
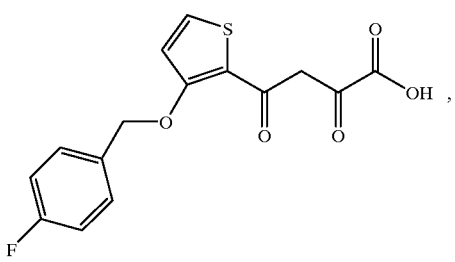
(5)
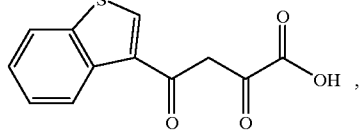
(6)
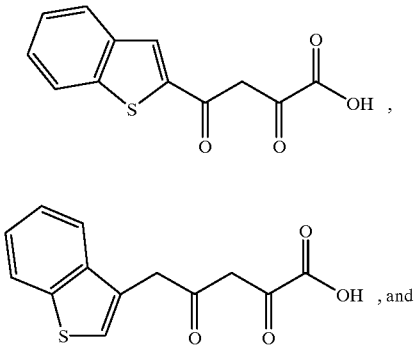
(7)

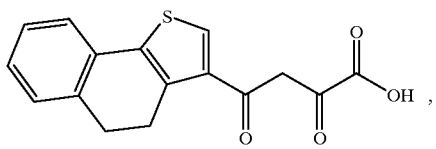

(8)

and tautomers and pharmaceutically acceptable salts thereof.

12. The compound according to claim 1 selected from:
(1) 2,4-dioxo-4-(5-phenethylthiophen-2-yl)butanoic acid,
(2) ethyl 2,4-dioxo-4-(5-phenethylthiophen-2-yl)butanoate,
(3) 2,4-dioxo-4-(5-benzyloxythiophen-2-yl)butanoic acid,
(4) 2,4-dioxo-4-[5-(3-fluorobenzyloxy)thiophen-2-yl]butanoic acid,
(5) 2,4-dioxo-4-[5-(4-fluorobenzyloxy)thiophen-2-yl]butanoic acid,
(6) 2,4-dioxo-4-[5-(3,4-difluorobenzyloxy)thiophen-2-yl]butanoic acid,
(7) 2,4-dioxo-4-[5-(pyridin-2-ylmethyloxy)thiophen-2-yl]butanoic acid,
(8) 2,4-dioxo-4-[5-(3-fluorobenzyl)thiophen-2-yl]butanoic acid,
(9) ethyl 2,4-dioxo-4-[5-(3-fluorobenzyl)thiophen-2-yl]butanoate,
(10) 2,4-dioxo-4-[5-(4-fluorobenzyl)thiophen-2-yl]butanoic acid,
(11) 2,4-dioxo-4-[5-(3-chlorobenzyl)thiophen-2-yl]butanoic acid,
(12) 2,4-dioxo-4-(5-benzylthiophen-2-yl)butanoic acid,
(13) 2,4-dioxo-4-(5-phenylsulfanylthiophen-2-yl)butanoic acid,
(14) 2,4-dioxo-4-[5-(3-fluorobenzyl)thiophen-3-yl]butanoic acid,
(15) 2,4-dioxo-4-[5-(4-fluorobenzyl)thiophen-3-yl]butanoic acid,
(16) 2,4-dioxo-4-[5-(3-chlorobenzyl)thiophen-3-yl]butanoic acid,
(17) 2,4-dioxo-4-(5-benzylthiophen-3-yl)butanoic acid,
(18) 2,4-dioxo-4-(2-phenylsulfanylthiophen-4-yl)butanoic acid,
(19) 2,4-dioxo-4-[2-(3-fluorobenzyl)thiophen-3-yl]butanoic acid,
(20) 2,4-dioxo-4-[2-(4-fluorobenzyl)thiophen-3-yl]butanoic acid,
(21) 2,4-dioxo-4-[2-(3-chlorobenzyl)thiophen-3-yl]butanoic acid,
(22) 2,4-dioxo-4-[5-(benzyloxy-phenylmethyl)thiophen-2-yl]butanoic acid,
(23) 2,4-dioxo-4-[5-(phenoxy-phenylmethyl)thiophen-2-yl]butanoic acid,
(24) 2,4-dioxo-4-[5-(methoxy-phenylmethyl)thiophen-2-yl]butanoic acid,
(25) 2,4-dioxo-4-(5-dibenzylaminothiophen-2-yl)butanoic acid,
(26) 2,4-dioxo-4-(5-benzylaminothiophen-2-yl)butanoic acid,
(27) 2,4-dioxo-4-(5-diallylaminothiophen-2-yl)butanoic acid,
(28) 2,4-dioxo-4-(5-di-n-propylaminothiophen-2-yl)butanoic acid,
(29) 2,4-dioxo-4-[5-(di-4-fluorobenzylamino)thiophen-2-yl]butanoic acid,
(30) 2,4-dioxo-4-[5-(N-benzyl-N-methylamino)thiophen-2-yl]butanoic acid,
(31) 2,4-dioxo-4-(5-piperidin-1-yl-thiophen-2-yl)butanoic acid,
(32) 2,4-dioxo-4-[5-(benzylbenzenesulfonylamino)thiophen-2-yl]butanoic acid,
(33) 2,4-dioxo-4-(2-dibenzylaminothiazol-5-yl)butanoic acid,
(34) 2,4-dioxo-4-(2-benzylaminothiazol-5-yl)butanoic acid,
(35) 2,4-dioxo-4-(2-N-benzyl-N-methylaminothiazol-5-yl)butanoic acid,
(36) 2,4-dioxo-4-(2-dibenzylaminothiazol-4-yl)butanoic acid, and tautomers and pharmaceutically acceptable salts thereof.

13. The compound according to claim 12 selected from:
(1) 2,4-dioxo-4-(5-phenethylthiophen-2-yl)butanoic acid,
(2) 2,4-dioxo-4-(5-benzyloxythiophen-2-yl)butanoic acid,
(3) 2,4-dioxo-4-[5-(3-fluorobenzyloxy)thiophen-2-yl]butanoic acid,
(4) 2,4-dioxo-4-[5-(4-fluorobenzyloxy)thiophen-2-yl]butanoic acid,
(5) 2,4-dioxo-4-[5-(3,4-difluorobenzyloxy)thiophen-2-yl]butanoic acid,
(6) 2,4-dioxo-4-[5-(pyridin-2-ylmethyloxy)thiophen-2-yl]butanoic acid,
(7) 2,4-dioxo-4-[5-(3-fluorobenzyl)thiophen-2-yl]butanoic acid,
(8) 2,4-dioxo-4-[5-(4-fluorobenzyl)thiophen-2-yl]butanoic acid,
(9) 2,4-dioxo-4-[5-(3-chlorobenzyl)thiophen-2-yl]butanoic acid,
(10) 2,4-dioxo-4-(5-benzylthiophen-2-yl)butanoic acid,
(11) 2,4-dioxo-4-(5-phenylsulfanylthiophen-2-yl)butanoic acid,
(12) 2,4-dioxo-4-[5-(3-fluorobenzyl)thiophen-3-yl]butanoic acid,
(13) 2,4-dioxo-4-[5-(4-fluorobenzyl)thiophen-3-yl]butanoic acid,
(14) 2,4-dioxo-4-[5-(3-chlorobenzyl)thiophen-3-yl]butanoic acid,
(15) 2,4-dioxo-4-(5-benzylthiophen-3-yl)butanoic acid,
(16) 2,4-dioxo-4-(2-phenylsulfanylthiophen-4-yl)butanoic acid,
(17) 2,4-dioxo-4-[2-(3-fluorobenzyl)thiophen-3-yl]butanoic acid,
(18) 2,4-dioxo-4-[2-(4-fluorobenzyl)thiophen-3-yl]butanoic acid,
(19) 2,4-dioxo-4-[2-(3-chlorobenzyl)thiophen-3-yl]butanoic acid,
(20) 2,4-dioxo-4-[5-(benzyloxy-phenylmethyl)thiophen-2-yl]butanoic acid,
(21) 2,4-dioxo-4-[5-(phenoxy-phenylmethyl)thiophen-2-yl]butanoic acid,
(22) 2,4-dioxo-4-[5-(methoxy-phenylmethyl)thiophen-2-yl]butanoic acid,

(23) 2,4-dioxo-4-(5-dibenzylaminothiophen-2-yl)butanoic acid,
(24) 2,4-dioxo-4-(5-benzylaminothiophen-2-yl)butanoic acid,
(25) 2,4-dioxo-4-(5-diallylaminothiophen-2-yl)butanoic acid,
(26) 2,4-dioxo-4-(5-di-n-propylaminothiophen-2-yl)butanoic acid,
(27) 2,4-dioxo-4-[5-(di-4-fluorobenzylamino)thiophen-2-yl]butanoic acid,
(28) 2,4-dioxo-4-[5-(N-benzyl-N-methylamino)thiophen-2-yl]butanoic acid,
(29) 2,4-dioxo-4-(5-piperidin-1-yl-thiophen-2-yl)butanoic acid,
(30) 2,4-dioxo-4-[5-(benzylbenzenesulfonylamino)thiophen-2-yl]butanoic acid,
(31) 2,4-dioxo-4-(2-dibenzylaminothiazol-5-yl)butanoic acid,
(32) 2,4-dioxo-4-(2-benzylaminothiazol-5-yl)butanoic acid,
(33) 2,4-dioxo-4-(2-N-benzyl-N-methylaminothiazol-5-yl)butanoic acid,
(34) 2,4-dioxo-4-(2-dibenzylaminothiazol-4-yl)butanoic acid,
and tautomers and pharmaceutically acceptable salts thereof.

14. The compound according to claim 13 selected from:
(1) 2,4-dioxo-4-[5-(3-chlorobenzyl)thiophen-2-yl]butanoic acid,
(2) 2,4-dioxo-4-[5-(3-fluorobenzyl)thiophen-3-yl]butanoic acid,
(3) 2,4-dioxo-4-[5-(4-fluorobenzyl)thiophen-3-yl]butanoic acid,
(4) 2,4-dioxo-4-[5-(3-chlorobenzyl)thiophen-3-yl]butanoic acid,
(5) 2,4-dioxo-4-(5-benzylthiophen-3-yl)butanoic acid,
(6) 2,4-dioxo-4-(2-phenylsulfanylthiophen-4-yl)butanoic acid, XII(4)
(7) 2,4-dioxo-4-[2-(3-chlorobenzyl)thiophen-3-yl]butanoic acid,
(8) 2,4-dioxo-4-[5-(benzyloxy-phenylmethyl)thiophen-2-yl]butanoic acid,
(9) 2,4-dioxo-4-[5-(phenoxy-phenylmethyl)thiophen-2-yl]butanoic acid,
(10) 2,4-dioxo-4-(5-dibenzylaminothiophen-2-yl)butanoic acid,
(11) 2,4-dioxo-4-(5-diallylaminothiophen-2-yl)butanoic acid,
(12) 2,4-dioxo-4-[5-(di-4-fluorobenzylamino)thiophen-2-yl]butanoic acid,
(13) 2,4-dioxo-4-[5-(N-benzyl-N-methylamino)thiophen-2-yl]butanoic acid,
(14) 2,4-dioxo-4-(2-dibenzylaminothiazol-5-yl)butanoic acid, and
(15) 2,4-dioxo-4-(2-N-benzyl-N-methylaminothiazol-5-yl)butanoic acid,
and tautomers and pharmaceutically acceptable salts thereof.

15. A pharmaceutical composition useful for inhibiting HIV integrase, comprising an effective amount of a compound according to claim 1 and a pharmaceutically acceptable carrier.

16. The pharmaceutical composition of claim 15, useful for treating infection by HIV, or for treating AIDS or ARC.

17. A pharmaceutical composition comprising a therapeutically effective amount of a compound of structural formula (I):

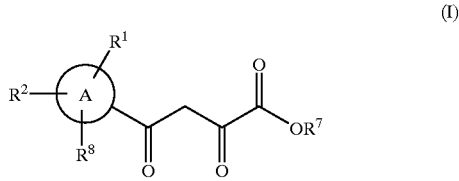

or tautomers or pharmaceutically acceptable salts thereof, in combination with a therapeutically effective amount of an AIDS treatment agent selected from
(1) an AIDS antiviral agent,
(2) an anti-infective agent, and
(3) an immunomodulator; wherein
A is a five-membered heteroaromatic ring containing 1 sulfur atom and 0 or 1 nitrogen atoms and substituted on carbon by $R^1$, $R^2$ and $R^8$; the heteroaromatic ring may optionally be fused with a phenyl ring or a $C_{4-6}$ cycloalkyl ring, or with two six membered rings to form:

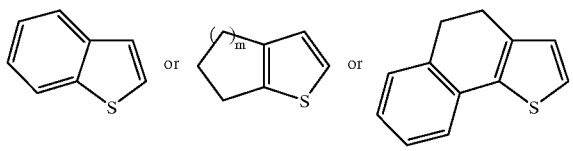

$R^1$ is selected from:
(1) —H,
(2) —$C_{1-5}$ alkyl,
(3) —$CF_3$,
(4) -halo,
(5) —$NO_2$,
(6) —$N(R^4)(R^5)$,
(7) —$R^6$,
(8) —$C_{2-5}$ alkenyl-$R^3$,
(9) —$C_{2-5}$ alkynyl-$R^3$,
(10) —O—$R^6$,
(11) —O—$C_{1-6}$ alkyl, and
(12) —$C(O)CH_2C(O)C(O)OR^7$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —S(O)n—$R^6$,
(8) —$C_{1-6}$ alkyl ($OR^6$)($R^4$),
(9) —$C_{1-6}$ alkyl ($OR^4$)($R^6$),
(10) —$C_{0-6}$ alkyl-$N(R^4)(R^6)$,
(11) —$C_{1-6}$ alkyl S(O)n—$R^6$,
(12) —$C_{0-6}$ alkyl C(O)—$R^6$,
(13) —$C_{0-6}$ alkyl C(S)—$R^6$,
(14) —$C_{0-6}$ alkyl $NR^4C(O)$—$R^6$, and
(15) —$C_{0-6}$ alkyl-$C(O)N(R^4)(R^5)$;

each $R^3$ is independently selected from:
(1) a 5 or 6 membered aromatic or heteroaromatic ring, containing 0, 1, 2, 3, or 4 heteroatoms selected from oxygen, nitrogen and sulfur, unsubstituted or substituted on a nitrogen or carbon atom by 1 to 5 substituents selected from:

(a) halogen,
(b) $C_{1-6}$ alkyl,
(c) $C_{1-6}$ alkyloxy-,
(d) phenyl,
(e) —$CF_3$,
(f) —$OCF_3$,
(h) hydroxy,
(i) phenyloxy, and
(j) substituted phenyloxy with 1, 2, or 3 substituents selected from:
   (i) halogen,
   (ii) $C_{1-6}$ alkyl,
   (iii) —$CF_3$, and
   (iv) hydroxy;
(2) a 3 to 6 membered saturated ring containing 0 or 1 heteroatoms selected from oxygen, nitrogen or sulfur, unsubstituted or substituted with 0 to 5 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(3) unsubstituted or substituted hexahydrothieno[3,4-d]imidazolyl with one or two substituents selected from:
(a) oxo,
(b) halogen,
(c) $C_{1-6}$ alkyl,
(d) $C_{1-6}$ alkyloxy-,
(e) —$CF_3$,
(f) —$OCF_3$,
(g) —CN, and
(h) hydroxy;
(4) a 5 or 6 membered aromatic or heteroaromatic ring, containing 0, 1, or 2 heteroatoms selected from oxygen, nitrogen and sulfur, fused with a phenyl ring;
wherein the ring system is unsubstituted or substituted on a nitrogen or carbon atom by 1 to 3 substituents selected from:
   (a) -halogen,
   (b) —$C_{1-6}$ alkyl,
   (c) —$C_{1-6}$ alkyloxy-,
   (d) —$CF_3$,
   (e) —$OCF_3$,
   (f) —CN, and
   (g) -hydroxy;
(5) a 3 to 6 membered saturated ring containing 0 or 1 heteroatoms selected from oxygen, nitrogen or sulfur, fused with a phenyl ring, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:

(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;

each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —C(O)—$R^3$;

each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —C(O)—$R^3$;

each $R^6$ is independently selected from:
(1) —$C_{1-3}$ alkyl-$R^3$, and
(2) —$R^3$;

$R^7$ is selected from:
(1) —H, and
(2) $C_{1-6}$ alkyl;

$R^8$ is selected from:
(1) —H, and
(2) $C_{1-6}$ alkyl-oxy-, and
(3) $C_{1-6}$ alkyl-;

each n is independently selected from 0, 1 and 2, and
each m is independently selected from 0, 1, and 2.

18. The composition of claim 17 wherein the antiviral agent is an HIV protease inhibitor.

19. The composition of claim 18 wherein the HIV protease inhibitor is N-(2(R)-hydroxy-1-(S)-indanyl)-2(R)-phenylmethyl-4(S)-hydroxy-5-(1-(4-(3-pyridylmethyl)-2 (S)-N'-(t-butylcarboxamido)-piperazinyl))-pentaneamide or a pharmaceutically acceptable salt thereof.

20. A pharmaceutical composition made by combining the compound of claim 1 and a pharmaceutically acceptable carrier.

21. A process for making a pharmaceutical composition comprising combining a compound of claim 1 and a pharmaceutically acceptable carrier.

22. A method of inhibiting HIV integrase, comprising the administration to a mammal in need of such treatment a therapeutically effective amount of a compound of structural formula (I):

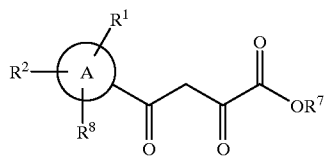

or tautomers or pharmaceutically acceptable salts thereof, wherein:

A is a five-membered heteroaromatic ring containing 1 sulfur atom and 0 or 1 nitrogen atoms and substituted on carbon by $R^1$, $R^2$ and $R^8$; the heteroaromatic ring may optionally be fused with a phenyl ring or a $C_{4-6}$ cycloalkyl ring, or with two six membered rings to form:

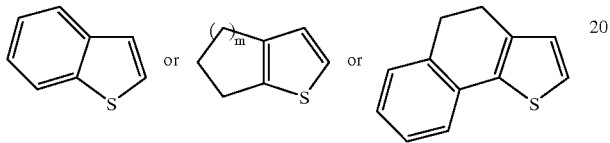

$R^1$ is selected from:
(1) —H,
(2) —$C_{1-5}$ alkyl,
(3) —$CF_3$,
(4) -halo,
(5) —$NO_2$,
(6) —$N(R^4)(R^5)$,
(7) —$R^6$,
(8) —$C_{2-5}$ alkenyl-$R^3$,
(9) —$C_{2-5}$ alkynyl-$R^3$,
(10) —O—$R^6$,
(11) —O—$C_{1-6}$ alkyl, and
(12) —$C(O)CH_2C(O)C(O)OR^7$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$S(O)n$—$R^6$,
(8) —$C_{1-6}$ alkyl $(OR^6)(R^4)$,
(9) —$C_{1-6}$ alkyl $(OR^4)(R^6)$,
(10) —$C_{0-6}$ alkyl-$N(R^4)(R^5)$,
(11) —$C_{1-6}$ alkyl $S(O)n$—$R^6$,
(12) —$C_{0-6}$ alkyl $C(O)$—$R^6$,
(13) —$C_{0-6}$ alkyl $C(S)$—$R^6$,
(14) —$C_{0-6}$ alkyl $NR^4C(O)$—$R^6$, and
(15) —$C_{0-6}$ alkyl-$C(O)N(R^4)(R^5)$;

each $R^3$ is independently selected from:
(1) a 5 or 6 membered aromatic or heteroaromatic ring, containing 0, 1, 2, 3, or 4 heteroatoms selected from oxygen, nitrogen and sulfur, unsubstituted or substituted on a nitrogen or carbon atom by 1 to 5 substituents selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;

(2) a 3 to 6 membered saturated ring containing 0 or 1 heteroatoms selected from oxygen, nitrogen or sulfur, unsubstituted or substituted with 0 to 5 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;

(3) unsubstituted or substituted hexahydrothieno[3,4-d]imidazolyl with one or two substituents selected from:
(a) oxo,
(b) halogen,
(c) $C_{1-6}$ alkyl,
(d) $C_{1-6}$ alkyloxy-,
(e) —$CF_3$,
(f) —$OCF_3$,
(g) —CN, and
(h) hydroxy;

(4) a 5 or 6 membered aromatic or heteroaromatic ring, containing 0, 1, or 2 heteroatoms selected from oxygen, nitrogen and sulfur, fused with a phenyl ring;
wherein the ring system is unsubstituted or substituted on a nitrogen or carbon atom by 1 to 3 substituents selected from:
(a) -halogen,
(b) —$C_{1-6}$ alkyl,
(c) —$C_{1-6}$ alkyloxy-,
(d) —$CF_3$,
(e) —$OCF_3$,
(f) —CN, and
(g) -hydroxy;

(5) a 3 to 6 membered saturated ring containing 0 or 1 heteroatoms selected from oxygen, nitrogen or sulfur, fused with a phenyl ring, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;

(6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:
(a) halogen,
(b) $C_{1-6}$ alkyl,
(c) $C_{1-6}$ alkyloxy-,
(d) —$CF_3$,
(e) —$OCF_3$, (f) —CN,
(g) =O, and
(h) hydroxy;

each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$;

each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$;

each $R^6$ is independently selected from:
(1) —$C_{1-3}$ alkyl-$R^3$, and
(2) —$R_3$;

$R^7$ is selected from:
(1) —H, and
(2) $C_{1-6}$ alkyl;

$R^8$ is selected from:
(1) —H, and
(2) $C_{1-6}$ alkyl-oxy-, and
(3) $C_{1-6}$ alkyl-;

each n is independently selected from 0, 1 and 2, and
each m is independently selected from 0, 1, and 2.

23. A method of treating infection by HIV, or of treating AIDS or ARC, comprising the administration to a mammal in need of such treatment a therapeutically effective amount of a compound of structural formula (I):

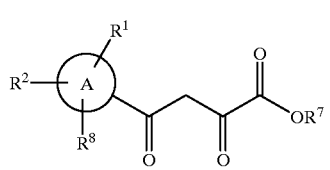
(I)

or tautomers or pharmaceutically acceptable salts thereof, wherein:

A is a five-membered heteroaromatic ring containing 1 sulfur atom and 0 or 1 nitrogen atoms and substituted on carbon by $R^1$, $R^2$ and $R^8$; the heteroaromatic ring may optionally be fused with a phenyl ring or a $C_{4-6}$ cycloalkyl ring, or with two six membered rings to form:

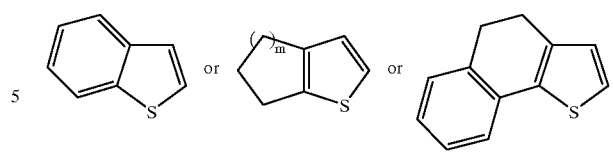

$R^1$ is selected from:
(1) —H,
(2) —$C_{1-5}$ alkyl,
(3) —$CF_3$,
(4) -halo,
(5) —$NO_2$,
(6) —$N(R^4)(R^5)$,
(7) —$R^6$,
(8) —$C_{2-5}$ alkenyl-$R^3$,
(9) —$C_{2-5}$ alkynyl-$R^3$,
(10) —O—$R^6$,
(11) —O—$C_{1-6}$ alkyl, and
(12) —$C(O)CH_2C(O)C(O)OR^7$;

$R^2$ is selected from:
(1) —H,
(2) —$R^3$,
(3) —$C_{1-6}$ alkyl,
(4) —$C_{1-6}$ alkyl substituted with $R^3$,
(5) —O—$R^6$,
(6) —O—$C_{1-6}$ alkyl-$OR^6$,
(7) —$S(O)n$—$R^6$,
(8) —$C_{1-6}$ alkyl $(OR^6)(R^4)$,
(9) —$C_{1-6}$ alkyl $(OR^4)(R^6)$,
(10) —$C_{0-6}$ alkyl-$N(R^4)(R^6)$,
(11) —$C_{1-6}$ alkyl $S(O)n$—$R^6$,
(12) —$C_{0-6}$ alkyl $C(O)$—$R^6$,
(13) —$C_{0-6}$ alkyl $C(S)$—$R^6$,
(14) —$C_{0-6}$ alkyl $NR^4C(O)$—$R^6$, and
(15) —$C_{0-6}$ alkyl-$C(O)N(R^4)(R^5)$;

each $R^3$ is independently selected from:
(1) a 5 or 6 membered aromatic or heteroaromatic ring, containing 0, 1, 2, 3, or 4 heteroatoms selected from oxygen, nitrogen and sulfur, unsubstituted or substituted on a nitrogen or carbon atom by 1 to 5 substituents selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;
(2) a 3 to 6 membered saturated ring containing 0 or 1 heteroatoms selected from oxygen, nitrogen or sulfur, unsubstituted or substituted with 0 to 5 substituents selected from:
(a) halogen,
(b) $C_{1-6}$ alkyl,
(c) $C_{1-6}$ alkyloxy-,
(d) —$CF_3$, (e) —OCF$_3$,
(f) —CN,
(g) =O, and
(h) hydroxy;
(3) unsubstituted or substituted hexahydrothieno[3,4-d]imidazolyl with one or two substituents selected from:
 (a) oxo,
 (b) halogen,
 (c) C$_{1-6}$ alkyl,
 (d) C$_{1-6}$ alkyloxy-,
 (e) —C$_3$,
 (f) —OCF$_3$,
 (g) —CN, and
 (h) hydroxy;
(4) a 5 or 6 membered aromatic or heteroaromatic ring, containing 0, 1, or 2 heteroatoms selected from oxygen, nitrogen and sulfur, fused with a phenyl ring;
 wherein the ring system is unsubstituted or substituted on a nitrogen or carbon atom by 1 to 3 substituents selected from:
  (a) -halogen,
  (b) —C$_{1-6}$ alkyl,
  (c) —C$_{1-6}$ alkyloxy-,
  (d) —CF$_3$,
  (e) —OCF$_3$,
  (f) —CN, and
  (g) -hydroxy;
(5) a 3 to 6 membered saturated ring containing 0 or 1 heteroatoms selected from oxygen, nitrogen or sulfur, fused with a phenyl ring, unsubstituted or substituted with 1 or 2 substituents selected from:
 (a) halogen,
 (b) C$_{1-6}$ alkyl,
 (c) C$_{1-6}$ alkyloxy-,
 (d) —CF$_3$,
 (e) —OCF$_3$,
 (f) —CN,
 (g) =O, and
 (h) hydroxy;
(6) a 5 to 6 membered ring containing 0, 1 or 2 heteroatoms selected from oxygen, nitrogen or sulfur, containing 2 or 3 double bonds, unsubstituted or substituted with 1 or 2 substituents selected from:
 (a) halogen,
 (b C$_{1-6}$ alkyl,
 (c) C$_{1-6}$ alkyloxy-,
 (d) —CF$_3$,
 (e) —OCF$_3$,
 (f) —CN,
 (g) =O, and
 (h) hydroxy;
each R$^4$ is independently selected from:
 (1) —H,
 (2) —C$_{1-3}$ alkyl,
 (3) —C$_3$,
 (4) —R$^3$,
 (5) —C$_{2-3}$ alkenyl,
 (6) —C$_{1-3}$ alkyl-R$^3$,
 (7) —C$_{2-3}$ alkenyl-R$^3$,
 (8) —S(O)$_n$—R$^3$, and
 (9) —C(O)—R$^3$;
each R$^5$ is independently selected from:
 (1) —H,
 (2) —C$_{1-3}$ alkyl,
 (3) —CF$_3$,
 (4) —R$^3$,
 (5) —C$_{2-3}$ alkenyl,
 (6) —C$_{1-3}$ alkyl-R$^3$,
 (7) —C$_{2-3}$ alkenyl-R$^3$,
 (8) —S(O)$_n$—R$^3$, and
 (9) —C(O)—R$^3$;
each R$^6$ is independently selected from:
 (1) —C$_{1-3}$ alkyl-R$^3$, and
 (2) —R$^3$;
R$^7$ is selected from:
 (1) —H, and
 (2) C$_{1-6}$ alkyl;
R$^8$ is selected from:
 (1) —H, and
 (2) C$_{1-6}$ alkyl-oxy-, and
 (3) C$_{1-6}$ alkyl-;
each n is independently selected from 0, 1 and 2, and
each m is independently selected from 0, 1, and 2.

24. A compound of structural formula (I):

(I)

and tautomers and pharmaceutically acceptable salts thereof, wherein:
A is selected from:
 (1) thienyl,
 (2) thiazolyl, (3)

(4)
, and (5)

R$^1$ is selected from:
 (1) —H,
 (2) —CH$_3$,
 (3) —CF$_3$,
 (4) -halo,
 (5) —NO$_2$,
 (6) —N(R$^4$)(R$^5$),
 (7) -phenyl,
 (8) substituted phenyl substituted with 1 or 2 substituents independently selected from:
  (a) halogen,
  (b) C$_{1-6}$ alkyl,
  (c) C$_{1-6}$ alkyloxy-, (d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;
(9) phenyl C$_{1-3}$ alkyl-,
(10) substituted phenyl C$_{1-3}$ alkyl-substituted with 1 or 2 substituents independently selected from:
  (a) halogen,
  (b) C$_{1-6}$ alkyl,
  (c) C$_{1-6}$ alkyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen,
    (ii) C$_{1-6}$ alkyl,
    (iii) —CF$_3$, and
    (iv) hydroxy;
(11) —C$_{2-5}$ alkenyl-R$^3$,
(12) —C$_{2-5}$ alkynyl-R$^3$, and
(13) —C(O)CH$_2$C(O)C(O)OR$^7$;
R$^2$ is selected from:
  (1) —R$^3$,
  (2) —C$_{1-6}$ alkyl substituted with R$^3$,
  (3) —O—R$^6$,
  (4) —O—C$_{1-6}$ alkyl-OR$^6$,
  (5) —S(O)n—R$^6$,
  (6) —C$_{1-6}$ alkyl (OR$^6$)(R$^4$),
  (7) —C$_{1-6}$ alkyl (OR$^4$)(R$^6$),
  (8) —C$_{0-6}$ alkyl-N(R$^4$)(R$^6$),
  (9) —C$_{1-6}$ alkyl S(O)n—R$^6$,
  (10) —C$_{0-6}$ alkyl C(O)—R$^6$,
  (11) —C$_{0-6}$ alkyl C(S)—R$^6$,
  (12) —C$_{0-6}$ alkyl NR$^4$C(O)—R$^6$, and
  (13) —C$_{0-6}$ alkyl-C(O)N(R$^4$)(R$^5$);
each R$^3$ is independently selected from:
  (1) phenyl;
  (2) substituted phenyl with 1, 2, or 3 substituents independently selected from:
    (a) halogen,
    (b) C$_{1-6}$ alkyl,
    (c) C$_{1-6}$ alkyloxy-,
    (d) phenyl,
    (e) —CF$_3$,
    (f) —OCF$_3$,
    (g) —CN,
    (h) hydroxy,
    (i) phenyloxy, and
    (j) substituted phenyloxy with 1, 2, or 3 substituents selected from:
      (i) halogen,
      (ii) C$_{1-6}$ alkyl,
      (iii) —CF$_3$, and
      (iv) hydroxy;
  (3) thienyl;
  (4) substituted thienyl substituted on a carbon atom with one or two substituents independently selected from:
    (a) halogen,
    (b) C$_{1-6}$ alkyl,
    (c) C$_{1-6}$ alkyloxy-,
    (d) phenyl,
    (e) —CF$_3$,
    (f) —OCF$_3$,
    (g) —CN,
    (h) hydroxy,
    (i) phenyloxy, and
    (j) substituted phenyloxy with 1, 2, or 3 substituents selected from:
      (i) halogen,
      (ii) C$_{1-6}$ alkyl,
      (iii) —CF$_3$, and
      (iv) hydroxy;
  (5) pyridyl;
  (6) substituted pyridyl substituted on a carbon atom with one or two substituents independently selected from:
    (a) halogen,
    (b) C$_{1-6}$ alkyl,
    (c) C$_{1-6}$ alkyloxy-,
    (d) phenyl,
    (e) —CF$_3$,
    (f) —OCF$_3$,
    (g) —CN,
    (h) hydroxy,
    (i) phenyloxy, and
    (j) substituted phenyloxy with 1, 2, or 3 substituents selected from:
      (i) halogen,
      (ii) C$_{1-6}$ alkyl,
      (iii) —CF$_3$, and
      (iv) hydroxy;
  (7) substituted imidazolyl substituted on a carbon atom with one or two substituents independently selected from:
    (a) halogen,
    (b) C$_{1-6}$ alkyl,
    (c) C$_{1-6}$ alkyloxy-,
    (d) phenyl,
    (e) —CF$_3$,
    (f) —OCF$_3$,
    (g) —CN,
    (h) hydroxy,
    (i) phenyloxy, and
    (j) substituted phenyloxy with 1, 2, or 3 substituents selected from:
      (i) halogen,
      (ii) C$_{1-6}$ alkyl,
      (iii) —CF$_3$, and
      (iv) hydroxy;
  (8) pyrrolyl;
  (9) substituted pyrrolyl substituted on a carbon atom with one or two substituents independently selected from:
    (a) halogen,
    (b) C$_{1-6}$ alkyl,
    (c) C$_{1-6}$ alkyloxy-,
    (d) phenyl,
    (e) —CF$_3$,
    (f) —OCF$_3$,
    (g) —CN,
    (h) hydroxy, (i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;
(10) pyrazolyl;
(11) substituted pyrazolyl substituted on a carbon atom with one or two substituents independently selected from:
(a) halogen,
(b) $C_{1-6}$ alkyl,
(c) $C_{1-6}$ alkyloxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen,
(ii) $C_{1-6}$ alkyl,
(iii) —$CF_3$, and
(iv) hydroxy;
(12) $C_{3-6}$ cycloalkyl;
(13) substituted $C_{3-6}$ cycloalkyl with 1 or 2 substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(14) piperidinyl;
(15) substituted piperidinyl substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
(16) substituted morpholinyl substituted at a carbon or nitrogen atom with 1 or 2 substituents independently selected from:
(a) halogen,
(b) $C_{1-6}$ alkyl, (c) $C_{1-6}$ alkyloxy-,
(d) —$CF_3$,
(e) —$OCF_3$,
(f) —CN,
(g) =O, and
(h) hydroxy;
(17) naphthyl,
(18) substituted naphthyl with 1, 2, or 3 substituents independently selected from:
(a) -halogen,
(b) —$C_{1-6}$ alkyl,
(c) $C_{1-6}$ alkyloxy-,
(d) —$CF_3$,
(e) —$OCF_3$,
(f) —CN, and
(g) -hydroxy;
(19) indolyl;
(20) substituted indolyl substituted on a carbon atom with one or two substituents independently selected from:
(a) -halogen,
(b) —$C_{1-6}$ alkyl,
(c) $C_{1-6}$ alkyloxy-,
(d) —$CF_3$,
(e) —$OCF_3$,
(f) —CN, and
(g) -hydroxy;
(21) $C_{3-6}$ cycloalkyl fused with a phenyl ring
(22) substituted $C_{3-6}$ cycloalkyl fused with a phenyl ring substituted on a carbon atom with one or two substituents independently selected from:
(a) halogen,
(b) $C_{1-6}$ alkyl,
(c) $C_{1-6}$ alkyloxy-,
(d) —$CF_3$,
(e) —$OCF_3$,
(f) —CN,
(g) =O, and
(h) hydroxy;
each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$;
each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$,
(8) —$S(O)_n$—$R^3$, and
(9) —$C(O)$—$R^3$;
each $R^6$ is independently selected from:
(1) —$C_{1-3}$ alkyl-$R^3$, and
(2) —$R^3$;
$R^7$ is H;
$R^8$ is selected from hydrogen, methyl and methoxy;
each n is independently selected from 0, 1 and 2, and
each m is independently selected from 0, 1, and 2;
and provided that when A is thienyl or thiazolyl and $R^2$ is —$R^3$ wherein $R^3$ is unsubstituted phenyl, then $R^1$ is not
(1) —H or
(2) —$CH_3$.
25. The compound according to claim 24, and tautomers and pharmaceutically acceptable salts thereof, wherein each $R^3$ is independently selected from:
(1) substituted phenyl with 1, 2, or 3 substituents independently selected from:
(a) halogen,
(b) $C_{1-6}$ alkyl,
(c) $C_{1-6}$ alkyloxy-,
(d) phenyl,
(e) —$CF_3$, (f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;
(2) thienyl;
(3) substituted thienyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;
(4) pyridyl;
(5) substituted pyridyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;
(6) substituted imidazolyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;
(7) pyrrolyl;
(8) substituted pyrrolyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;
(9) pyrazolyl;
(10) substituted pyrazolyl substituted on a carbon atom with one or two substituents independently selected from:
(a) halogen,
(b) C$_{1-6}$ alkyl,
(c) C$_{1-6}$ alkyloxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;
(11) C$_{3-6}$ cycloalkyl;
(12) substituted C$_{3-6}$ cycloalkyl with 1 or 2 substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy;
(13) piperidinyl;
(14) substituted piperidinyl substituted on a carbon atom with one or two substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN,
(g) =O, and
(h) hydroxy;
(15) substituted morpholinyl substituted at a carbon or nitrogen atom with 1 or 2 substituents independently selected from:
(a) halogen,
(b) C$_{1-6}$ alkyl,
(c) C$_{1-6}$ alkyloxy-,
(d) —CF$_3$,
(e) —OCF$_3$,
(f) —CN, (g) =O, and
(h) hydroxy;
(16) naphthyl,
(17) substituted naphthyl with 1, 2, or 3 substituents independently selected from:
  (a) -halogen,
  (b) —$C_{1-6}$ alkyl,
  (c) $C_{1-6}$ alkyloxy-,
  (d) —$CF_3$,
  (e) —$OCF_3$,
  (f) —CN, and
  (g) -hydroxy;
(18) indolyl;
(19) substituted indolyl substituted on a carbon atom with one or two substituents independently selected from:
  (a) -halogen,
  (b) —$C_{1-6}$ alkyl,
  (c) $C_{1-6}$ alkyloxy-,
  (d) —$CF_3$,
  (e) —$OCF_3$,
  (f) —CN, and
  (g) -hydroxy;
(20) $C_{3-6}$ cycloalkyl fused with a phenyl ring
(21) substituted $C_{3-6}$ cycloalkyl fused with a phenyl ring substituted on a carbon atom with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy.

26. The compound according to claim 25, and tautomers and pharmaceutically acceptable salts thereof, wherein
A is selected from:
  (1) thienyl,
  (2) thiazolyl,

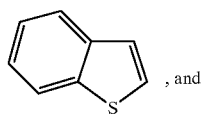
, and (3)

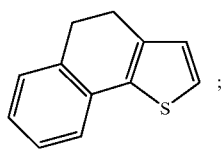
; (4)

$R^1$ is selected from:
  (1) —H,
  (2) —$CH_3$,
  (3) —$CF_3$,
  (4) -halo,
  (5) —$NO_2$,
  (6) —N($R^4$)($R^5$),
  (7) -phenyl,
  (8) substituted phenyl substituted with 1 or 2 substituents independently selected from:
    (a) halo,
    (b) methyl, and
    (c) methoxy,
  (9) phenyl $C_{1-3}$ alkyl-,
  (10) substituted phenyl $C_{1-3}$ alkyl-substituted with 1 or 2 substituents independently selected from:
    (a) halo,
    (b) methyl, and
    (c) methoxy, and
  (11) —$C_{2-5}$ alkenyl-$R^3$;
$R^2$ is selected from:
  (1) —$R^3$,
  (2) —$C_{1-6}$ alkyl substituted with $R^3$,
  (3) —O—$R^6$,
  (4) —S(O)n—$R^6$,
  (5) —$C_{1-6}$ alkyl ($OR^6$)($R^4$),
  (6) —$C_{1-6}$ alkyl ($OR^4$)($R^6$),
  (7) —$C_{0-6}$ alkyl-N($R^4$)($R^6$),
  (8) —$C_{1-6}$ alkyl S(O)n—$R^6$,
  (9) —$C_{0-6}$ alkyl C(O)—$R^6$,
  (10) —$C_{0-6}$ alkyl $NR^4$C(O)—$R^6$, and
  (11) —$C_{0-6}$ alkyl-C(O)N($R^4$)($R^5$);
each $R^3$ is independently selected from:
  (1) phenyl;
  (2) substituted phenyl with 1, 2, or 3 substituents independently selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen,
      (ii) $C_{1-6}$ alkyl,
      (iii) —$CF_3$, and
      (iv) hydroxy;
  (3) thienyl;
  (4) substituted thienyl substituted on a carbon atom with one or two substituents independently selected from:
    (a) halogen,
    (b) $C_{1-6}$ alkyl,
    (c) $C_{1-6}$ alkyloxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen,
      (ii) $C_{1-6}$ alkyl,
      (iii) —$CF_3$, and
      (iv) hydroxy;
  (5) pyridyl;
  (6) substituted pyridyl substituted on a carbon atom with one or two substituents independently selected from:
    (a) halogen,
    (b) $C_{1-6}$ alkyl,
    (c) $C_{1-6}$ alkyloxy-,
    (d) phenyl,
    (e) —$CF_3$, (f) —OCF$_3$,
(g) —CN,
(h) hydroxy,
(i) phenyloxy, and
(j) substituted phenyloxy with 1, 2, or 3 substituents selected from:
  (i) halogen,
  (ii) C$_{1-6}$ alkyl,
  (iii) —CF$_3$, and
  (iv) hydroxy;

(7) pyrrolyl;
(8) pyrazolyl;
(9) C$_{3-6}$ cycloalkyl,
(10) substituted C$_{3-6}$ cycloalkyl with 1 or 2 substituents independently selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O, and
  (h) hydroxy;
(11) piperidinyl;
(12) substituted piperidinyl substituted on a carbon atom with one or two substituents independently selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O, and
  (h) hydroxy;
(13) naphthyl;
(14) indolyl; and
(15) C$_{3-6}$ cycloalkyl fused with a phenyl ring;

each R$^4$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$, and
(7) —S(O)$_n$—R$^3$; and each R$^5$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$,
(7) —C$_{2-3}$ alkenyl-R$^3$, and
(8) —S(O)$_n$—R$^3$;

each R$^6$ is independently selected from:
(1) —C$_{1-3}$ alkyl-R$^3$, and
(2) —R$^3$;

R$^8$ is H; and
each n is independently selected from 0, 1 and 2;
and provided that when A is thienyl or thiazolyl and R$^2$ is —R$^3$ wherein R$^3$ is unsubstituted phenyl, then R$^1$ is not
(1) —H or
(2) —CH$_3$.

27. The compound according to claim 26, and tautomers and pharmaceutically acceptable salts thereof, wherein each R$^3$ is independently selected from:

(1) substituted phenyl with 1, 2, or 3 substituents independently selected from:
  (a) halogen,
  (b) C$_{1-6}$ alkyl,
  (c) C$_{1-6}$ alkyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen,
    (ii) C$_{1-6}$ alkyl,
    (iii) —CF$_3$, and
    (iv) hydroxy;
(2) thienyl;
(3) substituted thienyl substituted on a carbon atom with one or two substituents independently selected from:
  (a) halogen,
  (b) C$_{1-6}$ alkyl,
  (c) C$_{1-6}$ alkyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen,
    (ii) C$_{1-6}$ alkyl,
    (iii) —CF$_3$, and
    (iv) hydroxy;
(4) pyridyl;
(5) substituted pyridyl substituted on a carbon atom with one or two substituents independently selected from:
  (a) halogen,
  (b) C$_{1-6}$ alkyl,
  (c) C$_{1-6}$ alkyloxy-,
  (d) phenyl,
  (e) —CF$_3$,
  (f) —OCF$_3$,
  (g) —CN,
  (h) hydroxy,
  (i) phenyloxy, and
  (j) substituted phenyloxy with 1, 2, or 3 substituents selected from:
    (i) halogen,
    (ii) C$_{1-6}$ alkyl,
    (iii) —CF$_3$, and
    (iv) hydroxy;
(6) pyrrolyl;
(7) pyrazolyl;
(8) C$_{3-6}$ cycloalkyl,
(9) substituted C$_{3-6}$ cycloalkyl with 1 or 2 substituents independently selected from:
  (a) halogen,
  (b) C$_{1-6}$ alkyl,
  (c) C$_{1-6}$ alkyloxy-,
  (d) —CF$_3$,
  (e) —OCF$_3$,
  (f) —CN,
  (g) =O, and
  (h) hydroxy;

(10) piperidinyl;
(11) substituted piperidinyl substituted on a carbon atom with one or two substituents independently selected from:
  (a) halogen,
  (b) $C_{1-6}$ alkyl,
  (c) $C_{1-6}$ alkyloxy-,
  (d) —$CF_3$,
  (e) —$OCF_3$,
  (f) —CN,
  (g) =O, and
  (h) hydroxy;
(12) naphthyl;
(13) indolyl; and
(14) $C_{3-6}$ cycloalkyl fused with a phenyl ring.

28. The compound according to claim 24 of structural formula:

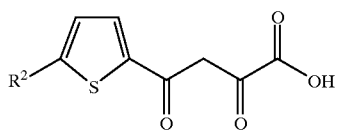

and tautomers and pharmaceutically acceptable salts thereof, wherein:
$R^2$ is selected from:
  (1) —$R^3$,
  (2) —$C_{1-6}$ alkyl substituted with $R^3$,
  (3) —O—$R^6$,
  (4) —S(O)n—$R^6$,
  (5) —$C_{1-6}$ alkyl $(OR^6)(R^4)$,
  (6) —$C_{1-6}$ alkyl $(OR^4)(R^6)$,
  (7) —$C_{0-6}$ alkyl-$N(R^4)(R^6)$,
  (8) —$C_{1-6}$ alkyl $S(O)n$—$R^6$,
  (9) —$C_{0-6}$ alkyl $C(O)$—$R^6$,
  (10) —$C_{0-6}$ alkyl $NR^4C(O)$—$R^6$, and
  (11) —$C_{0-6}$ alkyl-$C(O)N(R^4)(R^5)$;
each $R^3$ is independently selected from:
  (1) phenyl,
  (2) substituted phenyl with 1, 2, or 3 substituents independently selected from:
    (a) halogen selected from —F, —Cl, and —Br,
    (b) $CH_3$,
    (c) methoxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen selected from —F, —Cl, and —Br,
      (ii) —$CH_3$,
      (iii) —$CF_3$, and
      (iv) hydroxy;
  (3) thienyl,
  (4) pyridyl,
  (5) pyrrolyl,
  (6) pyrazolyl,
  (7) $C_{3-6}$ cycloalkyl,
  (8) piperidinyl,
  (9) naphthyl,
  (10) indolyl, and
  (11) $C_{3-6}$ cycloalkyl fused with a phenyl ring;
each $R^4$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$, and
  (7) —$S(O)_n$—$R^3$,
each $R^5$ is independently selected from:
  (1) —H,
  (2) —$C_{1-3}$ alkyl,
  (3) —$CF_3$,
  (4) —$R^3$,
  (5) —$C_{2-3}$ alkenyl,
  (6) —$C_{1-3}$ alkyl-$R^3$,
  (7) —$C_{2-3}$ alkenyl-$R^3$, and
  (8) —$S(O)_n$—$R^3$,
each $R^6$ is independently selected from:
  (1) —$C_{1-3}$ alkyl-$R^3$, and
  (2) —$R^3$; and
each n is independently selected from 0, 1 and 2;
and provided that when $R^2$ is —$R^3$, then $R^3$ is not unsubstituted phenyl.

29. The compound according to claim 28, and tautomers and pharmaceutically acceptable salts thereof, wherein each $R^3$ is independently selected from:
  (1) substituted phenyl with 1, 2, or 3 substituents independently selected from:
    (a) halogen selected from —F, —Cl, and —Br,
    (b) $CH_3$,
    (c) methoxy-,
    (d) phenyl,
    (e) —$CF_3$,
    (f) —$OCF_3$,
    (g) —CN,
    (h) hydroxy,
    (i) phenyloxy, and
    (j) substituted phenyloxy with 1, 2, or 3 substituents selected from:
      (i) halogen selected from —F, —Cl, and —Br,
      (ii) —$CH_3$,
      (iii) —$CF_3$, and
      (iv) hydroxy;
  (2) thienyl,
  (3) pyridyl,
  (4) pyrrolyl,
  (5) pyrazolyl,
  (6) $C_{3-6}$ cycloalkyl,
  (7) piperidinyl,
  (8) naphthyl,
  (9) indolyl, and
  (10) $C_{3-6}$ cycloalkyl fused with a phenyl ring.

30. The compound according to claim 24 of structural formula:

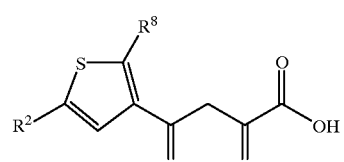

and tautomers and pharmaceutically acceptable salts thereof, wherein:

$R^2$ is selected from:
(1) —$R^3$,
(2) —$C_{1-6}$ alkyl substituted with $R^3$,
(3) —O—$R^6$,
(4) —S(O)n—$R^6$,
(5) —$C_{1-6}$ alkyl (O$R^6$)($R^4$),
(6) —$C_{1-6}$ alkyl (O$R^4$)($R^6$),
(7) —$C_{0-6}$ alkyl-N($R^4$)($R^6$),
(8) —$C_{1-6}$ alkyl S(O)n—$R^6$,
(9) —$C_{0-6}$ alkyl C(O)—$R^6$,
(10) —$C_{0-6}$ alkyl N$R^4$C(O)—$R^6$, and
(11) —$C_{0-6}$ alkyl-C(O)N($R^4$)($R^6$);

each $R^3$ is independently selected from:
(1) phenyl,
(2) substituted phenyl with 1, 2, or 3 substituents independently selected from:
(a) halogen selected from —F, —Cl, and —Br,
(b) $CH_3$,
(c) methoxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen selected from —F, —Cl, and —Br,
(ii) —$CH_3$,
(iii) —$CF_3$, and
(iv) hydroxy;
(3) thienyl,
(4) pyridyl,
(5) pyrrolyl,
(6) pyrazolyl,
(7) $C_{3-6}$ cycloalkyl,
(8) piperidinyl,
(9) naphthyl,
(10) indolyl, and
(11) $C_{3-6}$ cycloalkyl fused with a phenyl ring;

each $R^4$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$, and
(7) —S(O)$_n$—$R^3$, each $R^5$ is independently selected from:
(1) —H,
(2) —$C_{1-3}$ alkyl,
(3) —$CF_3$,
(4) —$R^3$,
(5) —$C_{2-3}$ alkenyl,
(6) —$C_{1-3}$ alkyl-$R^3$,
(7) —$C_{2-3}$ alkenyl-$R^3$, and
(8) —S(O)$_n$—$R^3$, each $R^6$ is independently selected from:
(1) —$C_{1-3}$ alkyl-$R^3$, and
(2) —$R^3$; and $R^8$ is selected from methyl and hydrogen; and
each n is independently selected from 0, 1 and 2;
and provided that when $R^2$ is —$R^3$, then $R^3$ is not unsubstituted phenyl.

31. The compound according to claim 30, and tautomers and pharmaceutically acceptable salts thereof, wherein each $R^3$ is independently selected from:

(1) substituted phenyl with 1, 2, or 3 substituents independently selected from:
(a) halogen selected from —F, —Cl, and —Br,
(b) $CH_3$,
(c) methoxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:
(i) halogen selected from —F, —Cl, and —Br,
(ii) —$CH_3$,
(iii) —$CF_3$, and
(iv) hydroxy;
(2) thienyl,
(3) pyridyl,
(4) pyrrolyl,
(5) pyrazolyl,
(6) $C_{3-6}$ cycloalkyl,
(7) piperidinyl,
(8) naphthyl,
(9) indolyl, and
(10) $C_{3-6}$ cycloalkyl fused with a phenyl ring.

32. The compound according to claim 24, of structural formula:

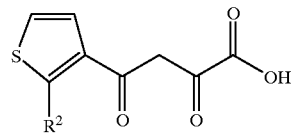

and tautomers and pharmaceutically acceptable salts thereof, wherein:

$R^2$ is selected from:
(1) —$R^3$,
(2) —$C_{1-6}$ alkyl substituted with $R^3$,
(3) —O—$R^6$,
(4) —S(O)n—$R^6$,
(5) —$C_{1-6}$ alkyl (O$R^6$)($R^4$),
(6) —$C_{1-6}$ alkyl (O$R^4$)($R^6$),
(7) —$C_{0-6}$ alkyl-N($R^4$)($R^6$),
(8) —$C_{1-6}$ alkyl S(O)n—$R^6$,
(9) —$C_{0-6}$ alkyl C(O)—$R^6$,
(10) —$C_{0-6}$ alkyl N$R^4$C(O)—$R^6$, and
(11) —$C_{0-6}$ alkyl-C(O)N($R^4$)($R^5$);

each $R^3$ is independently selected from:
(1) phenyl,
(2) substituted phenyl with 1, 2, or 3 substituents independently selected from:
(a) halogen selected from —F, —Cl, and —Br,
(b) $CH_3$,
(c) methoxy-,
(d) phenyl,
(e) —$CF_3$,
(f) —$OCF_3$,
(g) —CN,
(h) hydroxy,
(i) phenyloxy, and
(j) substituted phenyloxy with 1, 2, or 3 substituents selected from:

(i) halogen selected from —F, —Cl, and —Br,
(ii) —CH$_3$,
(iii) —CF$_3$, and
(iv) hydroxy;
(3) thienyl,
(4) pyridyl,
(5) pyrrolyl,
(6) pyrazolyl,
(7) C$_{3-6}$ cycloalkyl,
(8) piperidinyl,
(9) naphthyl,
(10) indolyl, and
(11) C$_{3-6}$ cycloalkyl fused with a phenyl ring;
each R$^4$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$, and
(7) —S(O)$_n$—R$^3$,
each R$^5$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$,
(7) —C$_{2-3}$ alkenyl-R$^3$, and
(8) —S(O)$_n$—R$^3$,
each R$^6$ is independently selected from:
(1) —C$_{1-3}$ alkyl-R$^3$, and
(2) —R$^3$; and
each n is independently selected from 0, 1 and 2;
and provided that when R$^2$ is —R$^3$, then R$^3$ is not unsubstituted phenyl.

33. The compound according to claim 32, and tautomers and pharmaceutically acceptable salts thereof, wherein each R$^3$ is independently selected from:
(1) substituted phenyl with 1, 2, or 3 substituents independently selected from:
(a) halogen selected from —F, —Cl, and —Br,
(b) CH$_3$,
(c) methoxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen selected from —F, —Cl, and —Br,
(ii) —CH$_3$,
(iii) —CF$_3$, and
(iv) hydroxy;
(2) thienyl,
(3) pyridyl,
(4) pyrrolyl,
(5) pyrazolyl,
(6) C$_{3-6}$ cycloalkyl,
(7) piperidinyl,
(8) naphthyl,
(9) indolyl, and
(10) C$_{3-6}$ cycloalkyl fused with a phenyl ring.

34. The compound according to claim 24 of structural formula:

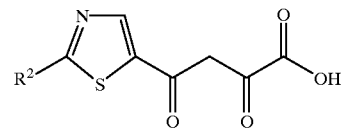

and tautomers and pharmaceutically acceptable salts thereof, wherein:

R$^2$ is selected from:
(1) —R$^3$,
(2) —C$_{1-6}$ alkyl substituted with R$^3$,
(3) —O—R$^6$,
(4) —S(O)n—R$^6$,
(5) —C$_{1-6}$ alkyl (OR$^6$)(R$^4$),
(6) —C$_{1-6}$ alkyl (OR$^4$)(R$^6$),
(7) —C$_{0-6}$ alkyl-N(R$^4$)(R$^6$),
—C$_{1-6}$ alkyl S(O)n—R$^6$,
—C$_{0-6}$ alkyl C(O)—R$^6$,
—C$_{0-6}$ alkyl NR$^4$C(O)—R$^6$, and
—C$_{0-6}$ alkyl-C(O)N(R$^4$)(R$^5$);
each R$^3$ is independently selected from:
(1) substituted phenyl with 1, 2, or 3 substituents independently selected from:
(a) halogen selected from —F, —Cl, —Br,
(b) CH$_3$,
(c) methoxy-,
(d) phenyl,
(e) —CF$_3$,
(f) —OCF$_3$,
(g) —CN,
(h) hydroxy,
(i) phenyloxy, and
(j) substituted phenyloxy with 1, 2, or 3 substituents selected from:
(i) halogen selected from —F, —Cl, —Br,
(ii) —CH$_3$,
(iii) —CF$_3$, and
(iv) hydroxy;
(2) thienyl,
(3) pyridyl,
(4) imidazolyl,
(5) pyrrolyl,
(6) pyrazolyl,
(7) C$_{3-6}$ cycloalkyl,
(8) piperidinyl,
(9) morpholinyl,
(10) naphthyl,
(11) indolyl, and
(12) C$_{3-6}$ cycloalkyl fused with a phenyl ring;
each R$^4$ is independently selected from:
(1) —H,
(2) —C$_{1-3}$ alkyl,
(3) —CF$_3$,
(4) —R$^3$,
(5) —C$_{2-3}$ alkenyl,
(6) —C$_{1-3}$ alkyl-R$^3$, and
(7) —S(O)$_n$—R$^3$, each $R^5$ is independently selected from:
- (1) —H,
- (2) —$C_{1-3}$ alkyl,
- (3) —$CF_3$,
- (4) —$R^3$,
- (5) —$C_{2-3}$ alkenyl,
- (6) —$C_{1-3}$ alkyl-$R^3$,
- (7) —$C_{2-3}$ alkenyl-$R^3$, and
- (8) —$S(O)_n$—$R^3$, each $R^6$ is independently selected from:
- (1) —$C_{1-3}$ alkyl-$R^3$, and
- (2) —$R^3$; and each n is independently selected from 0, 1 and 2.

* * * * *